US009700508B2

(12) United States Patent
Danagher et al.

(10) Patent No.: US 9,700,508 B2
(45) Date of Patent: Jul. 11, 2017

(54) PHARMACEUTICAL COMPOSITIONS COMPRISING HYDROMORPHONE AND NALOXONE

(75) Inventors: Helen Kathleen Danagher, Cambridge (GB); Hassan Mohammad, Cambridge (GB); Malcolm Walden, Cambridge (GB); Geoffrey Gerard Hayes, Cambridge (GB); Jonathon Oliver Whitehouse, Cambridge (GB); Thinnayam Naganathan Krishnamurthy, Scarborough (CA); Ricardo Alberto Vargas Rincon, Mississauga (CA)

(73) Assignee: Euro-Celtique S.A., Luxembourg (GB)

( * ) Notice: Subject to any disclaimer, the term of this patent is extended or adjusted under 35 U.S.C. 154(b) by 825 days.

(21) Appl. No.: 13/697,197

(22) PCT Filed: May 10, 2011

(86) PCT No.: PCT/EP2011/057566
§ 371 (c)(1),
(2), (4) Date: Mar. 27, 2013

(87) PCT Pub. No.: WO2011/141488
PCT Pub. Date: Nov. 17, 2011

(65) Prior Publication Data
US 2013/0178492 A1  Jul. 11, 2013

(30) Foreign Application Priority Data

May 10, 2010  (EP) .................................. 10162428

(51) Int. Cl.
| *A61K 9/00* | (2006.01) |
| *A61K 9/20* | (2006.01) |
| *A61K 9/28* | (2006.01) |
| *A61K 9/50* | (2006.01) |
| *A61K 31/485* | (2006.01) |
| *A61K 9/16* | (2006.01) |

(52) U.S. Cl.
CPC .......... *A61K 9/0002* (2013.01); *A61K 9/1676* (2013.01); *A61K 9/2027* (2013.01); *A61K 9/2054* (2013.01); *A61K 9/2095* (2013.01); *A61K 9/2846* (2013.01); *A61K 9/2866* (2013.01); *A61K 9/5078* (2013.01); *A61K 31/485* (2013.01); *A61K 9/1635* (2013.01); *A61K 9/1652* (2013.01)

(58) Field of Classification Search
None
See application file for complete search history.

(56) References Cited

U.S. PATENT DOCUMENTS

| 4,366,310 A | 12/1982 | Leslie |
| 4,457,933 A | 7/1984 | Gordon et al. |
| 4,647,599 A | 3/1987 | Bezzegh et al. |
| 4,705,695 A | 11/1987 | Lehmann et al. |
| 4,769,372 A | 9/1988 | Kreek |
| 5,958,452 A | 9/1999 | Oshlack et al. |
| 6,419,959 B1 | 7/2002 | Walter et al. |
| 6,488,961 B1 | 12/2002 | Robinson et al. |
| 6,716,449 B2 | 4/2004 | Oshlack et al. |
| 2003/0004177 A1* | 1/2003 | Kao ........................ A61K 9/209 514/282 |
| 2004/0081694 A1 | 4/2004 | Oshlack et al. |
| 2004/0176402 A1 | 9/2004 | Oshlack et al. |
| 2004/0242617 A1 | 12/2004 | Christoph |
| 2005/0025802 A1 | 2/2005 | Richard et al. |
| 2005/0079221 A1 | 4/2005 | Groenewoud |
| 2005/0095291 A1 | 5/2005 | Oshlack et al. |
| 2005/0232987 A1 | 10/2005 | Srinivasan |
| 2005/0245483 A1 | 11/2005 | Brogmann et al. |
| 2005/0245556 A1 | 11/2005 | Brogmann et al. |
| 2006/0039970 A1 | 2/2006 | Oshlack et al. |
| 2007/0014732 A1 | 1/2007 | Sackler |
| 2007/0026025 A1 | 2/2007 | Mitchell |
| 2007/0048364 A1 | 3/2007 | Peng et al. |
| 2007/0141147 A1 | 6/2007 | Heil et al. |
| 2007/0259045 A1 | 11/2007 | Mannion et al. |
| 2007/0298103 A1 | 12/2007 | Hayes |
| 2008/0145429 A1* | 6/2008 | Leyendecker et al. ........ 424/488 |
| 2008/0280921 A1 | 11/2008 | Dreyer et al. |
| 2010/0151011 A1 | 6/2010 | Benke |
| 2010/0183687 A1 | 7/2010 | Cox et al. |
| 2010/0210843 A1 | 8/2010 | Hudson et al. |
| 2010/0226943 A1 | 9/2010 | Brennan et al. |
| 2010/0227876 A1 | 9/2010 | Rech |

(Continued)

FOREIGN PATENT DOCUMENTS

| DE | 10215131 A1 | 10/2003 |
| EC | SP1998-2720 | 10/1998 |

(Continued)

OTHER PUBLICATIONS

International Application No. PCT/GB2010/050948: International Search Report, European Patent Office, Netherlands, mailed on Dec. 1, 2011.
International Application No. PCT/GB2010/050948: International Preliminary Report on Patentability and Written Opinion, The International Bureau of WIPO, Geneva, Switzerland, mailed on Dec. 15, 2011.
International Application No. PCT/EP2011/057568: International Search Report dated Aug. 17, 2011.
International Application No. PCT/EP2011/057567: International Search Report dated Aug. 9, 2011.
International Application No. PCT/EP2011/057566: International Search Report dated Feb. 3, 2012.
Oliveto et al., "Hydromorphone-naloxone combinations in opioid-dependent humans under a naloxone novel-response discrimination procedure," Exp. and Clin. Psychopharmacology, vol. 6, No. 2, 169-178 (1998).
Taiwan Application No. 100116427: Office Action and Search Report dated Mar. 12, 2013.
Mansour et al., "Materials for Pharmaceutical Dosage Forms: Molecular Pharmaceutics and Controlled Release Drug Delivery Aspects," Int. J. Mol. Sci. 2010, 11, 3298-3322.

(Continued)

*Primary Examiner* — Robert A Wax
*Assistant Examiner* — Randeep Singh
(74) *Attorney, Agent, or Firm* — Dechert LLP

(57) ABSTRACT

The present invention relates to prolonged release pharmaceutical dosage forms, the manufacture thereof as well as their use for administration to human beings.

48 Claims, 2 Drawing Sheets

(56) References Cited

U.S. PATENT DOCUMENTS

| | | |
|---|---|---|
| 2010/0331354 A1 | 12/2010 | Wermeling |
| 2011/0077222 A1 | 3/2011 | Schaefer et al. |
| 2011/0077238 A1 | 3/2011 | Leech et al. |
| 2011/0172259 A1 | 7/2011 | Leyendecker et al. |
| 2012/0108621 A1 | 5/2012 | Brogmann et al. |
| 2012/0135075 A1 | 5/2012 | Mohammad |
| 2012/0183612 A1 | 7/2012 | Brogmann et al. |
| 2012/0225901 A1 | 9/2012 | Leyendecker et al. |
| 2013/0330409 A1 | 12/2013 | Mohammad |

FOREIGN PATENT DOCUMENTS

| | | |
|---|---|---|
| EC | SP2000-3314 | 1/2000 |
| EC | SP2010-10416 | 8/2010 |
| EP | 0425154 A1 | 5/1991 |
| EP | 0714661 A1 | 6/1996 |
| EP | 1557179 A1 | 7/2005 |
| EP | 1695700 | 8/2006 |
| EP | 1813276 A1 | 8/2007 |
| EP | 1961421 A1 | 8/2008 |
| EP | 2255808 | 5/2011 |
| FR | 2946533 | 12/2010 |
| GB | 2418854 A | 4/2006 |
| GB | 2447898 A | 10/2008 |
| JP | 2006265184 | 10/2006 |
| WO | WO 97-16172 A1 | 5/1997 |
| WO | WO 99-01111 A1 | 1/1999 |
| WO | WO 99-32119 A1 | 7/1999 |
| WO | WO 01/58447 A1 | 8/2001 |
| WO | WO 02060385 | 8/2002 |
| WO | WO 02/092060 | 11/2002 |
| WO | WO 02/100382 | 12/2002 |
| WO | WO 03/013479 | 2/2003 |
| WO | WO 03/013525 A1 | 2/2003 |
| WO | WO 03/018588 | 3/2003 |
| WO | WO 03024444 A1 | 3/2003 |
| WO | WO 03-084504 A2 | 10/2003 |
| WO | WO 2004004683 | 1/2004 |
| WO | WO 2004091622 | 10/2004 |
| WO | WO 2004091623 | 10/2004 |
| WO | WO 2004091665 | 10/2004 |
| WO | WO 2004/098567 | 11/2004 |
| WO | WO 2005/077957 | 8/2005 |
| WO | WO 2005079760 | 9/2005 |
| WO | WO 2005/097801 | 10/2005 |
| WO | WO 2005117873 | 12/2005 |
| WO | WO 2006/043025 A1 | 4/2006 |
| WO | WO 2006038226 | 4/2006 |
| WO | WO 2006078842 | 7/2006 |
| WO | WO 2006-079550 A2 | 8/2006 |
| WO | WO 2006/133941 | 12/2006 |
| WO | WO 2007/013047 A2 | 2/2007 |
| WO | WO 2007/039122 A2 | 4/2007 |
| WO | WO 2007/068615 A2 | 6/2007 |
| WO | WO 2008/023261 | 2/2008 |
| WO | WO 2008-049657 A2 | 5/2008 |
| WO | WO 2010032073 | 3/2010 |
| WO | WO 2010032128 | 3/2010 |
| WO | WO 2010034342 | 4/2010 |
| WO | WO 2010034344 | 4/2010 |
| WO | WO 2010068789 | 6/2010 |
| WO | WO 2010078486 | 7/2010 |
| WO | WO 2010081034 | 7/2010 |
| WO | WO 2010088911 | 8/2010 |
| WO | WO 2010096045 | 8/2010 |
| WO | WO 2010096788 | 8/2010 |
| WO | WO 2010096790 | 8/2010 |
| WO | WO 2010103039 | 9/2010 |
| WO | WO 2010105672 | 9/2010 |
| WO | WO 2010105673 | 9/2010 |
| WO | WO 2010112942 | 10/2010 |
| WO | WO 2010120232 | 10/2010 |
| WO | WO 2010121619 | 10/2010 |
| WO | WO 2010123999 | 10/2010 |
| WO | WO 2010/140007 A2 | 12/2010 |
| WO | WO 2010141505 | 12/2010 |
| WO | WO 2010142814 | 12/2010 |
| WO | WO 2010144641 | 12/2010 |
| WO | WO 2011009020 | 1/2011 |
| WO | WO 2011009602 | 1/2011 |
| WO | WO 2011009603 | 1/2011 |
| WO | WO 2011021029 | 2/2011 |
| WO | WO 2011031350 | 3/2011 |
| WO | WO 2011/141489 A1 | 11/2011 |
| WO | WO 2011/141490 A1 | 11/2011 |
| WO | WO 2012076907 | 6/2012 |

OTHER PUBLICATIONS

Index Merck 14th, Merck & Co., USA, 2006, No. 0006362, 0004803.

Azamari et al., "Thermal treating as a tool for sustained release of indomethacin from Eudragit RS and RL matrices," International Journal of Pharmaceutics, 246, 171-177 (2002).

Bell et al., "The prevalence, severity, and impact of opioid-induced bowel dysfunction: results of a US and European Patient Survey (PROBE 1)," *Pain Medicine*, 10(1):35-42 (2009).

Clinical Trials Study No. NCT00992576, "Optimisation of Hydromorphone—Naloxone Ratio for the Treatment of Pain," ClinicalTrials.gov (2009).

Holzer, "New Approaches to the Treatment of Opioid-Induced Constipation," *Eur. Rev. Med. Pharmacol. Sci.*, 12 Suppl 1:119-27 (2008).

Kalso et al., "Opioids in Chronic Non-Cancer Pain: Systematic Review of Efficacy and Safety," *Pain*, 112, 372-380 (2004).

Liu et al., "Low-dose Oral Naloxone Reverses Opioid-Induced Constipation and Analgesia," *J. Pain Symptom Manage*, 23(1):48-53 (2002).

Palladone® retard 4, 8, 16, 24 mg, Product Label (2011).

Portenoy, "Constipation in the Cancer Patient: Causes and ManagementTreatment of Constipation" *Cancer Pain*, 71(2):303-311 (1987).

Rentz et al., "Validation of the Bowel Function Index to Detect Clinically Meaningful Changes in Opioid-Induced Constipation," *Journal of Medical Economics*, 12(0):371-383 (2009).

Abbaspour et al, "*Thermal treating as a tool to produce plastic pellets based on Eudragit RS PO and RL PO aimed for tabletting*", European Journal of Pharmaceutics and Biopharmaceutics 2007, 67, pp. 260-267.

Alvarez, "Sustained Release—Comparison of Acrylic & Cellulose-Based Matrix Formers for Sustained Drug Release", Drug Delivery Technology 2006, vol. 6., No. 3.

Azarmi et al, "*Mechanistic evaluation of the effect of thermal-treating on Eudragit RS matrices*", Il farmaco 2005, 50, pp. 925-930.

Billa et al, "*Diclofenac Release from Eudragit-Containing Matrices and Effects of Thermal Treatment*", Drug Development and Industrial Pharmacy 1998, 24, pp. 45-50.

Cameron et al, "*Controlled-Release Theophylline Tablet Formulations containing Acrylic Resins, II. Combination Resin Formulations*", Drug Development and Industrial Pharmacy 1987, 13, pp. 1409-1427.

Clemens et al, "*Bowel function during pain therapy with oxycodone/ naloxone prolonged release tablets in patients with advanced cancer*", International Journal of Clinical Practice 2011, 65, pp. 472-478.

Coleman, "*Reducing the abuse potential of controlled substances*", Pharmaceutical Medicine 2010, 24, pp. 24-36.

Davis et al, "*Recent development in therapeutics for breakthrough pain*", Expert Review of Neuropathics 2010, 10, pp. 757-773.

Draganoiu et al, "*Development and in vitro / in vivo Evaluation of Extended Release Propranolol Tablets*", Pharm. Ind. 2006, 68, pp. 111-115.

Dumicic et al, "*The effect of water on matrix formation in sustained release tablets containing poly(ethyl acrylate, methyl methacrylate)*", J. Drug Del. Sci. Tech. 2005, 15, pp. 389-395.

European Pharmacopoeia, 4th Edition, Directorate for the Quality of Medicines of the Council of Europe, Council of Europe Strasbourg, 2001, ISBN:92-871-4587-3, p. 535.

(56) References Cited

OTHER PUBLICATIONS

Goforth et al, "*Hydromorphone-OROS formulation*", Expert Opinion on Pharmacotherapy 2010, 11, pp. 1207-1214.

Haririan et al, "*Formulation of Controlled Release Matrix Tables of Isosorbide Dinitrate*", Indian Journal of Pharmaceutical Sciences 2001, 63, pp. 24-29.

Jenquin et al, "*Relationship of Film Properties to Drug Release from Monolithic Films Containing Adjuvants*", Journal of Pharmaceutical Science 1992, 81, pp. 983-989.

Jost, "*Management of cancer pain: ESMO Clinical Practice Guidelines*", Annals of Oncology 2010, 21, pp. v257-v260.

Kao et al, "*The Influence of Eudragit S-100 on the Release of Chlopheniramine Maleate from Matrix Tablets Containing Eudragit RS-PM*", The Chinese Pharmaceutical Journal 1994, 46, 257-267.

Krajacic et al, "*Matrix formation in sustained release tablets: possible mechanism of dose dumping*", International Journal of Pharmaceutics 2003, 251, pp. 67-78.

Leppert, "*Dihydrocodeine as an opioid analgesic for the treatment of moderate to severe chronic pain*", Current Drug Metabolism 2010, 11, pp. 494-506.

Leppert, "*Role of oxycodone/naloxone in cancer pain management*", Pharmacological Reports 2010, 62, 578-591.

Oxycodone / Naloxone Combination Tablet Reduces Opioid-induced Bowel Dysfunction in Patients with Chronic Severe Pain, XP00263606, [Online], Sep. 27, 2007 [retrieved on May 5, 2011] Retrieved from the internet: <URL: http://www.medicalnewstoday.com/printerfriendlynews.php?newsid=83795>, pp. 1-2.

Sadeghi et al, "*Tableting of Eudragit RS and Propranolol Hydrochloride Solid Dispersion: Effect of Particle Size, Compaction Force, and Plasticizer Addition on Drug Release*", Drug Development and Industrial Pharmacy 2004, 30, pp. 759-766.

Vela et al, "*Effect of Acrylic Resins on the Rheological and Compressibility Properties of Paracetamol: Formulation of directly compressible Matrix Systems*", Il farmaco 1995, 50, pp. 201-215.

Woods et al, "*Opioid abuse and dependence: Treatment review and future options*", Formulary 2010, 45, pp. 284-291.

Wurster et al, "*Effect of Curing on Water Diffusivities in Acrylate Free Films as Measured via Sorption Technique*", AAPS PharmSciTech 2007, 8, pp. E1-E6.

Yasser et al, "*Effect of Eudragit® RS 30D and Talc Powder on Verapamil Hydrochloride Release from Beads Coated with Drug Layered Matrices*", AMPS PharmSciTech 2007, 9, pp. 75-83.

\* cited by examiner

Untreated tablet core

Heat treated tablet core @ 55C for 30 mins

FIG. 2

SUMMARY OF RESULTS
HYDROMORPHONE
N = 11

| Parameters | | Test (Hydromorphicone-Naloxone) | | | | | | Reference (Hydromorph Contin (C)) | | |
|---|---|---|---|---|---|---|---|---|---|---|
| | | Test-1 (A) N = 11 | | | Test-2 (B) N = 10 | | | N = 11 | | |
| | | Mean | SD | CV (%) | Mean | SD | CV (%) | Mean | SD | CV (%) |
| $AUC_{0-t}$ | (pg·h/mL) | 6027.10 | 1602.27 | 26.58 | 5721.45 | 1850.89 | 32.35 | 5905.86 | 1749.06 | 29.62 |
| $AUC_{0-inf}$ | (pg·h/mL) | 7762.05 | 2923.79 | 37.67 | 7440.21 | 2831.42 | 38.06 | 7131.66 | 1723.95 | 24.17 |
| $AUC_{0-inf}$ | (%) | 81.49 | 14.83 | 18.20 | 80.08 | 15.39 | 19.22 | 82.63 | 10.76 | 13.02 |
| $AUC_{t1/2h}$ | (pg·h/mL) | 2808.57 | 654.85 | 23.32 | 2818.37 | 1056.88 | 37.50 | 2782.87 | 1018.48 | 36.60 |
| $AUC_{t1/2inf}$ | (%) | 38.72 | 9.74 | 25.16 | 39.36 | 9.31 | 23.65 | 38.72 | 8.09 | 20.89 |
| $C_{max}$ | (pg/mL) | 454.34 | 159.24 | 35.05 | 568.34 | 257.81 | 45.36 | 392.47 | 124.09 | 31.62 |
| $T_{max}*$ | (h) | 4.23 | 1.91 | 45.26 | 1.56 | 0.34 | 20.34 | 5.27 | 2.53 | 48.00 |
| $T_{lag}*$ | (h) | 5.00 | 2.49 | - | 1.51 | 0.50 | - | 5.00 | 0.99 | - |
| $K_{el}$ | $(h^{-1})$ | 0.0594 | 0.0262 | 44.06 | 0.0539 | 0.0205 | 38.78 | 0.0587 | 0.0218 | 37.11 |
| $T_{1/2}$ | (h) | 14.92 | 9.60 | 64.37 | 16.78 | 12.41 | 73.93 | 13.69 | 5.73 | 42.11 |

* Medians and interquartile ranges are presented.

PHARMACEUTICAL COMPOSITIONS COMPRISING HYDROMORPHONE AND NALOXONE

CROSS REFERENCE TO RELATED APPLICATIONS

This application is a national stage entry of International Application No. PCT/EP2011/057566, filed May 10, 2011, and claims priority under 35 U.S.C. §119(a)-(d) and 365(b) of European Patent Application No. EP 10162428.6, filed 10 May 2010, the contents of all of which are incorporated herein in their entireties by reference thereto.

FIELD OF THE INVENTION

The present invention relates to prolonged release pharmaceutical dosage forms comprising hydromorphone or a pharmaceutically acceptable salt thereof and naloxone or a pharmaceutically acceptable salt thereof, the manufacture thereof as well as their use for administration to human beings.

BACKGROUND OF THE INVENTION

Prolonged release pharmaceutical dosage forms represent an important tool in a medical practisner's armoury for treating diseases. One of the general benefits generally attributed to prolonged release pharmaceutical dosage forms versus immediate release pharmaceutical dosage forms includes increased patient compliance as a consequence of reduced administration frequency.

There are various technologies available for obtaining prolonged release dosage forms. Prolonged release properties may be conveyed by so-called prolonged release matrix systems, prolonged release coatings, osmotic dosage forms, multi-layered dosage forms etc.

When developing a prolonged release formulation, it is generally necessary to choose the respective formulation technology with respect to the physico-chemical and physiological properties of the pharmaceutically active agent(s) in question. This means a substantial amount of work for the formulation specialist. This will be even more so where the dosage form comprises pharmaceutically active agents such as opioid agonists which theoretically can be abused, i.e. are not used for medicinal purposes.

There is thus a continuing interest in pharmaceutical dosage forms which comprise opioid analgesic as pharmaceutically active agents, which provide prolonged release properties and account for opioids' potential of being abused.

SUMMARY OF THE INVENTION

It is an objective of the present invention to provide prolonged release pharmaceutical dosage forms and methods of manufacture thereof.

These and other objectives as they will become apparent from the ensuing description are attained by the subject matter of the independent claims. Some of the preferred embodiments are referred to by the dependent claims.

To some extent, the present invention is based on the finding that one can produce prolonged release pharmaceutical dosage forms comprising hydromorphone or a pharmaceutically acceptable salt or derivative thereof and naloxone or a pharmaceutically acceptable salt or derivative thereof combining various beneficial aspects. These include stability, alcohol tolerance, tamper resistance and the like.

In a first aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition provides alcohol resistance.

In a second aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) hydromorphone or a pharmaceutically acceptable salt or derivative thereof and naloxone or a pharmaceutically acceptable salt or derivative thereof are present in the pharmaceutical composition in a weight ratio in a range of about 2:1 to about 1:3, preferably of about 2:1, about 1:1, about 1:2 or about 1:3.

In an embodiment of this second aspect, the composition may comprise a prolonged release matrix and/or a prolonged release coating.

In a third aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions releases the pharmaceutically active agents with substantially the same release rate as before subjecting the pharmaceutical composition to stressed conditions.

In a fourth aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions has less than 2.0% of total substances related to hydromorphone or a pharmaceutically acceptable salt or derivative thereof and/or related to naloxone or a pharmaceutically acceptable salt or derivative thereof.

In a fifth aspect the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the prolonged release pharmaceutical composition is heat treated.

In a first variation to this fifth aspect the present invention relates to an oral prolonged release pharmaceutical composition comprising at least:
  a) at least one prolonged release material;
  b) at least hydromorphone or a pharmaceutically acceptable salt or derivative thereof and naloxone or a pharmaceutically acceptable salt or derivative thereof,
  c) wherein the at least one prolonged release material and hydromorphone or a pharmaceutically acceptable salt or derivative thereof and naloxone or a pharmaceutically acceptable salt or derivative thereof are combined such that a prolonged release matrix is formed; and
  d) wherein the prolonged release pharmaceutical composition is heat treated.

In a second variation to this fifth aspect the present invention relates to an oral prolonged release pharmaceutical composition comprising at least:
  a) at least one prolonged release material;
  b) at least hydromorphone or a pharmaceutically acceptable salt or derivative thereof and naloxone or a pharmaceutically acceptable salt or derivative thereof;
  c) wherein the at least one prolonged release material and hydromorphone or a pharmaceutically acceptable salt or derivative thereof and naloxone or a pharmaceutically acceptable salt or derivative thereof are combined such that a prolonged release matrix is formed; and
  d) wherein the prolonged release pharmaceutical composition is heat treated;
  e) wherein at least one prolonged release material is applied in the form of a prolonged release coating which is disposed on the prolonged release matrix; and
  f) wherein the composition is optionally cured.

The prolonged release coating may either be disposed on each prolonged release matrix if the prolonged release matrix is manufactured in the form of multi-particulates such as granules or it may be disposed on the formulation comprising the prolonged release matrix if e.g. prolonged release matrix multi-particulates such as granules are compressed into a tablet. The coating will then be disposed on the monolithic formulation.

In a first embodiment of this fifth aspect of the invention and its first and second variation, hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

In addition or alternatively to this first embodiment, in a second embodiment of this fifth aspect of the invention and its first and second variation, the pharmaceutical composition may be alcohol resistant.

In addition or alternatively to this first or second embodiment, in a third embodiment of this fifth aspect of the invention and its first and second variation, the pharmaceutical composition may after storage under stressed conditions release the pharmaceutically active agents with substantially the same release rate as before subjecting the pharmaceutical composition to stressed conditions.

In addition or alternatively to this first, second or third embodiment, in a fourth embodiment of this fifth aspect of the invention and its first and second variation, the pharmaceutical composition may after storage under stressed conditions have less than 3.0% of total substances related to hydromorphone or a pharmaceutically acceptable salt or derivative thereof and/or related to naloxone or a pharmaceutically acceptable salt or derivative thereof.

The invention also relates to a method of manufacturing an oral prolonged release pharmaceutical composition comprising at least the steps of:
  a) producing granules comprising at least one prolonged release material, at least hydromorphone or a pharmaceutically acceptable or derivative salt thereof and at least naloxone or a pharmaceutically acceptable salt or derivative thereof,
  b) optionally selecting granules of step a) of substantially uniform size;
  c) optionally compressing said granules of step a) or step b) to obtain an oral prolonged release pharmaceutical composition in the form of a tablet,
  d) optionally heat treating said compressed granules of step c);
  e) optionally disposing a prolonged release coating either on the granules of step b) which may have been heat treated or on the compressed granules of step c) which may have been heat treated;
  f) optionally curing the composition.

In one embodiment, granules of step a) are manufactured by wet or dry granulation. In another embodiment, the granules are obtained by wet or melt extrusion.

In one embodiment, the granules are optionally screened in order to select granules of substantially uniform size. For example, granules may be selected to have a mean size in the range of about 100 µm to about 2 mm, more preferably in the range of about 100 µm to about 1 mm.

Another aspect of the present invention relates to prolonged release pharmaceutical compositions as they are obtainable by methods in accordance with the invention.

Such pharmaceutical compositions may be alcohol resistant as described hereinafter. They may also provide physical and chemical stability.

The pharmaceutical compositions may be used for treating moderate to severe pain, in particular cancer pain, neuropathic pain, visceral pain or bone pain. When used for treating these types of pain, the pharmaceutical compositions may beneficially influence side effects such as constipation, urinary retention, breath depression and bowel function as they may occur when using only hydromorphone or a pharmaceutically acceptable salt or derivative thereof.

BRIEF DESCRIPTION OF THE DRAWINGS

FIG. 2 shows a summary of the results of a single-dose pK study conducted under fasted conditions in which the controlled release bead dosage forms from Formulation A and Formulation B were tested against Hydromorph Contin™.

DETAILED DESCRIPTION OF THE INVENTION

Figure 1A:
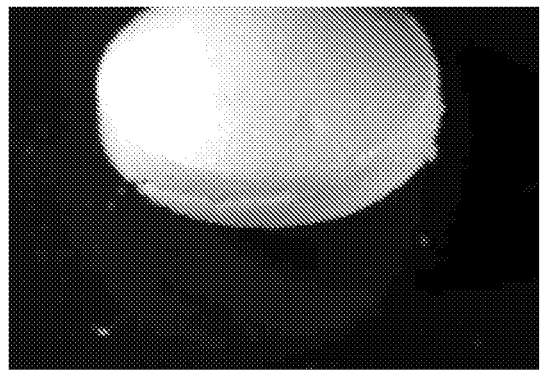
FIG. 1A and FIG. 1B show photographs demonstrating that for, e.g., the case of tablet PN3450 that heat treatment of the prolonged matrix improves the physical stability of the formulation, e.g. in that the appearance of cracks is reduced and the intactness of the tablet is improved.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims. Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

In the context of the present invention the terms "about" or "approximately" denote an interval of accuracy that the person skilled in the art will understand to still ensure the technical effect of the feature in question. The term typically indicates deviation from the indicated numerical value of ±10%, and preferably of ±5%.

The term "in vitro release" and its grammatical variations as well as similar expression refers to the release rate by which a pharmaceutically active agent, e.g. hydromorphone HCl is released from the pharmaceutical composition when the in vitro release rate is tested by the paddle method according to the European Pharmacopeia as described in as described in the Ph. Eur. 2.9.3 $6^{th}$ edition. The paddle speed is typically set at 75 or 100 rpm in 500 ml or 900 ml simulated gastric fluid (SGF) dissolution medium with pH 1.2. Aliquots of the dissolution media are withdrawn at the respective time points and analyzed by HPLC with a C18 column, eluted with 30 mM phosphate buffer in acetonitrile (70:70; pH 2.9) with a flow rate of 1.0 ml/min and detected at 220 nm. It is specifically indicated if in the context of the present invention in vitro release rates are determined using a different test method (such as SGF with 40% (v/v) of ethanol).

The amount of dissolution liquid and the rotational speed of the paddle apparatus may depend on the amount of active agent tested. For example, pharmaceutical compositions comprising up to 16 mg hydromorphone HCl may be tested at 75 rpm in 500 ml dissolution liquid while higher dosage strengths may be tested at 100 rpm in 900 ml dissolution liquid.

The term "Simulated Gastric Fluid, pH 1.2" refers to 0.1 N HCl, pH 1.2.

In the context of the present invention, the terms "immediate release" or "conventional release" refer to pharmaceutical compositions showing a release of the active substance(s) which is not deliberately modified by a special formulation design and/or manufacturing methods. For oral dosage forms this means that the dissolution profile of the active substance(s) depends essentially on its (theirs) intrinsic properties. Typically, the terms "immediate release" or "conventional release" refer to pharmaceutical compositions which release in vitro >75% (by weight) of the pharmaceutically active agent(s) at 45 min.

In the context of the present, the terms "prolonged release" and "controlled release" are used interchangeably and refer to pharmaceutical compositions showing a slower release of the active agent(s) than that of a conventional release pharmaceutical composition administered by the same route. Prolonged or controlled release is achieved by a special formulation design and/or manufacturing method. Typically, the terms "prolonged release" and "controlled release refer to pharmaceutical compositions which release in vitro ≤75% (by weight) of the pharmaceutically active agent at 45 min.

Prolonged release properties may be obtained by different means such as by a coating which is then designated as a prolonged release coating, a matrix which is then designated by as a prolonged release matrix or e.g. by an osmotic structure of the pharmaceutical composition.

In order to obtain "prolonged or controlled release" properties, one typically uses materials which are known to prolong the release from a dosage form comprising e.g. a prolonged release matrix and/or prolonged release coating. Typical examples of such "prolonged or controlled release materials" are hydrophobic polymers such as ethyl cellulose, hydrophilic polymers such as hydroxypropyl cellulose and the like.

The nature of the "prolonged or controlled release material" may depend on whether the release properties are attained by a "prolonged release matrix" or a "prolonged release coating". The term "prolonged release materials" thus describes both types of materials. The term "prolonged release matrix material" indicates that a material is used for obtaining a prolonged release matrix. Likewise, the term "prolonged release coating material" indicate that a material is used for obtaining a prolonged release coating.

The terms "prolonged release matrix formulation" or "controlled release matrix formulation" refer to a pharmaceutical composition including at least one prolonged release material or controlled release material, and at least one hydromorphone and naloxone or the pharmaceutically acceptable salts or derivatives thereof. The terms "prolonged release material" and "controlled release material" can be used interchangeably. In a "prolonged release matrix formulation" or "controlled release matrix formulation", the "prolonged release material" or "controlled release material" are combined with the pharmaceutically active agents to form a mixture from which the pharmaceutically active agent is released over prolonged periods of time, such as e.g. 8, 10, 12, 14, 16, 18, 20, 22 or 24 hours.

It is to be understood that a material will be considered to act as prolonged or controlled release material if the dissolution profile of the pharmaceutically active agent(s) is slowed down compared to an immediate or conventional release formulation. If a prolonged or controlled release material can be used for manufacturing a prolonged or controlled release matrix, it will be considered as a prolonged or controlled release matrix material.

Pharmaceutically acceptable excipients which are used to adjust an already prolonged or controlled release to a specific profile are not necessarily considered to be prolonged or controlled release materials.

It is to be understood that a prolonged release matrix or a controlled release matrix does not necessarily consist only of the pharmaceutically active agent(s) and the prolonged or controlled release material. The prolonged or controlled release matrix may comprise in addition pharmaceutically acceptable excipients such as fillers, lubricants, glidants, etc.

The terms "prolonged release coating formulation" or "controlled release coating formulation" refer to a pharmaceutical composition including at least one prolonged release material or controlled release material, and at least one hydromorphone and naloxone or the pharmaceutically acceptable salts or derivatives thereof. The terms "prolonged release material" and "controlled release material" can be used interchangeably. In a "prolonged release coating formulation" or "controlled release coating formulation", the "prolonged release material" or "controlled release material" are disposed on the pharmaceutically active agents to form a diffusion barrier. Other than in prolonged release matrix formulation, the actives are not intimately mixed with the prolonged release material and the prolonged release coating does not form a three dimensional structure within which the actives are distributed. As the term implies, the prolonged release material forms a layer above the actives. The pharmaceutically active agent is released from a prolonged release coating formulation over prolonged periods of time, such as e.g. 8, 10, 12, 14, 16, 18, 20, 22 or 24 hours.

It is to be understood that a material will be considered to act as prolonged or controlled release material if the dissolution profile of the pharmaceutically active agent(s) is slowed down compared to an immediate or conventional release formulation. If a prolonged or controlled release material can be used for manufacturing a prolonged or controlled release coating, it will be considered as a prolonged or controlled release coating material.

Pharmaceutically acceptable excipients which are used to adjust an already prolonged or controlled release to a specific profile are not necessarily considered to be prolonged or controlled release materials.

When it is mentioned that a prolonged release coating is disposed on pharmaceutically active agents, this is not to be construed as meaning that such a coating will necessarily be directly layered on such active pharmaceutically agents. Of course, if pharmaceutically active agents are layered on a carriers such as non-pareil beads, the coating may be disposed directly thereon. However, the pharmaceutically active agents may also be first embedded in a polymer layer or e.g. a prolonged release matrix. Subsequently the prolonged release coating may be disposed on e.g. granules which comprise a prolonged release matrix or on tablets which are made from such granules by compression for example.

A pharmaceutical composition with a controlled or prolonged release coating may be obtained by combining the pharmaceutically active agents with a carriers such as non-pareil beads and disposing a prolonged release coating on said combinations. Such coating may be made from polymers such cellulose ethers with ethyl cellulose being preferred, acrylic resins, other polymers and mixtures thereof. Such controlled or prolonged release coatings may comprise additional excipients such as pore-formers, binders and the like.

It is further to be understood, that the term "prolonged release matrix formulation" or "controlled release matrix formulation" does not exclude pharmaceutical compositions with a prolonged or controlled release matrix and an additional prolonged or controlled release coating being disposed on the matrix. Likewise the term "prolonged release coating formulation" or "controlled release coating formulation" does not exclude pharmaceutical compositions with a prolonged or controlled release coating which is disposed on prolonged release matrix or a controlled release matrix.

In fact, the invention in various embodiments considers prolonged release matrix formulations which also comprise a prolonged release coating.

The terms "prolonged release dosage form" and "controlled release dosage form" can be used interchangeably and refer to the administration form of a pharmaceutical composition of the present invention comprising the at least one pharmaceutically active agent in prolonged release form as e.g. in form of a "prolonged release matrix formulation", in the form of a "prolonged release coating formulation, combinations thereof or in other prolonged release formulations such as osmotic formulations. The terms "prolonged release matrix formulation" and "prolonged release dosage form" can be used interchangeably if the prolonged release dosage form consists essentially of the prolonged release matrix formulation. This means that a prolonged release dosage form can comprise in addition to the prolonged release matrix e.g. cosmetic coatings and pharmaceutically acceptable excipients such fillers, lubricants, etc.

For some embodiments, the term "prolonged release matrix dosage form" may indicate that the dosage form comprises a prolonged release matrix as the sole structure being responsible for prolonging the release. This, however, does not exclude that the dosage form may comprise an immediate release portion as described hereinafter.

For some embodiments, the term "prolonged release coating dosage form" may indicate that the dosage form comprises a prolonged release coating as the sole structure being responsible for prolonging the release. This, however, does not exclude that the dosage form may comprise an immediate release portion as described hereinafter.

The release rates indicated always refer to the formulation such as a monolithic tablet or multi-particulates. The release rates will be chosen such that a pharmaceutical composition can be administered e.g. on a twice a day or once a day basis, i.e. every 12 hours or every 24 hours. Typically, the release will occur by diffusion through the prolonged or controlled release matrix and/or coating, erosion of the prolonged or controlled matrix and/or coating or combinations thereof.

Oral solid dosage forms may take the form of tablets, granules, multiparticulates, mini-tablets and the like. Mini-tablets are dosage forms which comprise pharmaceutically active agents in a prolonged release matrix with optionally a prolonged release coating disposed thereon. They take a round form with a thickness of about 1 to about 5 mm and a diameter of about 1 to 5 mm. A thickness and diameter of about 1 to about 4 mm, of about 1 to about 3 mm and of about 2 mm is also considered. Multiparticulate and/or mini-tablets may be filled into e.g. capsules are embedded in other excipients to form e.g. a tablet or to be filled into capsules.

In a preferred embodiment, the dosage forms in accordance with the invention comprise a prolonged release matrix with a controlled release coating.

The term "heat treatment" is used in the context of heat treating a prolonged release matrix formulation. The term "curing" is used in the context of heat treating a prolonged release coating formulation and relates to the effects of heat on the coalescence of the coating. If a composition comprises a prolonged release matrix and a prolonged release coating, the term "heat treatment" or "heat treated" denotes that the prolonged release matrix has been heat treated before the prolonged release coating was applied.

Pharmaceutical compositions in accordance with the invention, and in particular those which are oral dosage forms, may be alcohol resistant.

The term "alcohol resistance" and its grammatical variations refer to the property of pharmaceutical compositions of the invention to release about the same or less amount of the pharmaceutically active agents in vitro, the in vitro release rate being tested in 500 or 900 ml of Simulated Gastric Fluid, pH 1.2 with up to 40% (v/v) ethanol using the Ph. Eur. Paddle method at 100 rpm at 37° C. compared to the in vitro release rate being tested in 500 or 900 ml of Simulated Gastric Fluid, pH 1.2 with up to 0% (v/v) ethanol using the Ph. Eur. Paddle method at 75 or 100 rpm at 37° C. The amount of dissolution liquid and the rotational speed of the paddle apparatus may depend on the amount of active agent tested. For example, pharmaceutical compositions comprising up to 16 mg hydromorphone HCl may be tested at 75 rpm in 500 ml dissolution liquid while higher dosage strengths may be tested at 100 rpm in 900 ml dissolution liquid.

Resistance to alcohol extraction can e.g. be tested by subjecting the formulation to Simulated Gastric Fluid (SGF), pH 1.2 with 40% ethanol. A typical manner in order to obtain "500 ml of Simulated Gastric Fluid (SGF), pH 1.2 with 40% ethanol" is by mixing 600 ml of SGF with 420 ml of 95% ethanol/water (which provides 400 ml of 100% ethanol) and taking 500 ml of the mixture. The effect of the additional 20 ml of water from the 95% ethanol will be minimal in the percentages of SGF and ethanol in the 500 ml mixture.

A typical manner in order to obtain 900 ml of Simulated Gastric Fluid (SGF), pH 1.2 with 40% ethanol" is by mixing 600 ml of SGF with 420 ml of 95% ethanol/water (which provides 400 ml of 100% ethanol) and taking 900 ml of the mixture. The effect of the additional 20 ml of water from the 95% ethanol will be minimal in the percentages of SGF and ethanol in the 100 ml mixture.

In certain embodiments, the present invention is directed to a prolonged release pharmaceutical composition comprising at least two pharmaceutically active agents, namely hydromorphone and naloxone or their pharmaceutically acceptable salts or derivatives and at least one prolonged release material being combined to form a prolonged release matrix; wherein the ratio of the amount of hydromorphone or a pharmaceutically acceptable salt or derivative thereof released after 0.5, 1 or 2 hours of in vitro dissolution of the dosage form in 500 or 900 ml of Simulated Gastric Fluid, pH 1.2 with up to 40% ethanol using the Ph. Eur. paddle method at 75 or 100 rpm at 37 C compared to the amount of hydromorphone or a pharmaceutically acceptable salt or derivative thereof released after 0.5, 1 or 2 hours in vitro dissolution of the dosage form in 500 or 900 ml of Simulated Gastric Fluid, pH 1.2 with 0% ethanol using the Ph. Eur. paddle method at 75 or 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less, and wherein the ratio of the amount of naloxone or a pharmaceutically acceptable salt or derivative thereof released after 0.5, 1 or 2 hours of in vitro dissolution of the dosage form in 500 or 900 ml of Simulated Gastric Fluid, pH 1.2 with up to 40% ethanol using the Ph. Eur. paddle method at 75 or 100 rpm at 37° C. compared to the amount of naloxone or a pharmaceutically acceptable salt or derivative thereof after 0.5, 1 or 2 hours in vitro dissolution of the dosage form in 500 or 900 ml of Simulated Gastric Fluid, pH 1.2 with 0% ethanol using the Ph. Eur. paddle method at 75 or 100 rpm at 37° C. is about 2:1 or less, about 1.5:1 or less, about 1:1 or less, about 1:1.2 or less, about 1:1.4 or less, about 1:1.6 or less, about 1:1.8 or less, about 1:2 or less, about 1:2.5 or less about 1:3 or less or about 1:5 or less. Preferably, the ratio is about 1:1 or less such as 1:1.5 or 1:2 for hydromorphone and/or naloxone.

The present invention as disclosed herein with respect to all aspects and embodiments is meant to encompass the use of any pharmaceutically acceptable salt or derivative of hydromorphone and naloxone. Any embodiment of the invention referring to hydromorphone and naloxone is also meant to refer to salts and preferably the hydrochloride salts thereof unless indicated otherwise.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

Pharmaceutically acceptable derivatives of hydromorphone and naloxone include esters thereof as well as modified forms such as glycosylated, pegylated or hesylated forms of hydromorphone and naloxone.

If in the following reference is made to a pharmaceutically active agent such as hydromorphone, this always also includes the reference to a pharmaceutically acceptable salt or derivative of the free base of this pharmaceutically active agent unless it is specifically indicated that the reference to the pharmaceutically active agent, such as use of the term "hydromorphone" should only refer to the free base.

The use of the hydrochloride salts of both hydromorphone and naloxone can be preferred.

In a preferred embodiment, the pharmaceutical dosage forms comprise hydromorphone or a pharmaceutically acceptable salt or derivative thereof or naloxone or a pharmaceutically acceptable salt or derivative thereof as the sole pharmaceutically active agents.

The pharmaceutical compositions may comprise about 1 to about 64 mg such as about 1 mg, about 2 mg, about 4 mg, about 8 mg, about 12 mg, about 16 mg, about 24 mg, about 32 mg, about 40 mg, about 48 mg or about 64 mg hydromorphone hydrochloride or equimolar amounts of any other pharmaceutically acceptable salt or derivative including but not limited to hydrates and solvates or of the free base. Where reference is made to amounts of hydromorphone hydrochloride this relates to anhydrous hydromorphone hydrochloride. If a hydrated version of hydromorphone hydrochloride is used, this will be used in an amount equivalent to the afore-mentioned amounts of anhydrous hydromorphone hydrochloride.

The pharmaceutical compositions may comprise about 1 to about 256 mg, such as about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride or equimolar amounts of any other pharmaceutically acceptable salt, derivative or form including but not limited to hydrates and solvates or of the free base. Where reference is made to amounts of naloxone hydrochloride this relates to anhydrous naloxone hydrochloride. If a hydrated version of naloxone hydrochloride is used, this will be used in an amount equivalent to the afore-mentioned amounts of anhydrous naloxone hydrochloride.

In some embodiments, the present invention is directed to a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone or a pharmaceutically acceptable salt or derivative thereof and/or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

- at 1 h: 25 to 55% by weight of the pharmaceutically active agents,
- at 2 h: 45 to 75% by weight of the pharmaceutically active agents,
- at 3 h: 55 to 85% by weight of the pharmaceutically active agents,
- at 4 h: 60 to 90% by weight of the pharmaceutically active agents,
- at 6 h: 70 to 100% by weight of the pharmaceutically active agents,
- at 8 h: more than 85% by weight of the pharmaceutically active agents,
- at 10 h: more than 90% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

In some embodiments, the present invention is directed to a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone and/or a pharmaceutically acceptable salt or derivative thereof or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

- at 1 h: 30 to 50% by weight of the pharmaceutically active agents,
- at 2 h: 50 to 70% by weight of the pharmaceutically active agents,
- at 3 h: 60 to 80% by weight of the pharmaceutically active agents,
- at 4 h: 65 to 85% by weight of the pharmaceutically active agents,
- at 6 h: 75 to 95% by weight of the pharmaceutically active agents,
- at 8 h: more than 90% by weight of the pharmaceutically active agents,
- at 10 h: more than 95% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

In some embodiments, the present invention is directed to a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone or a pharmaceutically acceptable salt or derivative thereof and/or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

- at 1 h: 10 to 30% by weight of the pharmaceutically active agents,
- at 2 h: 34 to 54% by weight of the pharmaceutically active agents,
- at 3 h: 53 to 73% by weight of the pharmaceutically active agents,
- at 4 h: 65 to 85% by weight of the pharmaceutically active agents,
- at 6 h: 75 to 95% by weight of the pharmaceutically active agents,
- at 8 h: 80 to 100% by weight of the pharmaceutically active agents,
- at 10 h: more than 90% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

In some embodiments, the present invention is directed to a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone or a pharmaceutically acceptable salt or derivative thereof and/or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

- at 1 h: 5 to 45% by weight of the pharmaceutically active agents,
- at 2 h: 15 to 55% by weight of the pharmaceutically active agents,
- at 3 h: 30 to 70% by weight of the pharmaceutically active agents,
- at 4 h: 35 to 75% by weight of the pharmaceutically active agents,
- at 6 h: 40 to 80% by weight of the pharmaceutically active agents,
- at 8 h: 50 to 90% by weight of the pharmaceutically active agents,
- at 10 h: 60 to 100% by weight of the pharmaceutically active agents,
- at 12 h: 65 to 100% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

Preferably, the amount of the pharmaceutically active agents released in vitro in 500 or 900 ml of Simulated Gastric Fluid, pH 1.2 using the Ph. Eur. paddle method at 100 rpm at 37° C. is:

at 1 h: 8 to 42% by weight of the pharmaceutically active agents,
at 2 h: 18 to 52% by weight of the pharmaceutically active agents,
at 3 h: 33 to 67% by weight of the pharmaceutically active agents,
at 4 h: 38 to 72% by weight of the pharmaceutically active agents,
at 6 h: 43 to 77% by weight of the pharmaceutically active agents,
at 8 h: 53 to 87% by weight of the pharmaceutically active agents,
at 10 h: 63 to 97% by weight of the pharmaceutically active agents,
at 12 h: 73 to 100% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

More preferably, the amount of the pharmaceutically active agents released in vitro in 500 or 900 ml of Simulated Gastric Fluid, pH 1.2 using the Ph. Eur. paddle method at 100 rpm at 37° C. is:
at 1 h: 15 to 37% by weight of the pharmaceutically active agents,
at 2 h: 25 to 47% by weight of the pharmaceutically active agents,
at 3 h: 38 to 62% by weight of the pharmaceutically active agents,
at 4 h: 42 to 66% by weight of the pharmaceutically active agents,
at 6 h: 50 to 74% by weight of the pharmaceutically active agents,
at 8 h: 60 to 84% by weight of the pharmaceutically active agents,
at 10 h: 68 to 92% by weight of the pharmaceutically active agents,
at 12 h: 78 to 100% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

Even more preferably, the amount of the pharmaceutically active agents released in vitro in 500 or 900 ml of Simulated Gastric Fluid, pH 1.2 using the Ph. Eur. paddle method at 100 rpm at 37° C. is:
at 1 h: 19 to 33% by weight of the pharmaceutically active agents,
at 2 h: 29 to 43% by weight of the pharmaceutically active agents,
at 3 h: 43 to 47% by weight of the pharmaceutically active agents,
at 4 h: 47 to 61% by weight of the pharmaceutically active agents,
at 6 h: 55 to 69% by weight of the pharmaceutically active agents,
at 8 h: 65 to 79% by weight of the pharmaceutically active agents,
at 10 h: 73 to 87% by weight of the pharmaceutically active agents,
at 12 h: 83 to 100% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

As mentioned above, in a first aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition provides alcohol resistance.

It will be described below how prolonged release pharmaceutical compositions of hydromorphone and naloxone providing alcohol resistance and the above mentioned release properties can be manufactured.

In a second aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) hydromorphone or a pharmaceutically acceptable salt or derivative thereof and naloxone or a pharmaceutically acceptable salt or derivative thereof are present in the pharmaceutical composition in a weight ratio in a range of about 2:1 to about 1:3, preferably of about 2:1, about 1:1, about 1:2 or about 1:3.

As mentioned above, in a third aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions releases the pharmaceutically active agents with substantially the same release rate as before subjecting the pharmaceutical composition to stressed conditions.

Storage under stressed conditions in the context of the present invention means that a pharmaceutical composition is subjected to increased temperature and/or relative humidity (RH) for prolonged periods of time. For example, typical stressed conditions refer to storage over at least one, two, three, four, five, six, twelfth or eighteen months at 25° C. and 60% RH. Other stressed conditions refer to storage over at least one, two, three, four, five, six or twelfth months at 30° C. and 65% RH Other stressed conditions refer to storage over at least one, two, three, four, five or six months at 40° C. and 75% RH.

Such stressed storage conditions are used to determine whether a pharmaceutical composition has a shelf life sufficient for long time storage under conditions as they are common in patients' households without negative effects on its safety and efficacy. Such negative effects may include that the in-vitro release rates change over time so that the efficacy of the composition is affected as different amounts of actives are released after administration. Similarly, negative effects may also result from degradation of the pharmaceutically active agents which may either decrease the overall amount of functional pharmaceutically active agent or lead to formation of toxic by-products.

If changes in the in vitro release profile or with respect to the amount of the active agent(s) of a pharmaceutical composition are observed after storage under stressed conditions, this may be indicative of stability problems. If such changes are not observed, this means vice versa that the pharmaceutical composition is storage stable.

The above mentioned stressed storage conditions can be used to estimate whether a pharmaceutical dosage will have a shelf life of at least about 12 months, at least about 18 months, at least about 24 months or at least about 36 months. Usually a shelf life of 18 months or more may be desirable as this is usually better compatible with e.g. supply of excipients, actives etc. for manufacturing purposes. If a pharmaceutical composition is storage stable, i.e. has essentially the same release rate after storage over at least one, two, three, four, five or more months at 25° C. and 60% RH, this will be usually indicative of shelf life of at least about 12 months. If a pharmaceutical composition is storage stable, i.e. has essentially the same release rate after storage over at least one, two, three, four, five or more months at 30° C. and 65% RH, this will be usually indicative of shelf life of at least about 18 months. If a pharmaceutical composition is storage stable, i.e. has essentially the same release rate after storage over at least one, two, three, four, five or more months at 40° C. and 75% RH, this will be usually indicative of a shelf life of at least about 24 months such as 36 months.

The term "substantially the same release rate" refers to the situation where the in vitro release rate for a pharmaceutical composition which has been subjected to stressed conditions is compared to a reference composition. The reference composition is an identical pharmaceutical composition which, however, has not been subjected to stressed conditions. If the in vitro release profile of the composition subjected to stressed conditions does not deviate by more than about 20%, preferably by no more than about 15%, more preferably by no more than 10% and even more preferably by no more than about 5% from the in vitro release profile of the reference composition, the in-vitro release rate is considered to be substantially the same.

In one embodiment of this third aspect, the present invention relates to an oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 25° C. at 60% relative humidity for at least one month releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 25° C. at 60% relative humidity for at least two months releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release matrix material;
b) at least hydromorphone or a pharmaceutically acceptable salt or derivative thereof and naloxone or a pharmaceutically acceptable salt or derivative thereof; and wherein
c) the pharmaceutical composition after storage at 25° C. at 60% relative humidity for at least five months releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 30° C. at 65% relative humidity for at least one month releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 30° C. at 65% relative humidity for at least two months releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release matrix material;
b) at least hydromorphone or a pharmaceutically acceptable salt or derivative thereof and naloxone or a pharmaceutically acceptable salt or derivative thereof; and wherein
c) the pharmaceutical composition after storage at 30° C. at 65% relative humidity for at least five months releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 40° C. at 75% relative humidity for at least one month releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 40° C. at 75% relative humidity for at least two months releases the pharmaceutically active agents with substantially the same release rate as before subjecting the pharmaceutical composition to stressed conditions.

In one embodiment of this third aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage at 40° C. at 75% relative humidity for at least five months releases the pharmaceutically active agents with substantially the same release rate as before subjecting the pharmaceutical composition to stressed conditions.

In a fourth aspect, the present invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions, preferably at 25° C. at 60% relative humidity for at least five months, has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or related to naloxone or a pharmaceutically acceptable salt or derivative thereof.

Stressed conditions are the same as mentioned above.

The term "hydromorphone and/or naloxone related substances" or the like refers to substances that arise from chemical reactions of hydromorphone or naloxone, pharmaceutically acceptable salts and derivatives thereof such as e.g. degradation. These substances can be distinguished as known hydromorphone related substances where the identity of the substance and its origin is known, as known naloxone related substances where the identity of the substance and its origin is known, and as unknown substances. For unknown substances, their identity is not known. However, it is assumed that they arise from hydromorphone and/or naloxone, pharmaceutically acceptable salts and derivatives thereof. It is to be understood that the term "hydromorphone and naloxone related substances" includes the sum of known hydromorphone related substances, known naloxone related substances and unknown substances and is thus equivalent to the term "total hydromorphone and naloxone related substances".

Terms like "less than about 4% of substances related to hydromorphone and naloxone, or to pharmaceutically acceptable salts or derivatives thereof" or "less than about 3% of substances related to hydromorphone and naloxone or to pharmaceutically acceptable salts or derivatives thereof" etc. indicate that the amount of total substances as described in the preceding paragraph is less than e.g. 4% or 3% by weight based on the total amount of the active ingredient which is present in lower amounts (i.e. hydromorphone or naloxone), or a pharmaceutically acceptable salt or derivative thereof which is present in the pharmaceutical composition in the lower amount. Thus, if a pharmaceutical composition comprises hydromorphone HCl and naloxone HCl in 1:2 ratio by weight, the amount of total substances is calculated from the sum of known hydromorphone HCl related substances, known naloxone HCl related substances and unknown substances which is then referenced to the amount of hydromorphone HCl. If a pharmaceutical composition comprises hydromorphone HCl and naloxone HCl in 2:1 ratio by weight, the amount of total substances is calculated from the sum of known hydromorphone HCl related substances, known naloxone HCl related substances and unknown substances which is then referenced to the amount of naloxone HCl.

"Known hydromorphone related substances" include hydromorphone n-oxide, noroxymorphone, pseudohydromorphone.

"Known naloxone related substances" include noroxymorphone, 10a-hydroxynaloxon, 7,8-didehydronaloxon, pseudonaloxon, 3-o-allylnaloxon.

Terms like "less than 4% of known substances related to hydromorphone, or to pharmaceutically acceptable salts or derivatives thereof" or "less than 3% of known substances related to hydromorphone, or to pharmaceutically acceptable salts or derivatives thereof" etc. indicate that the amount of known hydromorphone related substances is less than e.g. 4% or 3% of known hydromorphone related substance by weight based on the total amount of hydromorphone, or a pharmaceutically acceptable salt or derivative thereof in the composition.

Terms like "less than 4% of known substances related to naloxone, or to pharmaceutically acceptable salts or derivatives thereof" or "less than 3% of known substances related to naloxone, or to pharmaceutically acceptable salts or derivatives thereof" etc. indicate that the amount of known naloxone related substances is less than e.g. 4% or 3.0% of known naloxone related substance by weight based on the total amount of naloxone, or a pharmaceutically acceptable salt or derivative thereof in the composition.

In order to assess stability one may subject a pharmaceutical composition to stressed conditions as mentioned above and determine the amount of total hydromorphone and/or naloxone related substances. One then determines the amount of total hydromorphone and/or naloxone related substances for an identical pharmaceutical composition which has not been subjected to stressed conditions. This composition is considered to be a reference composition. The detection of "total hydromorphone related and/or naloxone substances" is typically performed by HPLC analysis using e.g. CAT columns. The amount of the substances including the amount of unknown substances is then determined by calculating the area under the respective peaks in the chromatogram. The identity of substances can be determined by doing the same analysis with pure known reference substances. In a further aspect the present invention aims at providing pharmaceutical compositions which after storage under stressed conditions have less than 4%, less than 3%, less than 2%, less than 1%, less than 0.5%, less than 0.2% or even less than 0.1% of total substances related to hydromorphone or a pharmaceutically acceptable salt or derivative thereof and/or related to naloxone or a pharmaceutically acceptable salt or derivative thereof.

In a further aspect the present invention aims at providing pharmaceutical compositions which after storage under stressed conditions have less than 1% such as less than 0.5%, less than 0.4%, less than 0.3%, less than 0.2%, less than 0.1% or even less than 0.05% of known substances related to hydromorphone or a pharmaceutically acceptable salt or derivative thereof and less than 1% such as less than 0.5% of known substances related to naloxone or a pharmaceutically acceptable salt or derivative thereof.

Stressed storage conditions may be the same as mentioned above. Thus typical stressed conditions may refer to storage over at least one, two, three, four, five or six months at 25° C. and 60% RH, at 30° C. and 65% RH or at 40° C. and 75% RH.

A pharmaceutical composition will thus be considered to be stable if after subjecting it to stressed conditions, it has no more than about 4% such as no more than about 3%, preferably no more than about 2%, more preferably no more than about 1% and even more preferably no more than about 0.5% of hydromorphone and/or naloxone related substances.

In one embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 25° C. and 60% relative humidity for at least one month has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 25° C. and 60% relative humidity for at least two months has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In yet another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 25° C. and 60% relative humidity for at least five months has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In one embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 30° C. and 65% relative humidity for at least one month has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 30° C. and 65% relative humidity for at least two months has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In yet another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 30° C. and 65% relative humidity for at least five months has less than about 4.0% such as less than about 3.0%, preferably less than about 2.0% and more preferably less than about 1% of total substances, less than about 0.5% or even less than about 0.2% related to hydromorphone or a pharmaceutically acceptable salt or derivative thereof and/or to naloxone or a pharmaceutically acceptable salt or derivative thereof.

In a further embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 40° C. and 70% relative humidity for at least one month has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In one embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 40° C. and 70% relative humidity for at least two months has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In one embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 40° C. and 70% relative humidity for at least five months has less than about 4.0% such as less than about 3.0%, preferably less than about 2.0% and more preferably less than about 1%, less than about 0.5% or even less than about 0.2% of total substances related to hydromorphone or a pharmaceutically acceptable salt or derivative thereof and/or to naloxone or a pharmaceutically acceptable salt or derivative thereof.

In one embodiment of this fourth aspect, the invention relates to an oral prolonged release pharmaceutical composition comprising at least:
a. at least one prolonged release material;
b. at least hydromorphone or a pharmaceutically acceptable salt or derivative thereof and naloxone or a pharmaceutically acceptable salt or derivative thereof, and wherein
c. the pharmaceutical composition after storage at 25° C. and 60% relative humidity for at least one month has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 25° C. and 60% relative humidity for at least two months has less than about 1% such as less than about 0.5%, 0.4%, 0.3%, 0.2%, 0.1% or even less than about 0.05% of known substances related to hydromorphone or a pharmaceutically acceptable salt or derivative thereof and less than even less than about 0.05% of known substances related to naloxone or a pharmaceutically acceptable salt or derivative thereof.

In yet another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 25° C. and 60% relative humidity for at least five months has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In one embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 30° C. and 65% relative humidity for at least one month has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In another embodiment of this fourth aspect, the invention relates to an oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition after storage at 30° C. and 65% relative humidity for at least two months has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In yet another embodiment of this fourth aspect, the invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof, and wherein
 c) the pharmaceutical composition after storage at 30° C. and 65% relative humidity for at least five months has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In a further embodiment of this fourth aspect, the invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof, and wherein
 c) the pharmaceutical composition after storage at 40° C. and 70% relative humidity for at least one month has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In one embodiment of this fourth aspect, the invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof, and wherein
 c) the pharmaceutical composition after storage at 40° C. and 70% relative humidity for at least two months has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

In one embodiment of this fourth aspect, the invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof, and wherein
 c) the pharmaceutical composition after storage at 40° C. and 70% relative humidity for at least five months has less than about 1% such as less than about 0.5%, 0.4%, 0.3%, 0.2%, 0.1% or even less than about 0.05% of known substances related to hydromorphone or a pharmaceutically acceptable salt or derivative thereof and less than about 1% such as less than about 0.5%, 0.4%, 0.3%, 0.2%, 0.1% or even less than about 0.05% of known substances related to naloxone or a pharmaceutically acceptable salt or derivative thereof.

It will be described below how prolonged release pharmaceutical compositions of hydromorphone and naloxone being stable can be manufactured. It will be apparent from this description that selection of anhydrous diluents and the choice of lubricant may be a means to positively influence stability. Heat treatment may improve physical stability such as robustness and hardness.

As mentioned above, in a fifth aspect the present invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof, and wherein
 c) the prolonged release pharmaceutical composition is heat treated.

In a first variation to this fifth aspect the present invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof,
 c) wherein the at least one prolonged release material and hydromorphone or a pharmaceutically acceptable salt or derivative thereof and naloxone or a pharmaceutically acceptable salt or derivative thereof are combined such that a prolonged release matrix is formed; and
 d) wherein the prolonged release pharmaceutical composition is heat treated.

In a second variation to this fifth aspect the present invention relates to an oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof;
 c) wherein the at least one prolonged release material, hydromorphone or a pharmaceutically acceptable salt or derivative thereof and naloxone or a pharmaceutically acceptable salt or derivative thereof are combined such that a prolonged release matrix is formed;
 d) wherein the prolonged release matrix is heat treated;
 e) wherein at least one prolonged release material is applied in the form of a prolonged release coating which is disposed on the prolonged release matrix; and
 f) wherein the composition is optionally cured.

The prolonged release coating may either be disposed on each prolonged release matrix if the prolonged release matrix is manufactured in the form of multi-particulates such as granules or it may be disposed on the formulation comprising the prolonged release matrix if e.g. prolonged release matrix multi-particulates such as granules are compressed into a tablet. The coating will then be disposed on the monolithic formulation.

The above heat treated pharmaceutical compositions may be preferably provided in the form of multiparticulates or mini-tablets that are filled into capsules.

Heat treatment may be performed such that the hardness/breaking strength of the pharmaceutical composition is increased for the heat treated versus the non heat treated composition. By heat treating pharmaceutical compositions in accordance with the invention, one may thus obtain compositions with improved hardness/breaking strength proportional to the tablet weight, size and shape. Heat treatment may improve physical stability such as robustness and hardness and in some although not all cases also positively influence chemical stability. As will be shown below, heat treatment may have an effect on in vitro release properties. Thus, heat treatment may further decrease the in vitro release compared to a non-heat treated composition. However, after heat treatment for relatively short periods of time (e.g. 30 min at 55° C.) the in vitro release rate will not change any further upon further heat treatment, i.e. remains substantially the same. It is further observed that such heat treated compositions when being subjected to stressed conditions will have substantially the same in vitro release rate as the same heat treated composition which has not been subjected to stressed conditions. Similarly such heat treated compositions will have less than about 4% of total hydromorphone and/or naloxone related substances and less than about 1% of known hydromorphone or known naloxone-related substance upon storage under stressed conditions.

Heat treatment will positively effect physical stability as can be deduced from a reduced occurrence of e.g. cracks and improved intactness of the formulation. This should help to ensure a reproducible release behavior also in vivo settings as changes due to e.g. an altered surface which occur as a consequence of cracks will be minimized. Further, heat treatment in general improves the hardness of the formulation in case of a prolonged release matrix formulation by usually about 3 to about 7 kP such as about 6 kP to an overall value of about 10 to 15 about kP such as about 11 kP. Hardness is usually tested using a mechanical strength tester such as a Holland C50 tablet hardness tester. 10 tablets are tested to provide a mean value every 15-20 mins during the compression run.

The term "heat treatment" refers to a thermal treatment under either or both increased temperature for a prolonged period of time. Typically, heat treatment takes place at a temperature in the range of about 30° C. to about 95° C. and for a time in the range of about 10 min to about 3 hours. Typically heat treatment conditions may thus be treatment for at least about 15 min, at least about 30 min, at least about 45 min, at least about 60 min, at least about 75 min, at least about 90 min, at least about 120 min, at least about 150 min, at least about 180 min or at least about 240 min at about at least 30° C., at about at least 40° C., at about at least 50° C., at about at least 60° C. or about at least 80° C. at ambient humidity. Heat treatment conditions may be selected according to the specific prolonged release matrix materials being used. In general the temperature will be around the melting and/or softening temperature of the prolonged release matrix materials being used. Such conditions may thus ensure that the prolonged release matrix materials are sufficiently soft to mobilise and to fill pores in the prolonged release matrix and/or e.g. compressed granules. In case of formulations using e.g. hydrophobic polymers such as ethyl cellulose and fatty alcohols such as stearyl or cetostearyl alcohol, a temperature of about 55° C. may be appropriate. In general, heat treatment for at least 30 min at 55° C. may be sufficient to ensure physical stability.

Heat treatment can be performed in a convection oven, in an open oven, under vacuum, in the coating drum using conventional heat, microwave and any other sources of heat. Heat treatment in a coating drum can be preferred. If the pharmaceutical compositions comprise a prolonged release coating either alone or in addition to a controlled release matrix, heat treatment of such prolonged release coatings is also designated as curing which helps coalescence of e.g. polymer coatings.

Prolonged release pharmaceutical compositions in accordance with some aspects of the invention may comprise a prolonged release matrix and/or coating which ensures prolonged release of the active ingredients and/or they may alternatively rely on a coating for imparting controlled release properties. In case of a prolonged release coating, the actives may be disposed on bead-like structures such as non pareil beads or granules or they may be incorporated into extruded granules or spheroids which as such do not provide prolonged release. The prolonged release coating is then layered thereon.

If a prolonged release coating is used it may be layered on individual prolonged release matrices such as granules or mini-tablets or it may layered on a monolithic formulation such as tablets or mini-tablets which are obtained by compressing prolonged release matrix granules.

If prolonged release coating is used the prolonged release composition may be optionally cured in order to enhance coalescence of the coating and thus to improve stability and intactness of the coating. The curing conditions may be the same as described above for coatings. Curing can further slow down the release properties. A curing step of about 20 minutes to 30 minutes at about 50° to 100° may be sufficient to slow down the release such that it won't substantially changes after storage under stressed conditions as the coating's properties will not substantially change anymore.

Pharmaceutical compositions in accordance with the invention may also comprise a prolonged release matrix with one or more prolonged release coatings thereon.

In addition prolonged release compositions comprising a prolonged release matrix or prolonged release coating may comprise e.g. a fraction of at least one or both of the pharmaceutically active agents in immediate release form. Such an immediate release phase which may account for up to 30% of the overall amount of the pharmaceutically active agent(s) being present in the composition can ensure an early onset of therapeutic efficacy.

The prolonged release compositions in accordance with the invention may be formulated into different dosage forms. For example, prolonged release compositions may take the form of tablets or mini-tablets. Tablets may be a monolithic tablet comprising e.g. a continuous prolonged release matrix. However, tablets or mini-tablets may be also be made from multiparticulates which are compressed into tablets. Such multiparticulates may e.g. comprise a prolonged release matrix optionally with an immediate release phase or active loaded beads with a prolonged release coating and optionally an immediate release phase thereon. The dosage form may also take the form of such multiparticulates, e.g. granules or mini-tablets which may be filled into a capsule.

The in vitro release rates of the prolonged release pharmaceutical compositions will be chosen such that a therapeutic efficacy in vivo is achieved over preferably at least twelve hours and in some instance even up to twenty four hours. Such compositions may be described as "twice a day" or "once a day" formulations as they may be administered on such a regimen.

A preferred embodiment of all embodiments and aspects as described above (in particular of the embodiments of the first, second, third, fourth and fifth aspect of the invention), the pharmaceutical compositions may comprise a prolonged release matrix and a prolonged release coating. These pharmaceutical compositions according to the first to fifth aspect may comprise hydromorphone and naloxone or the pharmaceutically acceptable salt or derivatives thereof in the above mentioned ratios and amounts. In the embodiments of the above mentioned aspects of the invention, hydromorphone or a pharmaceutically acceptable salt or derivative thereof and naloxone or a pharmaceutically acceptable salt or derivative thereof may thus be combined with a prolonged release material such that a prolonged release matrix is formed on which a prolonged release coating is then disposed. The prolonged release coating may be disposed on individual prolonged release matrix formulations so that a multiparticulate formulation is obtained. These multi-particulates may be directly filled into capsules or blended with other excipients to obtain a dosage form. In other embodiments, the prolonged release matrix formulation may take the form of e.g. granules which are compressed into mini-tablets or a monolithic dosage from such as tablets on which the prolonged release coating is then disposed. The manufacture of the prolonged release matrix may preferably be undertaken using an anhydrous method as described below. Manufacturing a prolonged release matrix in an anhydrous manner will have a beneficial effect on chemical stability as expressed e.g. by a substantially same in vitro release profile after storage under stressed conditions. Heat treatment will beneficially influence physical stability. A multiparticulate nature may have positive effects of food effects upon administration.

The prolonged release material may be any material that is known to be capable of imparting controlled release properties on the active agent when being formulated into a prolonged release matrix.

Such materials may be hydrophilic and/or hydrophobic materials such as gums, cellulose ethers, acrylic polymers, protein-derived materials etc.

Prolonged materials may also include fatty acids, fatty alcohols, glyceryl esters of fatty acids, polyethylene glycols, mineral and oils and waxes. Fatty acids and fatty alcohols preferable are those with a $C_{10}$ to $C_{30}$ chain, preferably with a $C_{12}$ to $C_{24}$ chain and more preferably with a $C_{14}$ to $C_{20}$ chain or a $C_{16}$ to $C_{20}$ chain. Materials such as stearyl alcohol, cetostearyl alcohol, cetyl alcohol, myristyl alcohol and polyalkylene glycols may be preferred. Waxes may be selected from natural and synthetic waxes such as beeswax, carnauba wax. Oils may be vegetable oils and include for example castor oil.

The prolonged release matrix materials which may be considered in the context of the present invention may also be selected from cellulose ethers.

The term "cellulose ethers" comprises cellulose-derived polymers derivatized with at least alkyl and/or hydroxyalkyl groups which may be hydrophilic or hydrophobic.

For example, the prolonged release matrix material may be a hydrophilic hydroxy alkyl cellulose such as a hydroxy (C1-C6)alkyl celluloses such as hydroxypropyl cellulose, hydroxypropylmethyl cellulose and particularly preferably hydroxyethyl cellulose.

Examples of hydrophobic cellulose ethers include e.g. ethyl cellulose. The use of ethyl cellulose may be preferred. Hydrophobic cellulose ethers such as ethyl cellulose may be particularly suitable for imparting alcohol resistance to pharmaceutical compositions.

A particularly suitable material for prolonged release matrix formulations in accordance with the present invention may be selected from the group of acrylic resins. Such acrylic resins may be made from (meth)acrylic acid (co) polymers.

There are various types of (meth)acrylic acid (co)polymers available which may be characterised according to the nature of their residues such as neutral (meth)acrylic acid (co)polymers, (meth)acrylic acid (co)polymers with anionic residues or (meth)acrylic acid ester copolymers with cationic residues.

Neutral (meth)acrylic acid (co)polymers include polymers having 95 to 100% by weight of polymerised monomers having neutral residues. Monomers with neutral residues can be $C_1$-$C_4$ alkyl esters of acrylic or methacrylic acid such as methylmethacrylate, ethylmethacrylate, butylmethacrylate, methylacrylate, ethylacrylate and butylacrylate. For example, neutral (meth)acrylic acid (co)polymers may comprise 20 to 40% by weight ethylacrylate and 60 to 80% by weight methylmethacrylate. Such polymers are e.g. available under the trade name Eudragit® NE which is a copolymer of 30% by weight ethylacrylate and 70% by weight methylmethacrylate. This polymer is usually provided in the form of a 30% or 40% aqueous dispersion (Eudragit® NE 30 D, Eudragit® NE 40 D or Eudragit® NM 30 D).

(Meth)acrylic acid (co)polymers with functional anionic residues may be (meth)acrylic acid (co)polymers having 25 to 95% by weight of radically polymerised $C_1$ to $C_4$ alkyl esters of acrylic or methacrylic acid and 5 to 75% by weight of methacrylate monomers with an anionic group in the alkyl residue. $C_1$ to $C_4$ alkyl esters of acrylic or methacrylic acid are again methylmethacrylate, ethyl methacrylate, butylmethacrylate, methylacrylate, ethylacrylate and butylacrylate. A (meth)acrylate monomer with an anionic group in the alkyl residue may be for example acrylic acid and preferably methacrylic acid. Such methacrylic acid copolymers with an anionic functional group may comprise e.g. 40 to 60% by weight methacrylic acid and 60 to 40% by weight methylmethacrylate or 60 to 40% by weight ethyl acrylate. These types of polymers are available as Eudragit® L100/ Eudragit® L 12.5 or Eudragit® L 100-55/Eudragit® L 30 D-55, respectively.

For example, Eudragit® L 100 is a copolymer of 50% by weight methylmethacrylate and 50% by weight methacrylic acid. It is also provided as a 12.5% solution (Eudragit® L 12.5). Eudragit® L 100-55 is a copolymer of 50% by weight ethylacrylate and 50% by weight methacrylic acid. It is also provided as 30% dispersion (Eudragit® L 30 D-55).

(Meth)acrylic acid (co)polymers with an anionic functional group may also comprise 20 to 40% by weight methacrylic acid and 80 to 60% by weight methylmethacrylate. These types of polymers are usually available under the trade name Eudragit® S. It is also provided as a 12.5% solution (Eudragit® S 12.5). Another type of methacrylic acid copolymers with an anionic functional group is available under the trade name Eudragit® FS which typically comprises 10 to 30% by weight methylmethacrylate, 50 to 70% by weight methylacrylate and 5 to 15% by weight methacrylic acid. Thus, Eudragit®FS may be a polymer of 25% by weight methylmethacrylate, 65% by weight methylacrylate and 10% by weight methacrylic acid. It is usually provided as 30% dispersion (Eudragit® FS 30 D).

(Meth)acrylic acid (co)polymers with functional cationic groups may be methacrylic acid copolymers with tertiary amino groups. Such polymers may comprise 30% to 80% by weight of radically polymerised $C_1$-$C_4$ alkyl esters of acrylic acid or methacrylic acid and 70 to 20% by weight methacrylate monomers with a tertiary amino group in the alkyl rest.

Suitable monomers with a functional tertiary amino group are disclosed e.g. in U.S. Pat. No. 4,705,695, column 3, line 64 to column 4, line 13. They include for example dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethylpropylmethacrylate, (3-diethylamino-2,2-dimethyl) propyl acrylate and diethylamino-2,2-dimethylpropylmethacrylate. Particularly suitable is dimethylaminoethyl methacrylate. The amount of monomers with a tertiary amino group in the copolymer may vary between 20 to 70%, between 40 to 60%. The amount of $C_1$ to $C_4$ alkyl esters of acrylic or methacrylic acid may be within 70 to 30% by weight. $C_1$ to $C_4$ alcohol esters of acrylic or methacrylic acid include methylmethacrylate, ethylmethacrylate, butylmethacrylate, methylacrylate, ethylacrylate and butylacrylate. A common (meth)acrylic acid (co)polymer with a tertiary amino group may comprise 20 to 30% by weight methylmethacrylate, 20 to 30% by weight butylmethacrylate and 60 to 40% by weight dimethylaminoethyl methacrylate. For example the commercially available Eudragit® E 100 comprises 25% by weight methylmethacrylate, 25% by weight butylmethacrylate and 50% by weight dimethylaminoethyl methacrylate. Another common commercially available polymer, Eudragit®E PO comprises copolymers of methylmethacrylate, butylmethacrylate and dimethylaminoethyl methacrylate in a ratio of 25:25:50.

Another type of (meth)acrylic acid (co)polymers with functional cationic groups is (meth)acrylic acid (co)polymers with a quaternary amino group. This type of (meth) acrylic acid (co)polymers typically comprises 50 to 70% of radically polymerised methylmethacrylate, 20 to 40% by weight of ethylacrylate and 12 to 2% by weight of 2-trimethylammoniumethyl methacrylate chloride. Such polymers are e.g. available under the trade names Eudragit® RS or Eudragit® RL.

For example, Eudragit® RS comprises radically polymerised units of 65% by weight methylmethacrylate, 30% by weight ethylacrylate and 5% by weight 2-trimethylammoniumethyl methacrylate chloride. Eudragit® RL comprises radically polymerised units of 60% by weight methylmethacrylate, 30% by weight ethylacrylate and 10% by weight 2-trimethylammoniumethyl methacrylate chloride.

Prolonged release matrix materials which are particularly suitable for the present invention are e.g. the neutral (meth) acrylic acid (co)polymers or the (meth)acrylic acid (co) polymers with anionic functional groups. One may for example use mixtures of these types of polymers.

For example, one may use Eudragit® NE as a neutral (meth)acrylic acid (co)polymer and Eudragit® RSPO as a (meth)acrylic acid (co)polymer with an anionic functional group. One may also use a mixture of these types of polymers.

However, one may also use a mixture of (meth)acrylic acid (co)polymers and other prolonged release matrix materials such as cellulose ethers. For example, one may use a mixture of a neutral (meth)acrylic acid (co)polymer and a hydrophobic cellulose ether. A particularly suitable example is the combination of a Eudragit® NE together with ethyl cellulose. Another prolonged release material which may be used for the present invention may be polymers such as polyethylene oxide.

As regards polyethylene oxides, particularly those polyethylene oxides with a molecular weight in the range of $1 \times 10^5$-$5 \times 10^5$ may be used.

Prolonged release materials which are particularly suitable for the present invention are e.g. the neutral (meth) acrylic acid (co)polymers or the (meth)acrylic acid (co) polymers with anionic functional groups. One may for example use mixtures of these types of polymers.

For example, one may use Eudragit® NE as a neutral (meth)acrylic acid (co)polymer and Eudragit® RSPO as a (meth)acrylic acid (co)polymer with an anionic functional group. One may also use a mixture of these types of polymers.

The use of (meth)acrylic acid (co)polymers can be particularly suitable for increasing hardness/breaking strength upon heat treatment.

However, one may also use a mixture of (meth)acrylic acid (co)polymers and other prolonged release matrix materials such as cellulose ethers. For example, one may use a mixture of a neutral (meth)acrylic acid (co)polymer and a hydrophobic cellulose ether. A particularly suitable example is the combination of a Eudragit® NE together with ethyl cellulose. Another example is a mixture of cellulose ether such as hydrophobic cellulose ethers (e.g. ethyl cellulose) with a fatty alcohol (e.g. stearyl alcohol). A mixture of (meth)acrylic acid (co)polymers such as neutral (meth) acrylic acid (co)polymer (e.g. Eudragit® NE) and cellulose ethers such as hydrophobic cellulose ethers (e.g. ethyl cellulose) may also comprise a fatty alcohol (such as stearyl or cetostearyl alcohol) as a further prolonged release matrix material. Such mixtures may allow combining beneficial characteristics such as alcohol resistance and increased hardness and improved stability upon heat treatment.

The amount of prolonged release material(s) in the prolonged release formulation may be of about 5 to 90% by weight, of about 10 to 70% by weight, of about 20 to 60% by weight, of about 20% to about 55% by weight, of about 25% to about 50% by weight, of about 25% to about 45% by weight and preferably of about 30 to about 40% by weight based on the weight of the pharmaceutical composition. The amount of prolonged release material that is incorporated into the composition can be one way of adjusting the prolonged release properties. For example, if the amount of prolonged release material is increased, the release can be further prolonged. The aforementioned amounts refer to the overall content of prolonged release materials in a pharmaceutical composition. These amounts may thus refer to a mixture of various prolonged release materials such as a neutral (meth)acrylic acid (co)polymer, a hydrophobic cellulose ether and/or a fatty alcohol.

If cellulose ether is among the prolonged release materials, it will typically be present in an amount of about 5% to about 50% by weight, of about 5% to about 45% by weight, of about 5% to about 40% by weight, of about 5% to about 35% by weight, of about 5% to about 30% by weight, of about 5% to about 25% by weight, of about 5% to about 20% by weight such as of about 5% by weight, of about 7% by weight, of about 10% by weight, of about 15% by weight, of about 18% by weight or of about 20% by weight based on the weight of the pharmaceutical composition.

If fatty alcohol is among the prolonged release materials, it will typically be present in an amount of about 5% to about 50% by weight, of about 5% to about 45% by weight, of about 5% to about 40% by weight, of about 5% to about 35% by weight, of about 10% to about 30% by weight, of about 10% to about 25% by weight such as of about 10% by weight, of about 15% by weight, of about 20% by weight or about 25% by weight based on the weight of the pharmaceutical composition.

If (meth)acrylic acid (co)polymer is among the prolonged release materials, it will typically be present in an amount of about 5% to about 50% by weight, of about 5% to about 45% by weight, of about 5% to about 40% by weight, of about 5% to about 35% by weight, of about 10% to about 30% by weight, of about 10% to about 25% by weight such as of about 10% by weight, of about 15% by weight, of about 20% by weight or about 25% by weight based on the weight of the pharmaceutical composition.

The pharmaceutical compositions in accordance with the invention may also include pharmaceutically acceptable excipients such fillers, lubricants, binders, release rate modifiers, anti-tacking agents etc.

Fillers which may also be designated as diluents may include e.g. lactose, preferably anhydrous lactose, glucose or saccharose, starches, their hydrolysates, microcrystalline cellulose, cellatose, sugar alcohols such as sorbitol or mannitol, polysoluble calcium salts like calcium hydrogen phosphate, dicalcium- or tricalcium phosphate and combinations of two or more of the above fillers.

It has been observed that the combination of hydromorphone and naloxone can be moisture sensitive in particular if cellulose ethers are used as prolonged release material. In view of this situation it can be preferred to use fillers which do not import moisture e.g. in the form of water. In preferred embodiments one may thus use anhydrous fillers such as anhydrous lactose.

Lubricants can include highly dispersed silica, talcum, corn starch, magnesium oxide and magnesium- or calcium stearate, fats like hydrated castor oil, sodium stearyl fumarate and combinations of two or more of the above lubricants.

It can be preferred to use a combination of magnesium stearate and talcum as lubricants. It has been found that if appropriate amounts of these lubricants are chosen, one can e.g. improve flow properties of granules used for compressing.

It thus can be preferred to use a lubricant amount of about 0.5% to about 4% by weight, of about 0.7% to about 3% by weight, of about 1% to about 2% by weight such as of about 1.0% by weight, of about 1.1% by weight, of about 1.2% by weight, of about 1.3% by weight, of about 1.4% by weight, of about 1.5% by weight, of about 1.6% by weight, of about 1.7% by weight, of about 1.8% by weight, of about 1.9% by weight or of about 2.0% by weight based on the weight of the pharmaceutical composition. An amount of about 0.75% to about 1.25% by weight based on the weight of the pharmaceutical composition can be preferred, particularly if magnesium stearate and talc are used. The aforementioned amounts refer to the amount of all lubricants (i.e. including mixtures) in the composition.

Binders can include hydroxypropyl cellulose (HPC), hydroxypropyl methyl cellulose, polyvinyl pyrollidone, carbopol, and combinations thereof.

It can be preferred to use HPC as a binder as this may positively influence the hardness of the tablets.

It thus can be preferred to use a binder amount of about 1% to about 10% by weight, of about 2% to about 9% by weight, of about 3% to about 7% by weight, of about 3% to about 6% by weight, of about 4% to about 5% by weight such as of about 4.0% by weight, of about 4.1% by weight, of about 4.2% by weight, of about 4.3% by weight, of about 4.4% by weight, of about 4.5% by weight, of about 4.6% by weight, of about 4.7% by weight, of about 4.8% by weight, of about 4.9% by weight or of about 5.0% by weight based on the weight of the pharmaceutical composition. An amount of about 4.4% to about 5.0% by weight based on the weight of the pharmaceutical composition can be preferred, particularly of HPC is used as binder. The aforementioned amounts refer to the amount of all binders (i.e. including mixtures) in the composition.

It can be preferred to not use povidone as a binder.

Release rate modifiers are pharmaceutically acceptable excipients which may be used to tune the release which otherwise would be obtained using the prolonged release materials, e.g. to accelerate the release or to further slow it down. Such release modifiers may be hydrophilic substances such as polyethyleneglycols, hydroxypropylmethylcellulose, hydroxyethylcellulose, and the like or hydrophobic substances such as oils, waxes and the like. Other release modifiers may include some the aforementioned (meth) acrylic acid(co)polymers such as polymers of the Eudragit® RLPO type or gums such as xanthan gum.

Release rate modifiers such as polymers of the Eudragit/® RLPO type, low molecular weight hydroxypropylmethylcellulose such Hypromellose K100M or xanthan gum may be preferred.

Such release rate modifiers may be present in an amount of about 1% to about 20% by weight, of about 2% to about 19% by weight, of about 3% to about 18% by weight, of about 4% to about 17% by weight, of about 5% to about 15% by weight such as of about 5% by weight, of about 6% by weight, of about 7% by weight, of about 8% by weight, of about 9% by weight, of about 10% by weight, of about 11% by weight, of about 12% by weight, of about 13% by weight, of about 14% by weight or of about 15% by weight based on the weight of the pharmaceutical composition. The aforementioned amounts refer to the amount of all release rate modifiers (i.e. including mixtures) in the composition.

It is to be understood that the functions of pharmaceutically acceptable excipients may be overlapping. For example, a spheronising agent such as microcrystalline cellulose can also be used as filler if appropriate amounts are chosen. Further, HPMC may not only act as release rate modifying agent but also as binder if e.g. used in prolonged release formulation with a coating.

Prolonged release coatings may be made from materials which are common in the art.

They may thus be selected from e.g. prolonged release materials selected e.g. from (i) an alkylcellulose; (ii) an acrylic polymer; (iii) polyvinylalcohol or (iv) mixtures thereof. Hydrophobic representatives of the afore-mentioned groups can be preferred. The coating may be applied in the form of an organic or aqueous solution or dispersion.

In some embodiments, the controlled release coating is derived from an aqueous dispersion of the hydrophobic controlled release material. The coated composition can then be cured.

In preferred embodiments, the controlled release coatings include a plasticizer such as those described herein below.

In certain embodiments, one may coat with an amount of coating material which is sufficient to obtain a weight gain level from about 2 to about 20%, e.g., about 2 to about 15% and preferably about 5 to about 10% such as 6%, 7%, 8% or 9% in order to obtain sufficiently prolong the release from the formulation.

Cellulosic materials and polymers, including alkyl celluloses are prolonged release materials well suited for coating substrates, e.g., beads, granules, tablets, etc. according to the invention. Simply by way of example, one preferred alkyl cellulosic polymer is ethyl cellulose One commercially available aqueous dispersion of ethyl cellulose is Aquacoat® such as Aquacoat® ECD30 (FMC Corp., Philadelphia, Pa., U.S.A.). Aquacoat is prepared by dissolving the ethyl cellulose in a water-immiscible organic solvent and then emulsifying the same in water in the presence of a surfactant and a stabilizer. After homogenization to generate submicron droplets, the organic solvent is evaporated under vacuum to form a pseudo latex.

Another aqueous dispersion of ethyl cellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In other of the present invention, the prolonged release coating material is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly (methacrylic acid anhydride) and glycidyl methacrylate copolymers.

In certain preferred embodiments, the acrylic polymer is comprised of one or more ammonium methacrylate copolymers Ammonium methacrylate copolymers are well known in the art, and are described as fully polymerized copolymers of acrylic and methacrylic acid esters with a low content of quaternary ammonium groups. Typical examples include Eudragit® RS30D which is a low permeability ammonium methacrylate polymer and Eudragit® RL30D which is a high permeability ammonium methacrylate polymer. Eudragit RL and Eudragit RS are water swellable, and the amount of water absorbed by these polymers is pH-dependent, however, dosage forms coated with Eudragit RL and RS are pH-independent.

The acrylic coatings may comprise a mixture of two acrylic resin lacquers commercially available from Rohm Pharma under the Trade names Eudragit® RL30D and Eudragit® RS30D, respectively. The Eudragit® RL/RS dispersions of the present invention may be mixed together in any desired ration in order to ultimately obtain a prolonged-release formulation having a desirable dissolution profile.

Other polymers which can be used as a prolonged release coating materials if they are applied at sufficient amounts are e.g. hydrophilic polymers such as hydroxypropylmethylcellulose.

The above mentioned coatings may also be applied in combination. Further it is possible to influence the release properties of a dosage form by increasing the amount of the coating material and thus the thickness of the coating.

In embodiments of the present invention where the coating comprises an aqueous dispersion of a hydrophobic controlled release material, the inclusion of an effective amount of a plasticizer in the aqueous dispersion of hydrophobic material may further improve the physical properties of the prolonged release coating. For example, because ethyl cellulose has a relatively high glass transition temperature and may not form flexible films under normal coating conditions, it can be preferred to incorporate a plasticizer into an ethyl cellulose coating containing prolonged release coating before using the same as a coating material. Generally, the amount of plasticizer included in a coating solution is based on the concentration of the film-former, e.g., most often from about 1 to about 50% by weight of the film-former.

Examples of suitable plasticizers for ethyl cellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin.

In the following it is described how a prolonged release matrices which may be used for all aspects and variations of the invention may be composed.

The invention for all its aspects and variations thus considers as a first option an oral prolonged release pharmaceutical composition comprising at least:
 a) at least one (meth)acrylic acid (co)polymer, preferably at least one neutral (meth)acrylic acid (co)polymer such as Eudragit® NE as prolonged release material;
 b) at least hydromorphone or a pharmaceutically acceptable salt or derivative thereof and naloxone or a pharmaceutically acceptable salt or derivative thereof, wherein
 c) the hydromorphone or a pharmaceutically acceptable salt or derivative thereof and naloxone or a pharmaceutically acceptable salt or derivative thereof is combined with said prolonged release material to form a prolonged release matrix.

The invention for all its aspects and variations thus considers as a second option an oral prolonged release pharmaceutical composition comprising at least:
 a) at least one cellulose ether, preferably at least one hydrophobic cellulose ether such as ethyl cellulose as prolonged release material;
 b) at least hydromorphone or a pharmaceutically acceptable salt or derivative thereof and naloxone or a pharmaceutically acceptable salt or derivative thereof, wherein
 c) the hydromorphone or a pharmaceutically acceptable salt or derivative thereof and naloxone or a pharmaceutically acceptable salt or derivative thereof is combined with said prolonged release material to form a prolonged release matrix.

The invention for all its aspects and variations thus considers as a third option an oral prolonged release pharmaceutical composition comprising at least:
 a) at least one fatty alcohol as prolonged release material;
 b) at least hydromorphone or a pharmaceutically acceptable salt or derivative thereof and naloxone or a pharmaceutically acceptable salt or derivative thereof, wherein
 c) the hydromorphone or a pharmaceutically acceptable salt or derivative thereof and naloxone or a pharmaceutically acceptable salt or derivative thereof are combined with said prolonged release material to form a prolonged release matrix.

The invention for all its aspects and variations thus considers as a fourth option an oral prolonged release pharmaceutical composition comprising at least:
  a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
  b) at least hydromorphone or a pharmaceutically acceptable salt or derivative thereof and naloxone or a pharmaceutically acceptable salt or derivative thereof, wherein
  c) the hydromorphone or a pharmaceutically acceptable salt or derivative thereof and naloxone or a pharmaceutically acceptable salt or derivative thereof are combined with said prolonged release materials to form a prolonged release matrix.

The invention for all its aspects and variations thus considers as a fifth option an oral prolonged release pharmaceutical composition comprising at least:
  a) at least one (meth)acrylic acid (co)polymer, preferably at least one neutral (meth)acrylic acid (co)polymer such as Eudragit® NE and at least one fatty alcohol as prolonged release materials;
  b) at least hydromorphone or a pharmaceutically acceptable salt or derivative thereof and naloxone or a pharmaceutically acceptable salt or derivative thereof, wherein
  c) the hydromorphone or a pharmaceutically acceptable salt or derivative thereof and naloxone or a pharmaceutically acceptable salt or derivative thereof are combined with said prolonged release materials to form a prolonged release matrix.

The invention for all its aspects and variations thus considers as a sixth option which may be particularly preferred, an oral prolonged release pharmaceutical composition comprising at least:
  a) at least one cellulose ether, preferably at least one hydrophobic cellulose ether such as ethyl cellulose and at least one fatty alcohol as prolonged release materials;
  b) at least hydromorphone or a pharmaceutically acceptable salt or derivative thereof and naloxone or a pharmaceutically acceptable salt or derivative thereof, wherein
  c) the hydromorphone or a pharmaceutically acceptable salt or derivative thereof and naloxone or a pharmaceutically acceptable salt or derivative thereof are combined with said prolonged release materials to form a prolonged release matrix.

The invention for all its aspects and variations thus considers as a seventh option an oral prolonged release pharmaceutical composition comprising at least:
  a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;
  b) at least hydromorphone or a pharmaceutically acceptable salt or derivative thereof and naloxone or a pharmaceutically acceptable salt or derivative thereof, wherein
  c) the hydromorphone or a pharmaceutically acceptable salt or derivative thereof and naloxone or a pharmaceutically acceptable salt or derivative thereof are combined with said prolonged release materials to form a prolonged release matrix.

The prolonged release materials may be used in the amounts mentioned above.

In a first embodiment of the first to seventh option, the pharmaceutical composition is heat treated as described above.

In addition or alternatively to this first embodiment of the first to seventh option, the pharmaceutical composition may comprise an anhydrous filler such as anhydrous lactose.

In addition or alternatively to this first and second embodiment of the first to seventh option, the pharmaceutical composition may comprise magnesium stearate and/or talc in the above mentioned amounts.

In addition or alternatively to this first, second and third embodiment of the first to seventh option, the pharmaceutical composition may comprise HPC in the above mentioned amounts.

In addition or alternatively to this first, second, third and fourth embodiment of the first to seventh option, the pharmaceutical composition may comprise HPC in the above mentioned amounts.

In addition or alternatively to this first, second, third, fourth and fifth embodiment of the first to seventh option, the pharmaceutical composition may comprise an additional prolonged release coating. Such a coating may comprise preferably ethyl cellulose as prolonged release coating material.

These pharmaceutical compositions according to the first to seventh option may comprise hydromorphone and naloxone or a pharmaceutically acceptable salt or derivatives thereof in the above mentioned ratios and amounts. They may further provide the above mentioned in vitro release data and alcohol resistance as described above. Further, these compositions may provide storage stability. They may also be of a multiparticulate nature. They may further provide the pharmacokinetic parameters as mentioned herein.

Of one attempts to realize specific in vitro release rates, one can use combinations of the above mentioned measures. For example, if the release from a prolonged release matrix is deemed too fast one may apply a prolonged release coating in addition. In addition or alternatively, one may add additional prolonged release matrix materials such as hydrophobic polymers, with ethyl cellulose being preferred and/or fatty alcohols to granules which already comprise a prolonged release matrix and to then compress these granules together with the additional prolonged release matrix materials into e.g. tablets. In a preferred embodiment, such prolonged release matrix formulations which are coated with such prolonged release matrix formulations and then are used as a multiparticulate formulation.

The pharmaceutical compositions in accordance with the invention as described herein may be formulated to provide a mean AUCt of about 1162 h*pg/ml to about 2241 h*pg/ml and preferably of about 1328 to about 2075 h*pg/ml per mg administered amount of hydromorphone and a mean Cmax of about 122 pg/ml to about 234 pg/ml and preferably of about 139 to about 218 pg/ml per mg administered amount of hydromorphone and mean tmax of about 1 h to about 4.5 h, preferably of about 1.5 h to about 4 h and more preferably of about 1.5 h to about 3 h. These values refer preferably to single dose administration to healthy subjects. Preferably, administration is in the fasted state. The mean values of Cmax, AUCt and tmax refer to the geometric mean.

The "Cmax value" indicates the maximum blood plasma concentration of the active agent hydromorphone.

The "tmax value" indicates the time point at which the Cmax value is reached. In other words, tmax is the time point of the maximum observed plasma concentration.

The "AUC (Area Under the Curve)" value corresponds to the area of the concentration curve. The AUC value is proportional to the amount of the active agent absorbed into the blood circulation in total and is hence a measure for the bioavailability.

The "AUCt value" is the value for the area under the plasma concentration-time curve from the time of administration to the last measurable concentration. AUCt values are usually calculated using the linear trapezoidal method.

If pharmacokinetic parameters such as mean $t_{max}$, $C_{max}$ and AUCt are measured for healthy subjects which may be healthy human, they are typically obtained by measuring the development of blood plasma values over time in a test population of approximately 16 to 24 healthy human subjects. Regulatory bodies such as the European Agency for the Evaluation of Medicinal Products (EMEA) or the Food and Drug Administration (FDA) will usually accept data obtained from e.g. 16 or 24 test persons. However, initial trials involving fewer participants such as 8 to 16 participants may also be acceptable.

The term "healthy" subjects in this context refers to a typical male or female of usually Caucasian origin with average values as regards height, weight and physiological parameters such as blood pressure etc. Healthy human subjects for the purposes of the present invention are selected according to inclusion and exclusion criteria which are based on and in accordance with recommendations of the International Conference for Harmonization of Clinical Trials (ICH). For the purposes of the present invention, healthy subjects may be identified according to the inclusion and exclusion criteria as outlaid in Example 7.

Thus, inclusion criteria comprise e.g. an age between ≥18 and ≤45 years; a BMI within the range 19-29 kg/m², and within the weight range 60-100 kg for males and 55-90 kg for females; that females must be non-nursing, non-pregnant, and provide a negative urine β-hCG pregnancy test within 24 hours before receiving the study medication; generally good health, evidenced by a lack of significantly abnormal findings on medical history, physical examination, clinical laboratory tests, vital signs, and ECG etc.

Exclusion criteria comprise e.g. exposure to any investigational drug or placebo within 3 months of the first dose of study medication, any significant illness within the 30 days before the first dose of study medication, any clinically significant abnormalities identified at prestudy screening for medical history, physical examination or laboratory analyses, use of any prescription medication (except HRT for postmenopausal females and contraceptive medication) in the 21 days, or over the counter medication including acid controllers, vitamins, herbal products and/or mineral supplements in the 7 days, before first dose of study medication, concurrent medical condition known to interfere with gastrointestinal drug absorption (e.g. delayed gastric emptying, mal absorption syndromes), distribution (e.g. obesity), metabolism or excretion (e.g. hepatitis, glomerulonephritis), history of or concurrent medical condition, which in the opinion of the investigator would compromise the ability of the subject to safely complete the study, history of seizure disorders for which subjects required pharmacologic treatment, current history of smoking more than 5 cigarettes a day, subjects with evidence of active or past history of substance or alcohol abuse according to DSM-IV criteria, subjects who reported regular consumption of 2 or more alcoholic drinks per day or have blood alcohol levels of ≥0.5% at screening, donation of more than 500 mL of blood or blood products or other major blood loss in the 3 months before first dose of study medication, any positive results in the prestudy screen for ethanol, opiates, barbiturates, amphetamines, cocaine metabolites, methadone, propoxyphene, phencyclidine, benzodiazepines, and cannabinoids in the specimen of urine collected at screening, known sensitivity to hydromorphone, naloxone, or related compounds etc. The afore-mentioned pharmacokinetic data may preferably be obtainable with a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone or a pharmaceutically acceptable salt or derivative thereof or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

at 1 h: 25 to 55% by weight of the pharmaceutically active agents,
at 2 h: 45 to 75% by weight of the pharmaceutically active agents,
at 3 h: 55 to 85% by weight of the pharmaceutically active agents,
at 4 h: 60 to 90% by weight of the pharmaceutically active agents,
at 6 h: 70 to 100% by weight of the pharmaceutically active agents,
at 8 h: more than 85% by weight of the pharmaceutically active agents,
at 10 h: more than 90% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

The afore-mentioned pharmacokinetic data may even more preferably be obtainable with a prolonged release pharmaceutical composition comprising at least hydromorphone or a pharmaceutically acceptable salt or derivative thereof or naloxone or a pharmaceutically acceptable salt or derivative thereof and at least one prolonged release material which is preferably combined with these pharmaceutically active agents to form a prolonged release matrix; wherein the amount of hydromorphone or a pharmaceutically acceptable salt or derivative thereof or naloxone or a pharmaceutically acceptable salt or derivative thereof released in vitro in 500 or 900 ml of Simulated Gastric Fluid, pH 1.2 using the Ph. Eur. paddle method at 100 rpm at 37° C. is:

at 1 h: 30 to 50% by weight of the pharmaceutically active agents,
at 2 h: 50 to 70% by weight of the pharmaceutically active agents,
at 3 h: 60 to 80% by weight of the pharmaceutically active agents,
at 4 h: 65 to 85% by weight of the pharmaceutically active agents,
at 6 h: 75 to 95% by weight of the pharmaceutically active agents, at 8 h: more than 90% by weight of the pharmaceutically active agents, at 10 h: more than 100% by weight of the pharmaceutically active agents.

The pharmaceutically active agents may preferably be hydromorphone HCl and naloxone HCl being preferred. The prolonged release pharmaceutical composition may comprise these actives in the above indicated amounts and weight ratio of about 2:1, about 1:1, about 1:2 or about 1:3. The composition may be alcohol resistant as described hereinafter.

Prolonged release pharmaceutical compositions as mentioned hereinafter can be obtained using a method of manufacturing comprising at least the steps of:

a) producing granules comprising at least one prolonged release material, at least hydromorphone or a pharmaceutically acceptable or derivative salt thereof and at least naloxone or a pharmaceutically acceptable salt or derivative thereof, b) optionally selecting granules of step a) of substantially uniform size;

c) optionally adding additional prolonged release materials;

d) compressing said granules of step a), step b) or step c) to obtain an oral prolonged release pharmaceutical composition in the form of a tablet, e) optionally heat treating said compressed granules of step d);

f) optionally disposing a prolonged release coatings either on the granules of step a), b) or c) or on the monolithic composition obtained in step d) or e);

g) optionally curing the obtained composition.

It is to be understood that at least the compression step c) produces an oral prolonged release pharmaceutical composition in the form of a tablet which comprises a prolonged release matrix. However, the granules obtained in step a) may also already comprise a prolonged release matrix.

Prolonged release pharmaceutical compositions as mentioned hereinafter can also be obtained using a method of manufacturing comprising at least the steps of:

a) producing granules comprising at least one prolonged release material, at least hydromorphone or a pharmaceutically acceptable or derivative salt thereof and at least naloxone or a pharmaceutically acceptable salt or derivative thereof, b) optionally selecting granules of step a) of substantially uniform size;

c) optionally heat treating said granules of step a) or step);

d) optionally disposing a prolonged release coatings either on the granules of step a), b) or c);

e) optionally curing the obtained composition.

The person skilled in the art is aware of different means and methods for producing granules according to step a).

In one embodiment, such granules may be produced by wet or dry granulation. Thus, for producing granules, step a) may comprise the following steps:

aa) blending a prolonged release material with at least hydromorphone or a pharmaceutically acceptable or derivative salt thereof and at least naloxone or a pharmaceutically acceptable salt or derivative thereof and optionally with a pharmaceutically acceptable excipient, ab) wet or dry granulating said blend of step aa) to obtain granules, and optionally spheronising them, ac) drying said granules of step ab).

The pharmaceutically acceptable excipients may include the fillers, binders, lubricants, release rate modifiers, spheronising agents, anti-tacking agents, etc. as mentioned above. However, some of these excipients such as e.g. lubricants may be added at a later stage (see below).

Different technology is available to obtain such granules. One may use e.g. drum granulation or fluidized bed granulation.

Alternatively and/or additionally granules according to step a) may be produced comprising the steps of:

aa) blending a prolonged release matrix material with at least hydromorphone or a pharmaceutically acceptable or derivative salt thereof and at least naloxone or a pharmaceutically acceptable salt or derivative thereof and optionally with a pharmaceutically acceptable excipient, ab) extruding said blend of step aa) to obtain granules, ac) drying said granules of step ab).

The pharmaceutically acceptable excipients may include the fillers, binders, lubricants, release rate modifiers, spheronising agents, anti-tacking agents, etc. as mentioned above. However, some of these excipients such as e.g. lubricants may be added at a later stage (see below).

Different extruder technology is available to obtain extruded granules. For example, one may use a single screw or twin screw extruder. For twin screw extruders, one may use counter-rotating or co-rotating screws having optionally paddle means.

As mentioned above, the granules which may be produced by wet granulation extrusion may be dried before being mixed with the at least one pharmaceutically active agent.

Typically, drying takes place at humidity in the range of about 0.5% to about 5.0% at a temperature in the range of about 20° C. to about 90° C. and for a time in the range of about 10 min to about 3 hours. Drying at ambient humidity at a temperature in the range of about 40° C. to about 90° C. and for a time in the range of about 15 min to about 2 hours can be preferred.

The granules may then be optionally screened in order to select granules of substantially uniform size. Selecting granules of substantially uniform size before compressing them may improve the prolonged release properties of the final prolonged release pharmaceutical composition as the active and the granules are then assumed to be more uniformly distributed which may prevent irregularities in the release profile. Granules for which at least about 70%, preferably at least about 80%, more preferably at least about 90% are of about the same mean size will typically be considered as being of substantially uniform size.

Preferably, granules are selected of a mean size in the range of about 100 μm to about 2 mm, more preferably in the range of about 100 μm to about 1 mm, and even more preferably in the range of about 100 μm to about 600 μm. Selection may be performed using a sieve with an appropriate mesh size.

In some embodiments the granules may be milled before selecting them for their size. Milling may both increase the yield of the selection step and improve the granules' suitability for the subsequent compression step. For milling one may use for example a rotary hammer mill or top/bottom driven conical mill.

Even though granules may be produced by wet granulation, anhydrous manufacturing steps and methods such as anhydrous extrusion may be preferred, at least where hydromorphone and naloxone or its pharmaceutically acceptable salts or derivatives thereof are to be included in a prolonged release matrix. The preference for anhydrous manufacturing steps and methods when making a prolonged release matrix is that this has a beneficial impact on the chemical stability of hydromorphone or naloxone or its pharmaceutically acceptable salts or derivatives. Once the active agents have been included in such a prolonged release matrix, the optional additional application of e.g. a prolonged release coating does not have be in an anhydrous manner. It is to be understood that the term "anhydrous manufacturing" indicates that the process that leads to a prolonged release matrix may be performed in the absence of substantial amounts of water. This does not mean that the components which are used do not comprise molecular bound water. Thus, even where the process is performed in an anhydrous manner such as extrusion, naloxone hydrochloride may e.g. be provided as a dihydrate and fillers such as lactose may be provided as lactose monohydrate even though anhydrous lactose can be preferred.

For compressing the pharmaceutically active agent(s) with the granules, one may use typical tabletting equipment such as Example Fette or Kilian press.

When compressing granules and active(s), one may also include pharmaceutically acceptable excipients as they are commonly used in the art. For example, one may add lubricants, anti-tacking agents, binders and the like. For lubricants, the use of magnesium stearate and/or talc in the aforementioned amounts can be of advantage.

As mentioned above, prolonged release pharmaceutical dosage forms in accordance with the invention may be additionally subjected to a heat treatment step as has been described above.

The prolonged release coating may be produced by methods common in the art such a fluidized bed spraying.

As described above, the invention relates in some embodiments to oral prolonged release pharmaceutical compositions comprising hydromorphone or a pharmaceutically acceptable salt or derivative thereof and naloxone or a pharmaceutically acceptable salt of derivative thereof comprising hydromorphone or a pharmaceutically acceptable salt or derivative thereof and naloxone or a pharmaceutically acceptable salt of derivative thereof in weight rations in a range of about 2:1 to about 1:3, preferably of about 2:1, 1:1, 1:2 or 1:3. It is to be understood that particularly for these embodiments, hydromorphone or a pharmaceutically acceptable salt or derivative thereof and naloxone of a pharmaceutically acceptable salt or derivative thereof can be comprised within distinct pharmaceutical compositions which can then be administered simultaneously or sequentially to provide the benefits of such a fixed ratio.

The invention is now illustrated with respect to specific examples. These examples are, however, not to be construed as limiting.

EXAMPLES

Example 1

Tablets of the composition as shown in Table 1 were manufactured.

|  | Tablets | | |
| --- | --- | --- | --- |
| Ingredient | F880/99 Amount (mg) | F880/105 Amount (mg) | F893/31 Amount (mg) |
| Hydromorphone HCl | 2.0 | 2.0 | 2.0 |
| Naloxone HCl | 4.0 | 4.0 | 4.0 |
| Stearyl alcohol | 25.0 | 25.0 | 25.0 |
| Ethyl cellulose N45 | 20.0 | 20.0 | — |
| Lactose anhydrous | 76.4 | 76.4 | 76.4 |
| Eudragit RSPO* | — | — | 20.0 |
| Sodium stearyl fumarate | 2.6 | 2.6 | 2.6 |
| Hypromellose K100M | 20.0 | — | 20.0 |
| Xanthan Gum 'extra' | — | 12.0 | — |
| Total | 150.0 | 142.0 | 150 |

*The amount indicated refers to the amount of solids used.

Hydromorphone HCl and naloxone HCl were mixed with lactose anhydrous, stearyl alcohol and either ethyl cellulose N45 or Eudragit RSPO as a prolonged release polymer in a double cone mixer for 10 min.

Subsequently the blend was melt extruded using a heated twin screw extruder.

The temperature profile for the extruder was as follows:

| Extruder type | twin screw |
| --- | --- |
| Heating zone 1 (feeding zone) | 25° C. |
| Heating zone 2 | 50-55° C. |
| Heating zone 3 | 73-83° C. |
| Heating zones 5-10 | 70-80° C. |
| Die head | 50-55 |

The feeder rate was 10-15 kg/h. The screw speed was set at 150-250 rpm. The die plate design allowed for multiple strand extrusion. Compressed air was used to cool the extruded strands on conveyor belt.

Subsequently, the strands were milled to obtain granules. For milling, a Retsch mill with a 1.25 mm screen was used. This gave a substantially unimodal size distribution of the granules mainly in the range 100 to 600 nm.

The granules were then blended with sodium stearyl fumarate which was included as a lubricant. In addition, Hypromellose K100M was included as a release modifier. These components were blended for an additional 5 min. The granules were then compressed into tablets using a Kilian press.

Tablets F880/99, F880/105 and F893/31 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release are indicated as percentage (based on the label content of active tested) in table 2.

TABLE 2

| | Tablets | | | | | |
|---|---|---|---|---|---|---|
| | F880/99 | | F880/105 | | F893/31 | |
| | Dissolution medium | | | | | |
| | 0.1N HCl pH 1.2 | | 0.1N HCl pH 1.2 | | 0.1N HCl pH 1.2 | |
| Active tested | Hm | Nal | Hm | Nal | Hm | Nal |
| 0.5 h | 25 | 24 | 29 | 28 | 25 | 23 |
| 1 h | 37 | 35 | 41 | 40 | 36 | 33 |
| 2 h | 55 | 53 | 59 | 56 | 53 | 49 |
| 3 h | 68 | 66 | 71 | 68 | 65 | 62 |
| 4 h | 78 | 77 | 79 | 77 | 75 | 71 |
| 5 h | 88 | 86 | 86 | 83 | 83 | 79 |
| 6 h | 94 | 92 | 91 | 88 | 89 | 85 |
| 7 h | 97 | 96 | 93 | 91 | 92 | 89 |
| 8 h | 99 | 97 | 96 | 94 | 95 | 92 |
| 9 h | 99 | 98 | 97 | 96 | 97 | 95 |
| 10 h | 99 | 98 | 98 | 97 | 97 | 96 |
| 11 h | 99 | 98 | 99 | 98 | 97 | 96 |
| 12 h | 99 | 98 | 99 | 98 | 97 | 96 |

Hm = hydromorphone HCl,
Nal = naloxone HCl,
0.1N HCl w/o 40% EtOH = 0.1N HCl pH 1.2 without 40% ethanol;
Values are averages of 6 measurements.

The tablets were further evaluated with respect to their alcohol resistance. To this end in vitro release rates were determined using the Ph. European paddle method at 75 rpm in 500 simulated gastric fluid (SGF) dissolution medium (0.1 N HCl with pH 1.2) with 40% EtOH. Aliquots of the dissolution media are withdrawn at the respective time points and analyzed by HPLC at 220 nm.

The in vitro release rates are indicated as percentage (based on the label content of active tested) in table 3.

TABLE 3

| | Tablets | | | | | |
|---|---|---|---|---|---|---|
| | F880/99 | | F880/105 | | F893/31 | |
| | Dissolution medium | | | | | |
| | 0.1N HCl w 40% EtOH | | 0.1N HCl w 40% EtOH | | 0.1N HCl w 40% EtOH | |
| Active tested | Hm | Nal | Hm | Nal | Hm | Nal |
| 15 min | 0 | 0 | 0 | 0 | 0 | 0 |
| 30 min | 12 | 11 | 9 | 9 | 12 | 11 |
| 45 min | 16 | 16 | 23 | 21 | 17 | 16 |
| 60 min | 21 | 20 | 39 | 36 | 21 | 20 |
| 90 min | 25 | 24 | 63 | 59 | 25 | 23 |
| 120 min | 31 | 30 | 83 | 77 | 31 | 29 |

Hm = hydromorphone HCl,
Nal = naloxone HCl,
0.1N HCl w 40% EtOH = 0.1N HCl pH 1.2 with 40% ethanol,
Values are averages of 6 measurements.

Example 2

Tablets of the composition as shown in Table 4 were manufactured.

TABLE 4

| | Tablets | | |
|---|---|---|---|
| Ingredient | F880/77 Amount (mg) | F880/83 Amount (mg) | F893/89 Amount (mg) |
| Hydromorphone HCl | 2.0 | 2.0 | 2.0 |
| Naloxone HCl | 4.0 | 4.0 | 4.0 |
| Stearyl alcohol | 25.0 | 25.0 | 15.0 |
| Ethyl cellulose N45 | 20.0 | 20.0 | 20 |
| Lactose anhydrous | 76.4 | 76.4 | 76.4 |
| Sodium stearyl fumarate | 2.6 | 2.6 | 2.6 |
| Hypromellose K100M"Extra" | 20.0 | 7.5 | 12.5 |
| Total | 150 | 142.5 | 137.5 |

Hydromorphone HCl and naloxone HCl were mixed with lactose anhydrous, stearyl alcohol and ethyl cellulose as a prolonged release polymer in a double cone mixer for 10 min.

Subsequently the blend was melt extruded using a heated twin screw extruder.

The temperature profile for the extruder was as follows:

| Extruder type | twin screw |
|---|---|
| Heating zone 1 (feeding zone) | 25° C. |
| Heating zone 2 | 50-55° C. |
| Heating zone 3 | 73-83° C. |
| Heating zones 5-10 | 70-80° C. |
| Die head | 50-55 |

The feeder rate was 10-15 kg/hr. The screw speed was set at 150-250 rpm. The die plate design allowed for multiple strand extrusion. Compressed air was used to cool the extruded strands on a conveyor belt.

Subsequently, the strands were milled to obtain granules. For milling, a Retsch mill with a 1.25 mm screen was used. This gave a substantially unimodal size distribution of the granules mainly in the range 100 to 600 μm.

The granules were then blended with sodium stearyl fumarate which was included as a lubricant. In addition, Hypromellose K100M was included as a release modifier. These components were blended for an additional 5 min. The granules were then compressed into tablets using a Kilian press.

Tablets F880/77, F880/83 and F880/89 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

Tablets F880/77, F880/83 and F880/89 were further evaluated with respect to their alcohol resistance. To this end in vitro release rates were determined using the Ph. European paddle method at 75 rpm in 500 ml simulated gastric fluid (SGF) dissolution medium (0.1 N HCl with pH 1.2) with 40% EtOH. Aliquots of the dissolution media are withdrawn at the respective time points and analyzed by HPLC at 220 nm.

The in vitro release data is indicated as percentage (based on the label content of active tested) in tables 5 to 6.

TABLE 5

| | Tablets | | | | | |
|---|---|---|---|---|---|---|
| | F880/77 | | F880/83 | | F880/89 | |
| | Dissolution medium | | | | | |
| | 0.1N HCl pH 1.2 | | 0.1N HCl pH 1.2 | | 0.1N HCl pH 1.2 | |
| Active tested | Hm | Nal | Hm | Nal | Hm | Nal |
| 0.5 h | 16 | 14 | 25 | 24 | 23 | 20 |
| 1 h | 24 | 22 | 40 | 39 | 35 | 33 |
| 2 h | 38 | 35 | 68 | 67 | 51 | 49 |
| 3 h | 50 | 45 | 87 | 86 | 65 | 63 |
| 4 h | 59 | 54 | 96 | 96 | 78 | 76 |
| 5 h | 68 | 62 | 99 | 99 | 87 | 86 |
| 6 h | 76 | 70 | 100 | 100 | 95 | 93 |
| 7 h | 82 | 77 | 100 | 100 | 96 | 95 |
| 8 h | 87 | 82 | 101 | 100 | 96 | 95 |
| 9 h | 92 | 86 | 101 | 101 | 97 | 96 |
| 10 h | 95 | 90 | 101 | 100 | 96 | 96 |
| 11 h | 97 | 93 | 101 | 101 | 97 | 96 |
| 12 h | 99 | 94 | 102 | 101 | 97 | 96 |

Hm = hydromorphone HCl,
Nal = naloxone HCl;
Values are averages of 6 measurements.

TABLE 6

| | Tablets | | | | | |
|---|---|---|---|---|---|---|
| | F880/77 | | F880/83 | | F880/89 | |
| | Dissolution medium | | | | | |
| | 0.1N HCl w 40% EtOH | | 0.1N HCl w 40% EtOH | | 0.1N HCl w 40% EtOH | |
| Active tested | Hm | Nal | Hm | Nal | Hm | Nal |
| 15 min | 15 | 14 | 12 | 10 | 10 | 8 |
| 30 min | 25 | 22 | 19 | 17 | 16 | 14 |
| 45 min | 37 | 34 | 24 | 23 | 21 | 20 |
| 60 min | n.d. | n.d. | 29 | 28 | 25 | 23 |
| 90 min | n.d. | n.d. | 37 | 35 | 32 | 30 |
| 120 min | n.d. | n.d. | 43 | 42 | 38 | 36 |

Hm = hydromorphone HCl,
Nal = naloxone HCl, 0.1N HCl w 40% EtOH = 0.1N HCl pH 1.2 with 40% ethanol,
n.d. = not determined;
Values are averages of 6 measurements.

Example 3

Granules of the composition as shown in table 7 were manufactured.

TABLE 7

| | Tablets | | |
|---|---|---|---|
| Ingredient | PN3450 Amount (mg) | PN3451 Amount (mg) | PN3452 Amount (mg) |
| Hydromorphone HCl | 4.0 | 4.0 | 4.0 |
| Naloxone HCl | 8.0 | 8.0 | 8.0 |
| Hydroxypropyl cellulose | 5.0 | 5.0 | 5.0 |
| Stearyl alcohol | 17.5 | 25.0 | 25.0 |
| Ethyl cellulose N45 | 7.5 | 10.0 | 15.0 |
| Lactose anhydrous | 46.0 | 46.0 | 46.0 |
| Magnesium stearate | 1.25 | 1.25 | 1.25 |
| Talc | 0.75 | 0.75 | 0.75 |
| Total | 90 | 100 | 105 |

Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min.

Subsequently the blend was melt extruded using a heated twin screw extruder.

The temperature profile was as follows:

| | |
|---|---|
| Extruder type | twin screw |
| Heating zone 1 (feeding zone) | 25° C. |
| Heating zone 2 | 50-55° C. |
| Heating zone 3 | 73-83° C. |
| Heating zones 5-10 | 70-80° C. |
| Die head | 50-55 |

The feeder rate was 10-15 kg/hr. The screw speed was set at 150-250 rpm. The die plate design allowed for multiple strand extrusion. Compressed air was used to cool the extruded strands on a conveyor belt.

The granules were milled and the milled granules were blended with magnesium stearate and talc in a tumbler mixer. Subsequently, the blended granules were compressed into tablets and heat treated for 30 minutes at 55° C.

Figure 1B:
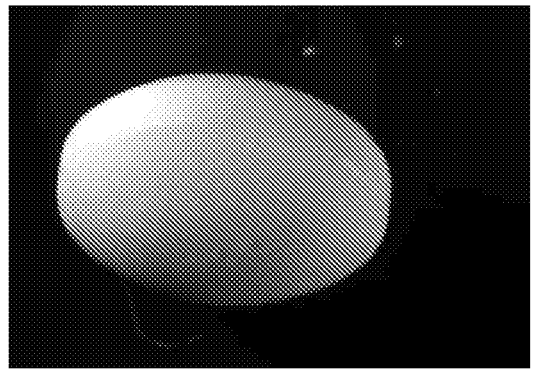

FIG. 1A and FIG. 1B show for e.g. for the case of PN3450 that heat treatment of the prolonged matrix improves the physical stability of the formulation, e.g. in that the appearance of cracks is reduced and the intactness of the tablet is improved. Similar observations were made for the other heat treated tablets mentioned herein. This may positively influence the in vitro release properties of the formulation, particularly in an in vivo setting as cracks may e.g. affect the release properties in an unpredictable manner due to e.g. a sudden change in the surface of the tablet. Furthermore, the hardness of the tablets is increase by usually 6 kP to 10 to 11 kP.

Tablets PN3450, PN3451 and PN3452 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 9.

TABLE 9

| | Tablets | | | | | |
|---|---|---|---|---|---|---|
| | PN3450 | | PN3451 | | PN3452 | |
| | Dissolution medium | | | | | |
| | 0.1N HCl pH 1.2 | | 0.1N HCl pH 1.2 | | 0.1N HCl pH 1.2 | |
| Active tested | Hm | Nal | Hm | Nal | Hm | Nal |
| 1 h | 51.50 | 50.80 | 40.54 | 39.69 | 33.22 | 32.31 |
| 2 h | 68.10 | 67.60 | 54.82 | 53.92 | 45.89 | 45.04 |
| 3 h | 78.50 | 78.30 | 64.22 | 63.54 | 54.80 | 54.05 |
| 4 h | 85.50 | 85.60 | 71.72 | 71.11 | 61.85 | 61.21 |
| 5 h | 90.50 | 90.70 | 77.74 | 77.28 | 67.57 | 67.06 |
| 6 h | 93.90 | 94.30 | 82.11 | 81.72 | 72.22 | 71.97 |
| 7 h | 95.90 | 96.60 | 85.82 | 85.65 | 76.29 | 75.94 |
| 8 h | 96.90 | 97.90 | 89.19 | 89.24 | 79.75 | 79.63 |
| 9 h | 97.50 | 98.50 | 91.82 | 91.93 | 82.81 | 82.73 |
| 10 h | 97.50 | 98.60 | 93.71 | 94.04 | 85.24 | 85.59 |

TABLE 9-continued

| | Tablets | | | | | |
|---|---|---|---|---|---|---|
| | PN3450 | | PN3451 | | PN3452 | |
| | Dissolution medium | | | | | |
| | 0.1N HCl pH 1.2 | | 0.1N HCl pH 1.2 | | 0.1N HCl pH 1.2 | |
| Active tested | Hm | Nal | Hm | Nal | Hm | Nal |
| 11 h | 97.00 | 98.30 | 95.19 | 95.72 | 87.60 | 87.83 |
| 12 h | 97.20 | 98.40 | 96.54 | 97.26 | 89.43 | 89.91 |

Hm = hydromorphone HCl,
Nal = naloxone HCl;
Values are averages of 6 measurements.

Subsequently, tablets PN350, PN3451 and PN3452 were placed in PVC blisters and stored for 3 months at 25° C. and 60% RH or for 1, 2 and 3 months at 40° C. and 75% RH.

All tablets were tested either initially or after storage for total related substances.

The results are shown in table 10.

TABLE 10

| | Tablets | | | | | |
|---|---|---|---|---|---|---|
| | PN3450 | PN3450 | PN3451 | PN3451 | PN3452 | PN3452 |
| | Container | | | | | |
| | PVC | PVC | PVC | PVC | PVC | PVC |
| | Storage | | | | | |
| | 25° C./60% RH | 40° C./75% RH | 25° C./60% RH | 40° C./75% RH | 25° C./60% RH | 40° C./75% RH |
| Initial | 0.15% | 0.15% | 0.15% | 0.15% | 0.16% | 0.16% |
| 1 month | — | 0.26% | — | 0.31% | — | 0.33% |
| 2 months | — | 0.28% | — | 0.39% | — | 0.29% |
| 3 months | 0.33% | 0.24% | 0.34% | 0.24% | 0.36% | 0.32% |

Example 4

Granules of the composition as shown in Table 11 were manufactured.

TABLE 11

| Ingredient | Tablets F923/16 Amount (mg) |
|---|---|
| Hydromorphone HCl | 4.0 |
| Naloxone HCl | 8.0 |
| Hydroxypropyl cellulose | 5.0 |
| Stearyl alcohol | 25.0 |
| Ethyl cellulose N45 | 10.0 |
| Lactose anhydrous | 46.0 |
| Total | 98 |

Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min.

Subsequently the blend was melt extruded using a heated twin screw extruder. The granules were milled and the milled granules were blended with magnesium stearate and talc in a tumbler mixer. Subsequently, the blended granules were compressed into tablets.

Tablets F923/16 were heat treated for 15 min at 55° C. The heat treated tablets were labeled F922/58A.

Tablets F923/16 were heat treated for 30 min at 55° C. The heat treated tablets were labeled F922/58B.

Tablets F923/16 were heat treated for 45 min at 55° C. The heat treated tablets were labeled F922/58C.

Tablets F923/16 as well as their heat treated counterparts were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 12.

TABLE 12

| | Tablets | | | | | | | |
|---|---|---|---|---|---|---|---|---|
| | F923/16 | | F923/58A | | F923/58B | | F923/58C | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 1 h | 48 | 47 | 40.06 | 39.10 | 39.12 | 38.17 | 38.31 | 37.54 |
| 2 h | 64 | 64 | 53.93 | 52.15 | 53.47 | 52.68 | 52.43 | 51.04 |
| 3 h | 75 | 74 | 63.75 | 62.68 | 63.79 | 62.34 | 62.19 | 61.07 |
| 4 h | 82 | 82 | 71.05 | 70.47 | 70.74 | 69.86 | 69.53 | 68.41 |
| 5 h | 86 | 87 | 78.03 | 77.01 | 76.58 | 75.71 | 75.37 | 76.35 |
| 6 h | 91 | 92 | 81.42 | 81.27 | 81.27 | 80.61 | 79.94 | 79.05 |
| 7 h | 94 | 94 | 84.75 | 84.56 | 85.59 | 82.89 | 83.97 | 83.26 |
| 8 h | 95 | 96 | 87.70 | 87.62 | 88.74 | 88.42 | 87.17 | 86.71 |
| 9 h | 96 | 97 | 91.27 | 90.97 | 90.86 | 90.71 | 89.67 | 88.92 |
| 10 h | 96 | 97 | 92.80 | 92.86 | 92.88 | 92.73 | 92.80 | 92.34 |
| 11 h | 96 | 97 | 94.14 | 94.45 | 94.32 | 94.42 | 93.73 | 91.82 |
| 12 h | 98 | 97 | 95.16 | 95.46 | 96.33 | 95.58 | 94.60 | 94.55 |

Hm = hydromorphone HCl,
Nal = naloxone HCl;
Values are averages of 6 measurements.

Example 5

Tablets with a prolonged release matrix and of comparable composition as in example 3 but comprising 20 mg ethyl cellulose were prepared. These tablets were then subjected to different heat treatments.

F922/70C: heat treated for 45 min at 55° C.
F922/70D: heat treated for 60 min at 55° C.
F922/70E: heat treated for 75 min at 55° C.

Tablets F922/70C, F922/70D and F922/70E were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 13.

TABLE 13

| | Tablets | | | | | |
|---|---|---|---|---|---|---|
| | F922/70C | | F922/70BD | | F922/70E | |
| | Dissolution medium | | | | | |
| | 0.1N HCl pH1.2 | | 0.1N HCl pH1.2 | | 0.1N HCl pH1.2 | |
| Active tested | Hm | Nal | Hm | Nal | Hm | Nal |
| 1 h | 23.09 | 21.44 | 22.56 | 20.95 | 21.89 | 20.37 |
| 2 h | 33.32 | 31.48 | 31.65 | 29.87 | 31.24 | 29.27 |
| 3 h | 41.16 | 38.85 | 38.90 | 36.71 | 38.24 | 36.14 |
| 4 h | 47.38 | 45.14 | 44.50 | 42.18 | 44.05 | 41.80 |
| 5 h | 52.37 | 49.95 | 49.65 | 47.36 | 49.11 | 46.87 |
| 6 h | 57.11 | 54.79 | 53.72 | 51.77 | 53.39 | 51.11 |
| 7 h | 60.75 | 59.23 | 57.67 | 55.57 | 57.25 | 55.11 |
| 8 h | 65.12 | 62.84 | 61.13 | 59.31 | 60.78 | 58.65 |
| 9 h | 68.15 | 66.50 | 64.27 | 62.44 | 63.93 | 61.81 |
| 10 h | 71.75 | 69.40 | 67.47 | 65.21 | 66.76 | 64.95 |
| 11 h | 74.02 | 72.26 | 70.10 | 68.42 | 69.53 | 67.72 |
| 12 h | 76.49 | 75.01 | 72.82 | 70.86 | 71.83 | 70.16 |

Hm = hydromorphone HCl,
Nal = naloxone HCl;
Values are averages of 6 measurements.

Example 6

Tablets F906/46 with a prolonged release matrix and of comparable composition as in example 3 but comprising 20 mg ethyl cellulose were prepared. These tablets were then subjected to different heat treatments.

F906/95B: F906/46 heat treated for 15 min at 55° C.
F906/95C: F906/46 heat treated for 45 min at 55° C.

Tablets F906/46, F906/95B and F906/95C were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 14.

TABLE 14

| | Tablets | | | | | |
|---|---|---|---|---|---|---|
| | F906/46 | | F9906/95B | | F906/95C | |
| | Dissolution medium | | | | | |
| | 0.1N HCl pH1.2 | | 0.1N HCl pH1.2 | | 0.1N HCl pH1.2 | |
| Active tested | Hm | Nal | Hm | Nal | Hm | Nal |
| 1 h | 42.23 | 41.72 | 35.2 | 34.1 | 35.9 | 34.8 |
| 2 h | 57.26 | 57.35 | 48.8 | 47.8 | 49.8 | 48.9 |
| 3 h | 68.41 | 69.12 | 58.1 | 57.4 | 59.4 | 58.7 |
| 4 h | 89.71 | 89.87 | 64.5 | 64.0 | 65.4 | 65.0 |
| 5 h | 95.66 | 96.01 | 71.6 | 71.4 | 71.4 | 71.3 |
| 6 h | 96.21 | 96.69 | 77.2 | 77.3 | 77.8 | 77.8 |
| 7 h | 96.24 | 96.80 | 80.6 | 80.7 | 82.6 | 82.5 |
| 8 h | 96.29 | 96.70 | 85.6 | 85.7 | 85.6 | 85.5 |
| 9 h | 96.24 | 96.75 | 88.1 | 88.2 | 89.7 | 89.6 |
| 10 h | 96.27 | 96.88 | 91.6 | 91.7 | 90.6 | 90.4 |
| 11 h | 96.38 | 96.87 | 93.4 | 93.7 | 93.1 | 93.4 |
| 12 h | 96.26 | 96.85 | 94.7 | 95.2 | 93.9 | 94.3 |

Hm = hydromorphone HCl,
Nal = naloxone HCl;
Values are averages of 6 measurements.

Example 7

Tablets of the composition as shown in table 15 were manufactured.

TABLE 15

| | Tablets | | | |
|---|---|---|---|---|
| | 933/67 | F933/69 | F933/71 | F933/73 |
| Ingredient | Amount (mg) | Amount (mg) | Amount (mg) | Amount (mg) |
| Hydromorphone HCl | 2.0 | 4.0 | 4.0 | 4.0 |
| Naloxone HCl | 4.0 | 2.0 | 4.0 | 12.0 |
| Hydroxypropyl cellulose | 5.0 | 5.0 | 5.0 | 5.0 |
| Stearyl alcohol | 25.0 | 25.0 | 25.0 | 25.0 |
| Ethyl cellulose N45 | 10.0 | 10.0 | 10.0 | 10.0 |
| Lactose anhydrous | 52.0 | 52.0 | 50.0 | 42.0 |
| Talc | 1.25 | 1.25 | 1.25 | 1.25 |
| Magnesium Stearate | 0.75 | 0.75 | 0.75 | 0.75 |
| Total | 100 | 100 | 100 | 100 |

Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above.

The granules were milled and the milled granules were blended with magnesium stearate and talc in a tumbler mixer. Subsequently, the blended granules were compressed into tablets. The tablets were then heat treated for 30 min at 55° C.

Tablets F933/67, F933/69, F933/71 and F933/73 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 16.

TABLE 16

| | Tablets | | | | | | | |
|---|---|---|---|---|---|---|---|---|
| | F933/67 | | F933/69 | | F933/71 | | F933/73 | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 1 h | 38.16 | 37.43 | 38.24 | 37.75 | 39.15 | 38.22 | 42.14 | 40.53 |
| 2 h | 52.62 | 51.72 | 53.18 | 52.23 | 53.69 | 52.54 | 57.09 | 55.52 |
| 3 h | 62.53 | 61.83 | 63.45 | 62.35 | 63.42 | 62.60 | 67.91 | 66.23 |
| 4 h | 70.09 | 69.43 | 71.23 | 70.26 | 70.94 | 70.02 | 75.35 | 73.88 |
| 5 h | 76.18 | 75.56 | 77.48 | 76.50 | 76.89 | 75.93 | 81.10 | 79.68 |
| 6 h | 81.03 | 80.48 | 82.50 | 81.63 | 81.66 | 80.68 | 85.90 | 84.79 |
| 7 h | 84.93 | 84.74 | 86.70 | 85.77 | 85.49 | 84.77 | 89.59 | 88.81 |
| 8 h | 88.38 | 88.30 | 89.90 | 88.98 | 88.63 | 87.76 | 92.33 | 91.74 |
| 9 h | 91.30 | 91.17 | 92.81 | 91.81 | 91.11 | 90.31 | 94.21 | 93.78 |
| 10 h | 93.48 | 93.63 | 94.97 | 94.13 | 93.16 | 92.53 | 96.13 | 95.87 |
| 11 h | 95.36 | 95.66 | 96.71 | 96.03 | 94.67 | 93.84 | 97.31 | 97.29 |
| 12 h | 96.88 | 97.32 | 98.06 | 97.47 | 95.98 | 95.37 | 98.78 | 99.08 |

Hm = hydromorphone HCl,
Nal = naloxone HCl;
Values are averages of 6 measurements.

Example 8

Tablets F918/109 with a similar composition as in examples 1 to 7 were manufactured and cured for 60 minutes at 55° C. They were stored for 1 month at 25° C. and 60° relative humidity (RH) or for 1 month at 40° C. and 75% RH.

Tablets F919/77 with a similar composition as in examples 1 to 7 were manufactured cured for 30 minutes at 55° C. They were stored for 1 or 2 months at 40° C. and 75% RH.

Tablets F918/109 and F919/77 were then analyzed either initially or after storage as regards in vitro release behavior using the Ph. European paddle method at 75 rpm in 500 simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in tables 17 and 18.

TABLE 17

| | Tablets | | | | | |
|---|---|---|---|---|---|---|
| | F918/109 | | F918/109 Storage | | F918/109 | |
| | — | | 1 month, 25° C., 60% RH | | 1 month, 40° C., 75% RH | |
| | Dissolution medium | | | | | |
| | 0.1N HCl pH1.2 | | 0.1N HCl pH1.2 | | 0.1N HCl pH 1.2 | |
| Active tested | Hm | Nal | Hm | Nal | Hm | Nal |
| 1 h | 32.11 | 31.09 | 32.85 | 31.47 | 35.03 | 33.83 |
| 2 h | 44.68 | 43.47 | 45.64 | 44.07 | 47.77 | 46.49 |
| 3 h | 53.86 | 52.54 | 54.62 | 52.89 | 56.80 | 55.47 |
| 4 h | 60.84 | 59.48 | 61.71 | 59.87 | 63.65 | 62.30 |
| 5 h | 66.90 | 65.53 | 67.71 | 65.84 | 69.30 | 67.88 |
| 6 h | 71.81 | 70.44 | 72.41 | 70.53 | 74.05 | 72.68 |
| 7 h | 75.90 | 74.65 | 76.58 | 74.83 | 78.18 | 76.77 |
| 8 h | 79.41 | 78.30 | 80.24 | 78.49 | 81.63 | 80.26 |
| 9 h | 82.63 | 81.70 | 83.33 | 81.67 | 84.72 | 83.36 |
| 10 h | 85.28 | 84.41 | 85.86 | 84.19 | 87.31 | 86.03 |
| 11 h | 87.67 | 86.88 | 88.37 | 86.72 | 89.39 | 88.21 |
| 12 h | 89.71 | 89.22 | 90.14 | 88.69 | 91.13 | 90.18 |

Hm = hydromorphone HCl,
Nal = naloxone HCl;
Values are averages of 6 measurements.

TABLE 18

| | Tablets | | | | | |
|---|---|---|---|---|---|---|
| | F919/77 | | F919/77 Storage | | F919/77 | |
| | — | | 1 month, 40° C., 75% RH | | 1 month, 40° C., 75% RH | |
| | Dissolution medium | | | | | |
| | 0.1N HCl pH1.2 | | 0.1N HCl pH1.2 | | 0.1N HCl pH 1.2 | |
| Active tested | Hm | Nal | Hm | Nal | Hm | Nal |
| 1 h | 30.29 | 29.36 | 30.49 | 29.50 | 31.07 | 30.12 |
| 2 h | 42.41 | 41.49 | 41.88 | 40.81 | 42.69 | 41.64 |
| 3 h | 51.14 | 50.30 | 50.08 | 48.95 | 50.93 | 49.78 |
| 4 h | 58.01 | 57.25 | 56.59 | 55.39 | 57.40 | 56.41 |
| 5 h | 63.64 | 63.05 | 61.98 | 60.72 | 62.60 | 61.78 |
| 6 h | 68.66 | 68.05 | 66.43 | 65.29 | 67.16 | 66.22 |
| 7 h | 72.77 | 72.37 | 70.28 | 69.16 | 71.10 | 70.16 |
| 8 h | 76.30 | 76.10 | 73.60 | 72.66 | 74.52 | 73.49 |
| 9 h | 79.47 | 79.32 | 76.55 | 75.72 | 77.38 | 76.63 |
| 10 h | 82.27 | 82.18 | 79.24 | 78.34 | 79.95 | 79.19 |
| 11 h | 84.62 | 84.57 | 81.50 | 80.82 | 82.36 | 81.72 |
| 12 h | 86.68 | 86.83 | 83.43 | 82.82 | 84.36 | 84.07 |

Hm = hydromorphone HCl,
Nal = naloxone HCl;
Values are averages of 6 measurements.

Example 9

Tablets F899/29, F899/39 and F908/93 were produced similarly to examples 1 to 8.

Subsequently, tablets F899/29 and F899/39 were placed in Duma fos containers and stored for 1, 2 or 5 months at 25° C. and 60% RH or at 40° C. and 75% RH. Tablets F908/93 were placed either in PVC containers or in PVC coated PVdC blisters and stored for 1, 2 or 5 months at 25° C. and 60% RH or at 40° C. and 75% RH.

All tablets were tested either initially or after storage for total related substances.

The results are shown in tables 19 and 20.

TABLE 19

| Storage | Tablets | | | |
|---|---|---|---|---|
| | F899/29 | F899/29 | F899/39 | F899/29 |
| | Container | | | |
| | Duma fos 25° C./ 60% RH | Duma fos 40° C./ 75% RH | Duma fos 25° C./ 60% RH | Duma fos 40° C./ 75% RH |
| Initial | 0.05% | 0.05% | 0.16% | 0.16% |
| 1 month | — | 0.09% | — | 0.17% |
| 2 months | — | 0.26% | — | 0.24% |
| 5 months | 0.17% | 0.30% | 0.10% | 0.24% |

TABLE 20

| Storage | Tablet | | | |
|---|---|---|---|---|
| | F908/93 | F908/93 | F908/93 | F908/93 |
| | Container | | | |
| | PVC 25° C./ 60% RH | PVC 40° C./ 75% RH | PVS/PVdC 25° C./ 60% RH | PVC/PVdC 40° C./ 75% RH |
| Initial | 0.10% | 0.10% | 0.10% | 0.10% |
| 1 month | 0.21% | 0.24% | 0.40% | 0.31% |
| 2 months | 0.25% | 0.30% | 0.65% | 0.46% |
| 5 months | — | 0.49% | — | 0.64% |

Example 10

Tablets of the composition as shown in Table 21 were manufactured.

TABLE 21

| Ingredient | Tablets | | | |
|---|---|---|---|---|
| | 933/107B Amount (mg) | F929/73B Amount (mg) | F929/85B Amount (mg) | F929/79B Amount (mg) |
| Hydromorphone HCl | 4.00 | 4.00 | 4.00 | 4.00 |
| Naloxone HCl | 8.00 | 8.00 | 8.00 | 8.00 |
| Hydroxypropyl cellulose | 5.00 | 5.00 | 5.00 | 5.00 |
| Ethyl cellulose N45 | 15.0 | 15.0 | 15.0 | 15.0 |
| Stearyl alcohol | 25.0 | 25.0 | 25.0 | 25.0 |
| Lactose anhydrous | 46.0 | 46.0 | 46.0 | 46.0 |
| Magnesium Stearate | 1.25 | 1.25 | 1.25 | 1.25 |
| Talcum | 0.75 | 0.75 | 0.75 | 0.75 |
| Total | 105 | 105 | 105 | 105 |
| Surelease E7-7050* | | 7.00 | 5.00 | 3.75 |
| Opadry II brown* | | 2.30 | 2.50 | 3.75 |
| Purified water** | | 28.0 | 20.0 | 15.0 |
| Total | 105 | 114.3 | 112.5 | 112.5 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets. The tablets were then heat treated for 45 min at 55° C. Subsequently the coatings were applied.

Tablets F933/107B, F929/73B, F929/85B and F929/79B were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 22.

TABLE 22

| | Tablets | | | | | | | |
|---|---|---|---|---|---|---|---|---|
| | F933/107B | | F929/73B | | F929/85B | | F929/79B | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 1 h | 41.11 | 40.19 | 0.13 | 0.19 | 8.61 | 7.26 | 29.21 | 27.74 |
| 2 h | 56.10 | 55.15 | 0.81 | 0.65 | 17.89 | 15.80 | 43.70 | 41.98 |
| 3 h | 66.02 | 64.99 | 1.58 | 1.27 | 25.06 | 22.59 | 54.21 | 52.41 |
| 4 h | 73.90 | 73.07 | 2.55 | 1.97 | 31.14 | 28.42 | 62.18 | 60.40 |
| 5 h | 79.71 | 79.18 | 3.45 | 2.65 | 36.34 | 33.38 | 68.94 | 67.27 |
| 6 h | 84.28 | 83.60 | 5.08 | 3.95 | 41.15 | 38.09 | 74.37 | 72.63 |
| 7 h | 88.19 | 87.84 | 6.76 | 5.45 | 45.75 | 42.60 | 78.62 | 77.05 |
| 8 h | 91.29 | 91.03 | 8.56 | 7.05 | 50.55 | 47.25 | 82.91 | 81.37 |
| 9 h | 93.91 | 93.62 | 10.18 | 8.51 | 54.51 | 51.28 | 86.11 | 84.57 |
| 10 h | 95.95 | 95.91 | 11.92 | 10.05 | 58.50 | 55.34 | 88.67 | 87.31 |
| 11 h | 97.67 | 98.06 | 13.56 | 11.62 | 61.91 | 58.80 | 91.23 | 90.11 |
| 12 h | 98.57 | 98.74 | 15.37 | 13.27 | 65.24 | 62.11 | 92.91 | 91.70 |

Hm = hydromorphone HCl,
Nal = naloxone HCl;
Values are averages of 6 measurements.

Example 11

Tablets of the composition as shown in Table 23 were manufactured.

TABLE 23

| Ingredient | Tablets | | |
|---|---|---|---|
| | F941/07B Amount (mg) | F929/91C Amount (mg) | F929/97C Amount (mg) |
| Hydromorphone HCl | 4.00 | 4.00 | 4.00 |
| Naloxone HCl | 4.00 | 4.00 | 4.00 |
| Hydroxypropyl cellulose | 5.00 | 5.00 | 5.00 |
| Ethyl cellulose N45* | 7.50 | 7.50 | 7.50 |
| Stearyl alcohol | 17.5 | 17.5 | 17.5 |
| Lactose anhydrous | 50.0 | 50.0 | 50.0 |
| Magnesium Stearate | 1.25 | 1.25 | 1.25 |
| Talcum | 0.75 | 0.75 | 0.75 |
| Total | 90 | 90 | 90 |
| Surelease E7-7050* | | 7.50 | 10.0 |
| Opadry II brown* | | 5.00 | 5.00 |
| Purified water** | | 30.0 | 40.0 |
| Total | 90 | 102.5 | 105 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets. The tablets were then heat treated for 45 min at 55° C. Subsequently the coatings were applied.

Tablets F941/07B, F929/91C and F929/97C were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 24.

TABLE 24

| | Tablets | | | | | |
|---|---|---|---|---|---|---|
| | F941/07B, | | F929/91C | | F929/97C | |
| | Dissolution medium | | | | | |
| | 0.1N HCl pH1.2 | | 0.1N HCl pH1.2 | | 0.1N HCl pH1.2 | |
| Active tested | Hm | Nal | Hm | Nal | Hm | Nal |
| 1 h | 48.75 | 47.97 | 12.07 | 11.02 | 1.30 | 0.97 |
| 2 h | 65.20 | 64.34 | 25.71 | 24.46 | 4.46 | 3.51 |
| 3 h | 75.96 | 75.05 | 35.83 | 34.48 | 7.82 | 6.46 |
| 4 h | 83.03 | 82.25 | 44.13 | 42.68 | 11.81 | 10.09 |
| 5 h | 88.29 | 87.64 | 51.32 | 49.85 | 18.08 | 16.14 |
| 6 h | 92.21 | 91.60 | 57.86 | 56.41 | 28.52 | 26.46 |
| 7 h | 94.81 | 94.48 | 63.60 | 62.18 | 35.81 | 33.71 |
| 8 h | 96.53 | 96.01 | 68.42 | 66.99 | 41.92 | 39.79 |
| 9 h | 97.31 | 97.11 | 72.85 | 71.44 | 47.04 | 44.85 |
| 10 h | 97.54 | 97.46 | 76.94 | 75.72 | 51.46 | 49.24 |
| 11 h | 97.75 | 97.82 | 79.73 | 78.48 | 55.40 | 53.22 |
| 12 h | 97.70 | 97.71 | 82.77 | 81.59 | 58.87 | 56.65 |

Hm = hydromorphone HCl,
Nal = naloxone HCl;
Values are averages of 6 measurements.

Tablets F929/91C and F929/97C were further evaluated with respect to their alcohol resistance. To this end in vitro release rates were determined using the Ph. European paddle method at 75 rpm in 500 ml simulated gastric fluid (SGF) dissolution medium (0.1 N HCl with pH 1.2) with 40% EtOH. Aliquots of the dissolution media are withdrawn at the respective time points and analyzed by HPLC at 220 nm.

The in vitro release data is indicated as percentage (based on the label content of active tested) in table 25.

TABLE 25

| | Tablets | | | |
|---|---|---|---|---|
| | F929/91C | | F929/97C | |
| | Dissolution medium | | | |
| | 0.1N HCl w 40% EtOH | | 0.1N HCl w 40% EtOH | |
| Active tested | Hm | Nal | Hm | Nal |
| 15 min | 1.16 | 0.78 | 0.00 | 0.00 |
| 30 min | n.d. | n.d. | n.d. | n.d. |
| 45 min | n.d. | n.d. | n.d. | n.d. |
| 60 min | 12.07 | 11.02 | 1.30 | 0.97 |
| 90 min | n.d. | n.d. | n.d. | n.d. |
| 120 min | 25.71 | 24.46 | 4.46 | 3.51 |

Hm = hydromorphone HCl,
Nal = naloxone HCl,
0.1N HCl w 40% EtOH = 0.1N HCl pH 1.2 with 40% ethanol,
n.d. = not determined Example 12

Tablets of the composition as shown in Table 26 were manufactured.

TABLE 26

| | Tablets | | | |
|---|---|---|---|---|
| Ingredient | F941/60B Amount (mg) | F945/06 Amount (mg) | F944/86 Amount (mg) | F945/30 Amount (mg) |
| Hydromorphone HCl | 4.00 | 4.00 | 4.00 | 4.00 |
| Naloxone HCl | 2.00 | 2.00 | 8.00 | 8.00 |
| Hydroxypropyl cellulose | 5.00 | 5.00 | 5.00 | 5.00 |
| Ethyl cellulose N45 | 15.0 | 15.0 | 10.00 | 10.00 |
| Stearyl alcohol | 25.0 | 25.0 | 25.0 | 25.0 |
| Lactose anhydrous | 52.0 | 52.0 | 46.0 | 46.0 |
| Magnesium Stearate | 1.25 | 1.25 | 1.25 | 1.25 |
| Talcum | 0.75 | 0.75 | 0.75 | 0.75 |
| Total | 105 | 105 | 100 | 100 |
| Surelease E7-7050* | | 12.0 | | 7.50 |
| Opadry II brown* | | 0.0 | | 5.00 |
| Purified water** | | 48.0 | | 30.0 |
| Total | 105 | 117 | 100 | 112.5 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets. Tablets F941/60B were heat treated for 45 min at 55° C. Tablets F944/86 were heat treated for 30 min at 55° C. Subsequently the coatings were applied.

Tablets F941/60B, F945/06, F944/86 and F945/30 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 27.

TABLE 27

| | Tablets | | | | | | | |
|---|---|---|---|---|---|---|---|---|
| | F941/60B | | F945/06 | | F944/86 | | F945/30 | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 1 h | 31.91 | 31.30 | 0.07 | 0.24 | 42.34 | 41.05 | 10.12 | 8.50 |
| 2 h | 44.71 | 44.11 | 0.00 | 0.00 | 57.27 | 55.66 | 22.45 | 20.08 |
| 3 h | 53.54 | 52.76 | 0.00 | 0.15 | 67.40 | 65.71 | 31.05 | 28.40 |
| 4 h | 60.84 | 59.92 | 0.00 | 0.00 | 75.13 | 73.49 | 37.72 | 34.87 |
| 5 h | 66.54 | 65.73 | 0.00 | 0.00 | 80.39 | 79.05 | 43.69 | 40.70 |
| 6 h | 71.65 | 70.74 | 0.00 | 0.45 | 85.16 | 83.78 | 49.07 | 45.90 |
| 7 h | 75.81 | 74.88 | 0.00 | 0.86 | 88.91 | 87.48 | 53.65 | 50.47 |
| 8 h | 79.32 | 78.62 | 0.00 | 1.15 | 91.74 | 90.58 | 58.14 | 54.82 |
| 9 h | 82.63 | 81.74 | 0.00 | 1.31 | 94.30 | 93.04 | 61.81 | 58.69 |
| 10 h | 85.47 | 84.67 | 0.00 | 1.50 | 96.59 | 95.76 | 65.50 | 62.36 |

TABLE 27-continued

| | Tablets | | | | | | | |
|---|---|---|---|---|---|---|---|---|
| | F941/60B | | F945/06 | | F944/86 | | F945/30 | |
| | \multicolumn{8}{c}{Dissolution medium} | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 11 h | 87.92 | 87.17 | 0.00 | 1.68 | 97.14 | 96.57 | 69.01 | 65.70 |
| 12 h | 89.64 | 88.92 | 0.00 | 1.87 | 97.82 | 97.39 | 72.00 | 68.89 |

Hm = hydromorphone HCl,
Nal = naloxone HCl;
Values are averages of 6 measurements.

Example 13

Tablets of the composition as shown in Table 28 were manufactured.

TABLE 28

| | Tablets | | |
|---|---|---|---|
| Ingredient | F941/07B Amount (mg) | F944/49 Amount (mg) | F929/103 Amount (mg) |
| Hydromorphone HCl | 4.00 | 4.00 | 4.00 |
| Naloxone HCl | 4.00 | 4.00 | 4.00 |
| Hydroxypropyl cellulose | 5.00 | 5.00 | 5.00 |
| Ethyl cellulose N45 | 7.50 | 7.50 | 7.50 |
| Stearyl alcohol | 17.5 | 17.5 | 17.5 |
| Lactose anhydrous | 50.0 | 50.0 | 50.0 |
| Magnesium Stearate | 1.25 | 1.25 | 1.25 |
| Talcum | 0.75 | 0.75 | 0.75 |
| Total | 90 | 90 | 90 |
| Eudragit RL30D* | | 5.00 | 14.0 |
| Eudragit RS30D* | | 5.00 | 0.00 |
| Talc | | 5.00 | 7.00 |
| Triethyl citrate | | 2.00 | 2.80 |
| Purified water** | | 44.8 | 62.6 |
| Total | 90 | 107 | 113.8 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets. Tablets were then heat treated for 45 min at 55° C. Subsequently the coatings were applied.

Tablets F941/07B, F944/49 and F929/103 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 29.

TABLE 29

| | Tablets | | | | | |
|---|---|---|---|---|---|---|
| | F941/07B | | F944/49 | | F929/103 | |
| | \multicolumn{6}{c}{Dissolution medium} | | | | | |
| | 0.1N HCl pH1.2 | | 0.1N HCl pH1.2 | | 0.1N HCl pH1.2 | |
| Active tested | Hm | Nal | Hm | Nal | Hm | Nal |
| 1 h | 48.75 | 47.97 | 6.04 | 4.60 | 14.54 | 12.42 |
| 2 h | 65.20 | 64.34 | 24.83 | 21.75 | 39.00 | 35.75 |
| 3 h | 75.96 | 75.05 | 49.18 | 46.69 | 57.55 | 54.52 |
| 4 h | 83.03 | 82.25 | 61.94 | 59.94 | 70.09 | 67.76 |
| 5 h | 88.29 | 87.64 | 71.03 | 69.11 | 78.89 | 77.01 |
| 6 h | 92.21 | 91.60 | 78.22 | 76.31 | 85.20 | 83.57 |
| 7 h | 94.81 | 94.48 | 83.60 | 81.83 | 89.78 | 88.43 |
| 8 h | 96.53 | 96.01 | 87.96 | 86.66 | 93.23 | 92.16 |
| 9 h | 97.31 | 97.11 | 91.56 | 90.05 | 95.60 | 94.58 |
| 10 h | 97.54 | 97.46 | 93.89 | 92.84 | 97.08 | 96.33 |
| 11 h | 97.75 | 97.82 | 95.84 | 95.06 | 98.16 | 97.36 |
| 12 h | 97.70 | 97.71 | 97.07 | 96.61 | 98.46 | 98.01 |

Hm = hydromorphone HCl,
Nal = naloxone HCl;
Values are averages of 6 measurements.

Example 14

Tablets of the composition as shown in Table 30 were manufactured.

TABLE 30

| | Tablets | |
|---|---|---|
| Ingredient | F944/90 Amount (mg) | F944/101D Amount (mg) |
| Hydromorphone HCl | 4.00 | 4.00 |
| Naloxone HCl | 8.00 | 8.00 |
| Hydroxypropyl cellulose | 5.00 | 5.00 |
| Ethyl cellulose N45 | 7.50 | 7.50 |
| Stearyl alcohol | 17.5 | 17.5 |
| Lactose anhydrous | 46.0 | 46.0 |
| Magnesium Stearate | 1.25 | 1.25 |
| Talcum | 0.75 | 0.75 |
| Total | 90 | 90 |
| Surelease E7-7050* | | 7.50 |
| Advantia Preferred* (Aquarius HPMC) | | 5.00 |
| Purified water** | | 30.0 |
| Total | 90 | 102.5 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets.

Tablets were then heat treated for 30 min at 55° C. Subsequently the coatings were applied.

Tablets F944/90 and F944/101D were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 31.

TABLE 31

| | Tablets | | | |
|---|---|---|---|---|
| | F944/90 | | F944/101D | |
| | Dissolution medium | | | |
| | 0.1N HCl pH1.2 | | 0.1N HCl pH1.2 | |
| Active tested | Hm | Nal | Hm | Nal |
| 1 h | 51.08 | 49.95 | 21.88 | 20.12 |
| 2 h | 68.55 | 67.18 | 38.23 | 36.15 |
| 3 h | 79.32 | 77.97 | 50.93 | 48.65 |
| 4 h | 86.47 | 85.26 | 60.36 | 58.15 |
| 5 h | 91.63 | 90.53 | 67.82 | 65.77 |
| 6 h | 94.86 | 94.04 | 74.74 | 72.72 |
| 7 h | 96.95 | 96.34 | 79.32 | 77.41 |
| 8 h | 97.90 | 97.48 | 83.90 | 82.14 |
| 9 h | 98.56 | 98.27 | 87.03 | 85.47 |
| 10 h | 98.97 | 98.72 | 90.14 | 88.73 |
| 11 h | 98.86 | 98.71 | 92.32 | 91.10 |
| 12 h | 98.87 | 98.76 | 94.09 | 93.11 |

Hm = hydromorphone HCl,
Nal = naloxone HCl;
Values are averages of 6 measurements.

Tablets similar to F994/101D were manufactured. In tablets F994/101B, the weight gain by coating was about 5 mg. Tablets F994/101E were the same as tablets F994/101D except that they had been cured 30 minutes at 55° C. after the coating had been applied. These tablets were also tested for their in vitro release.

The in vitro release data is indicated as percentage (based on the label content of active tested) in table 32.

TABLE 32

| | Tablets | | | | | |
|---|---|---|---|---|---|---|
| | F944/101B | | F944/101D | | F944/101E | |
| | Dissolution medium | | | | | |
| | 0.1N HCl pH1.2 | | 0.1N HCl pH1.2 | | 0.1N HCl pH1.2 | |
| Active tested | Hm | Nal | Hm | Nal | Hm | Nal |
| 1 h | 33.91 | 32.23 | 21.88 | 20.12 | 15.55 | 13.05 |
| 2 h | 50.66 | 48.53 | 38.23 | 36.15 | 31.17 | 28.20 |
| 3 h | 62.06 | 59.71 | 50.93 | 48.65 | 42.66 | 39.67 |
| 4 h | 70.64 | 68.21 | 60.36 | 58.15 | 52.68 | 49.67 |
| 5 h | 77.57 | 75.20 | 67.82 | 65.77 | 60.06 | 56.91 |
| 6 h | 82.52 | 80.46 | 74.74 | 72.72 | 67.14 | 64.15 |
| 7 h | 86.96 | 84.87 | 79.32 | 77.41 | 72.70 | 69.83 |
| 8 h | 90.51 | 88.57 | 83.90 | 82.14 | 77.78 | 75.03 |
| 9 h | 92.75 | 90.85 | 87.03 | 85.47 | 82.36 | 79.77 |
| 10 h | 94.99 | 93.44 | 90.14 | 88.73 | 85.18 | 82.76 |
| 11 h | 95.81 | 94.56 | 92.32 | 91.10 | 87.84 | 85.55 |
| 12 h | 97.02 | 95.83 | 94.09 | 93.11 | 90.58 | 88.36 |

Hm = hydromorphone HCl,
Nal = naloxone HCl;
Values are averages of 6 measurements.

Example 15

Tablets of the composition as shown in Table 33 were manufactured.

TABLE 33

| | Tablets | | | | |
|---|---|---|---|---|---|
| | PN3450 | F944/78 | PN3451 | F944/82 | F945/69 |
| Ingredient | Amount (mg) | Amount (mg) | Amount (mg) | Amount (mg) | Amount (mg) |
| Hydromorphone HCl | 4.0 | 4.00 | 4.0 | 4.00 | 4.00 |
| Naloxone HCl | 8.0 | 8.00 | 8.0 | 8.00 | 8.00 |
| Hydroxypropyl cellulose | 5.0 | 5.00 | 5.0 | 5.00 | 5.00 |
| Stearyl alcohol | 17.5 | 17.5 | 25.0 | 25.0 | 25.0 |
| Ethyl cellulose N45 | 7.5 | 7.5 | 10.0 | 10.0 | 10.0 |
| Lactose anhydrous | 46.0 | 46.0 | 46.0 | 46.0 | 46.0 |
| Talc | 1.25 | 1.25 | 1.25 | 1.25 | 1.25 |
| Magnesium Stearate | 0.75 | 0.75 | 0.75 | 0.75 | 0.75 |
| Total | 90 | 90 | 100 | 100 | 100 |
| Stearyl alcohol (extragranular) | | 15.00 | | 15.00 | 0.00 |
| Ethylcellulose N45 (extragranular) | | 0.00 | | 0.00 | 15.00 |
| Total | 90 | 105 | 100 | 115 | 115 |

Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above.

The milled granules were blended with magnesium stearate and talc and the additional amount of extragranular stearyl alcohol or ethyl cellulose in a tumbler mixer. Subsequently, the blended granules were compressed into tablets. The tablets were then heat treated for 30 min at 55° C.

Tablets PN3450, PN3451, F944/78, F944/82 and F945/69 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 34.

TABLE 34

| | Tablets | | | | | | | | | |
|---|---|---|---|---|---|---|---|---|---|---|
| | PN3450 | | F944/78 | | PN3451 | | F944/82 | | F945/69 | |
| | Dissolution medium | | | | | | | | | |
| | 0.1N HCl pH1.2 | | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal | Hm | Nal |
| 1 h | 51.50 | 50.80 | 43.94 | 42.52 | 40.54 | 39.69 | 30.89 | 29.56 | 38.94 | 37.56 |
| 2 h | 68.10 | 67.60 | 59.69 | 57.94 | 54.82 | 53.92 | 42.72 | 41.12 | 53.24 | 55.65 |
| 3 h | 78.50 | 78.30 | 70.31 | 68.46 | 64.22 | 63.54 | 51.12 | 49.36 | 62.95 | 61.61 |
| 4 h | 85.50 | 85.60 | 77.61 | 75.77 | 71.72 | 71.11 | 57.95 | 56.13 | 70.34 | 68.94 |
| 5 h | 90.50 | 90.70 | 83.81 | 82.16 | 77.74 | 77.28 | 63.21 | 61.38 | 76.28 | 75.05 |
| 6 h | 93.90 | 94.30 | 88.25 | 86.65 | 82.11 | 81.72 | 67.88 | 65.91 | 81.31 | 80.03 |
| 7 h | 95.90 | 96.60 | 91.83 | 90.29 | 85.82 | 85.65 | 71.76 | 69.85 | 85.10 | 84.05 |
| 8 h | 96.90 | 97.90 | 94.57 | 93.06 | 89.19 | 89.24 | 75.34 | 73.46 | 88.53 | 87.47 |
| 9 h | 97.50 | 98.50 | 96.50 | 95.28 | 91.82 | 91.93 | 78.37 | 76.52 | 91.35 | 90.32 |
| 10 h | 97.50 | 98.60 | 98.34 | 97.37 | 93.71 | 94.04 | 81.07 | 79.29 | 93.67 | 92.44 |
| 11 h | 97.00 | 98.30 | 99.36 | 98.52 | 95.19 | 95.72 | 83.52 | 81.76 | 95.31 | 94.47 |
| 12 h | 97.20 | 98.40 | 99.58 | 98.93 | 96.54 | 97.26 | 85.64 | 83.97 | 96.61 | 95.71 |

Hm = hydromorphone HCl,
Nal = naloxone HCl;
Values are averages of 6 measurements.

Example 16

Tablets of the composition as shown in Table 35 were manufactured.

TABLE 35

| | Tablets | | | |
|---|---|---|---|---|
| Ingredient | PN3642 Amount (mg) | PN3643 Amount (mg) | PN3644 Amount (mg) | PN3645 Amount (mg) |
| Hydromorphone HCl | 4.00 | 4.00 | 4.00 | 4.00 |
| Naloxone HCl | 8.00 | 8.00 | 8.00 | 8.00 |
| Hydroxypropyl cellulose | 5.00 | 5.00 | 5.00 | 5.00 |
| Ethyl cellulose N45 | 7.50 | 7.50 | 15.0 | 15.0 |
| Stearyl alcohol | 17.5 | 17.5 | 25.0 | 25.0 |
| Lactose anhydrous | 52.0 | 52.0 | 46.0 | 46.0 |
| Magnesium Stearate | 0.75 | 0.75 | 0.75 | 0.75 |
| Talcum | 1.25 | 1.25 | 1.25 | 1.25 |
| Total | 90 | 90 | 105 | 105 |
| Surelease E7-19030* | 5.00 | 6.00 | 5.00 | 9.00 |
| Opadry II brown* | 5.00 | 4.00 | 5.00 | 6.00 |
| Purified water** | 20.0 | 24.0 | 20.0 | 36.0 |
| Total | 100 | 100 | 115 | 120 |

*The amount indicated refers to the amount of solids used.
**Evaporated during coating Hydromorphone HCl and naloxone HCl were mixed with lactose anhydrous, stearyl alcohol, hydroxypropyl cellulose and ethyl cellulose N45 as a prolonged release polymer. These components were blended in a double cone mixer for 10 min. Subsequently the blend was melt extruded using a heated twin screw extruder as described above. The milled granules were blended with magnesium stearate and talc in a tumbler mixer. Subsequently, the blended granules were compressed into tablets. The tablets were then heat treated for 60 min at 55° C. Subsequently the coatings were applied with Manesty air atomised spray fitted with a 1.2 mm nozzle adjusted to give an even spray pattern and located approximately 15 cm from tablet bed.

Atomising air pressure 1.8 bar
Fan width air pressure 2.0 bar
Inlet air temperature 52° C.
Outlet air temperature 40-45° C.
Air flow 350 m3/hr
Drum speed 20 rpm
Spray rate ca. 6-10 g/min
Cabinet depression −50
Wall thickness of silicon tubing 1.6 mm
Bore of silicon tubing 4.8 mm Tablets PN3642, PN3643, PN 3644 and PN3645 were then analyzed as regards in vitro release behavior using the Ph. European paddle method at 75 rpm in 500 ml simulated gastric fluid (SGF) dissolution medium (0.1 N HCl with pH 1.2). Aliquots of the dissolution media are withdrawn at the respective time points and analyzed by HPLC at 220 nm.

The in vitro release data is indicated as percentage (based on the label content of active tested) in table 36.

TABLE 36

| | Tablets | | | | | | | |
|---|---|---|---|---|---|---|---|---|
| | PN3642 | | PN3643 | | PN3644 | | PN3645 | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 1 h | 30.14 | 28.16 | 16.15 | 13.62 | 23.29 | 21.81 | 12.70 | 10.75 |
| 2 h | 49.65 | 47.91 | 35.51 | 32.66 | 38.00 | 36.72 | 26.59 | 24.45 |
| 3 h | 63.09 | 61.54 | 48.58 | 45.95 | 48.11 | 46.87 | 36.40 | 34.25 |
| 4 h | 72.95 | 71.53 | 58.85 | 56.36 | 55.98 | 54.76 | 44.48 | 42.37 |
| 5 h | 80.56 | 79.42 | 67.19 | 64.83 | 62.40 | 61.34 | 51.12 | 49.13 |
| 6 h | 86.32 | 85.32 | 74.14 | 71.99 | 68.00 | 67.04 | 56.94 | 54.86 |
| 7 h | 90.74 | 89.90 | 79.91 | 77.93 | 72.67 | 71.84 | 62.26 | 60.16 |
| 8 h | 93.79 | 93.27 | 84.68 | 82.84 | 76.69 | 76.04 | 66.72 | 64.85 |
| 9 h | 95.94 | 95.81 | 88.57 | 87.10 | 80.26 | 79.73 | 70.73 | 68.92 |
| 10 h | 97.59 | 97.63 | 91.68 | 90.47 | 83.28 | 82.73 | 74.08 | 72.62 |
| 11 h | 98.31 | 98.63 | 94.10 | 93.30 | 86.00 | 85.59 | 77.48 | 75.82 |
| 12 h | 98.77 | 99.28 | 96.05 | 95.31 | 88.08 | 87.94 | 80.30 | 78.70 |

Hm = hydromorphone HCl,
Nal = naloxone HCl.
Values are averages of 6 measurements.

Tablets PN3642, PN3643, PN3644, PN3645 were further evaluated with respect to their alcohol resistance. To this end in vitro release rates were determined using the Ph. European paddle method at 75 rpm in 500 ml simulated gastric fluid (SGF) dissolution medium (0.1 N HCl with pH 1.2) with 40% EtOH. Aliquots of the dissolution media are withdrawn at the respective time points and analyzed by HPLC at 220 nm.

The in vitro release data is indicated as percentage (based on the label content of active tested) in table 37.

TABLE 37

| | Tablets | | | | | | | |
|---|---|---|---|---|---|---|---|---|
| | PN3642 | | PN3643 | | PN3644 | | PN3645 | |
| | Dissolution medium | | | | | | | |
| | 0.1N HCl pH1.2 | | 0.1N HCl pH1.2 | | 0.1N HCl pH1.2 | | 0.1N HCl pH1.2 | |
| Active tested | Hm | Nal | Hm | Nal | Hm | Nal | Hm | Nal |
| 15 min | 3.8 | 2.7 | 1.8 | 1.4 | 4.0 | 2.7 | 1.4 | 0.7 |
| 30 min | 10.2 | 8.6 | 5.6 | 4.5 | 9.5 | 8.2 | 2.1 | 1.9 |
| 45 min | 16.7 | 14.6 | 9.9 | 8.3 | 15.3 | 13.8 | 4.6 | 3.8 |
| 60 mi | 22.4 | 20.1 | 14.1 | 10.7 | 20.3 | 18.5 | 7.3 | 6.1 |
| 90 min | 31.8 | 29.3 | 21.9 | 17.6 | 27.9 | 26.1 | 12.8 | 11.0 |
| 120 min | 39.5 | 36.8 | 29.4 | 25.6 | 34.1 | 32.4 | 18.0 | 15.8 |

Hm = hydromorphone HCl,
Nal = naloxone HCl,
0.1N HCl w 40% EtOH = 0.1N HCl pH 1.2 with 40% ethanol,
n.d. = not determined;
Values are averages of 6 measurements.

Subsequently, tablets PN3642, PN3643, PN3644 and PN3645 were placed in PVC blisters and stored for 1, 2 and 3 months at 40° C. and 75% RH.

All tablets were tested either initially or after storage for total related substances.

The results are shown in table 38.

TABLE 38

| | Tablets | | | |
|---|---|---|---|---|
| | PN3642 | PN3643 | PN3644 | PN3645 |
| | Container | | | |
| Storage | PVC 40° C./75% RH | PVC 40° C./75% RH | PVC 40° C./75% RH | PVC 40° C./75% RH |
| Initial | 0.00% | 0.00% | 0.00% | 0.08% |
| 1 month | 0.00% | 0.05% | 0.05% | 0.00% |
| 2 months | 0.05% | 0.00% | 0.00% | 0.00% |
| 3 months | 0.05% | 0.05% | 0.00% | 0.05% |

All tablets were tested either initially or after storage also for known related substances. These were noroxymorphone, hydromorphone N-oxide, pseudohydromorphone, naloxone N-oxide, pseudonaloxone. All known substances were either less than limit of detection or less than limit of quantification.

Example 17

Tablets corresponding to tablets of PN3462 were tested in an open label, single-dose study in 15 healthy subjects in the fasted state. The mean AUCt/h*pg/ml was 7675.9, the mean Cmax (pg/ml) was 664.6, the mean tmax was 1.9 h.

Example 18

Formulations with a prolonged release coating were produced having the composition of Table 39.

TABLE 39

| | Formulation | |
|---|---|---|
| | A | B |
| Ingredient | amount per capsule (mg) | amount per capsule (mg) |
| Microcrystalline cellulose (MCC) spheres | 44.89 | 44.83 |
| Hydromorphone hydrochloride | 3.00 | 3.00 |
| Naloxone hydrochloride dihydrate | 1.65 | 1.65 |
| Hydroxypropyl methylcellulose, polyethylene glycol film coating concentrate (Opadry YS-1-7006, Clear) HS | 1.63 | 1.68 |
| Aqueous ethylcellulose dispersion (Surelease) | 4.66 | 6.04 |
| Polyvinyl alcohol-polyethylene glycol graft copolymer (Kollicoat IR) HS | 0.34 | 0.45 |
| Silicon dioxide NF (Syloid 244FP) NF | 0.00 | 0.29 |
| Purified Water USP | q.s. | q.s. |
| Total | ~56 | ~58 |

For Formulation A, a solution is produced from hydromorphone and naloxone dissolved in water, Opadry Clear® YS-1-7006. This solution is then sprayed on to a microcrystalline cellulose (MXX) beads in a fluid bed dryer with a Wurster column. This produces an immediate-release (IR) bead. The IR bead is then sprayed with Surelease dispersion and Kollicoat IR in a fluid bed dryer with a Wurster column, a prolonged release bead is thus formed. The prolonged release beads are then sprayed with Opadry Clear® YS-1-7006 aqueous solution. Opadry protects the beads from agglomeration. The beads are then encapsulated.

For Formulation B, a solution is produced from hydromorphone and naloxone dissolved in water, Opadry Clear® YS-1-7006. This solution is then sprayed on to a microcrystalline cellulose (MXX) beads in a fluid bed dryer with a Wurster column. This produces an immediate-release (IR) bead. The IR bead is then sprayed with Surelease dispersion and Kollicoat IR in a fluid bed dryer with a Wurster column, a prolonged release bead is thus formed. The prolonged release beads are then sprayed with Opadry Clear® YS-1-7006 aqueous solution. Opadry protects the beads from agglomeration. The beads are then cured in a fluid bed dryer at 60° C. outlet temperature with water spraying for 2 hours. The cured beads are then coated with Opadry Clear coating and mixed with silicon dioxide before encapsulation.

Formulations A and B were then analyzed as regards in vitro release behavior using the USP basket method at 100 rpm in 000 ml simulated gastric fluid (SGF) dissolution medium (0.1 N HCl with pH 1.2) without enzyme. Aliquots of the dissolution media are withdrawn at the respective time points and analyzed by HPLC/UV.

The in vitro release data is indicated as percentage (based on the label content of active tested) in table 40. The values in the brackets indicate the range observed when measuring six tablets.

TABLE 40

| | Formulation | | | |
|---|---|---|---|---|
| | A | | B | |
| | Dissolution medium | | | |
| Active | 0.1N HCl pH1.2 | | 0.1N HCl pH1.2 | |
| tested | Hm | Nal | Hm | Nal |
| 1 h | 3 (2-3) | 4 (3-5) | 14 (13-15) | 15 (14-17) |
| 2 h | 6 (5-7) | 7 (7-8) | 40 (39-42) | 42 (41-43) |
| 4 h | 20 (19-22) | 12 (12-14) | 68 (68-69) | 69 (68-69) |
| 8 h | 67 (65-68) | 65 (63-66) | 90 (89-90) | 89 (88-90) |
| 12 h | 87 (87-88) | 85 (84-86) | 97 (97-98) | 97 (96-97) |
| 16 h | 96 (95-96) | 94 (93-95) | 100 (99-101) | 100 (99-101) |
| 24 h | 102 (101-102) | 101 (100-101) | 103 (101-104) | 103 (101-104) |

Hm = hydromorphone HCl,
Nal = naloxone HCl;
values are the average of 6 measurements,
values in the brackest indicate the observed ranges.

The controlled release bead dosage forms from Formulation A and Formulation B were tested against Hydromorph Contin™ in single-dose pK study conducted under fasted conditions. A summary of the results is shown in FIG. 2.

The results showed that all three formulations are bioequivalent. Formulation A is preferred since it resulted in a tmax closest to that of the reference formulation.

Thus, when the dosage form according to the invention is in the form of a controlled release bead dosage form, it can be preferred that: (i) it is not subjected to a curing step during manufacture, and (ii) it contains a weight ratio of hydromorphone to naloxone of 2:1 (this was confirmed in a randomized, double-blind, placebo-controlled, dose-ranging crossover study evaluating the effect of naloxone on intravenous hydromorphone abuse potential in healthy, non-dependent, opioid-experienced recreational drug users).

Example 19

This example shows an aqueous method of manufacturing. Granules of the composition as shown in Table 41 were manufactured.

TABLE 41

| | Granules | |
|---|---|---|
| Ingredient | F888/49 Amount (mg) | F888/55 Amount (mg) |
| Hydromorphone HCl | 2.0 | |
| Naloxone HCl | | 4.0 |
| Ethyl cellulose | 32.0 | 32.0 |
| Eudragit NE 40 D* | 23.0 | 23.0 |
| Lactose Anhydrous | 29.7 | 29.7 |
| Purified Water** | 11.5 | 11.5 |
| Glycerol Monostearate 40-55% | 2.3 | 2.3 |
| Hypromellose 5.2 mPas*** | 0.23 | 0.23 |
| Talc | 5.8 | 5.8 |
| Total*** | 95.0 | 97.0 |

*The amount indicated refers to the amount of solids used
**Water was removed from the granules by drying
***The amount refers to the weight of the granules without water
The amounts refer to Hydromorphone HCl and Naloxone HCl.

To obtain granules, Hypromellose 5.2 mPas was mixed with purified water until fully dissolved using a Silverson high shear mixer. Then, whilst heating to 60° C. and maintaining mixing, glycerol monostearate 40-55% was added. When the mixture reached 60° C., heating was discontinued the mixture was cooled to <54° C. with mixing being continued. Talc was added to the Eudragit NE 40 D dispersion while stirring with a Heidolph paddle stirrer until fully dispersed. Then the hypromellose/glycerol monostearate dispersion was added to the Eudragit NE 40 D/talc dispersion with paddle stirring until a homogenous mixture was obtained. Stirring was maintained.

Ethyl cellulose, lactose, and hydromorphone hydrochloride or naloxone hydrochloride were placed into an Aeromatic Fielder S2 fluid bed granulator.

The conditions for fluidised bed granulation were as follows:

Apparatus: Aeromatic-Fielder S2 fluid bed granulator
Nozzle diameter: 1.8 mm
Spraying pressure: filter chamber
Air velocity (m/s): 4-6
Inlet Air temperature (° C.): 30-40
Spray rate (g/min×kg): 30-50
Spray time (min): 120
Product temperature (° C.): 24-26

The granules were then dried in the fluidized bed granulator at <28° C. for 20-30 minutes until the moisture content was below 2% w/w. The granules were then sieved using a Demi Finex sieve shaker with a mesh size of 1 mm. Subsequently the granules were milled using a Quadro Comil 197S.

Granules were then pressed into tablets (see Table 42).

TABLE 42

| | Tablets | |
|---|---|---|
| Ingredient | F888/72 Amount (mg) | F888/83 Amount (mg) |
| Hydromorphone HCl Granules F888/49 | 95.0 | |
| Naloxone HCl Granules F888/55 | | 97.0 |
| Hydromorphone HCl | | 2.0 |
| Naloxone HCl | 4.0 | |
| Magnesium stearate | 1.0 | 1.0 |
| Total | 100 | 100 |

The amounts refer to Hydromorphone HCl and Naloxone HCl.

For obtaining the tablets, granules were blended with hydromorphone HCl, or naloxone HCl and magnesium stearate using an Apex cone blender. Tablets were obtained by compressing the blend using a Kilian rotary tablet press at a tablet speed of up to 50,000 tablets/hr.

Tablet F888/72 was cured in a convection oven at 60° C. for 1 h. The cured tablet was labeled F892/15.

Tablet F888/83 was cured at 60° C. for 1 h. The cured tablet was labeled F892/16.

Tablets F892/15 and F892/16 were further subjected to prolonged storage under ICH stressed conditions, namely storage at 25° C./60% RH for 7 months.

For F892/15 the amount of total related substances was 0.28%. The amount of hydromorphone N-oxide was 0.18%.

For F892/16 the amount of total related substances was 0.56%. The amount of hydromorphone N-oxide was 0.14%. The amount of noroxymorphone was 0.10%. The amount of naloxone N-oxide was 0.06%.

Some embodiments of the invention relate to:

1. An oral prolonged release pharmaceutical composition comprising at least:
   a) at least one prolonged release material;
   b) at least hydromorphone or a pharmaceutically acceptable salt or derivative thereof and naloxone or a pharmaceutically acceptable salt or derivative thereof, and
   c) wherein the prolonged release pharmaceutical composition is heat treated.

2. A pharmaceutical composition according to 1, wherein the at least one prolonged release material and hydromorphone or a pharmaceutically acceptable salt or derivative thereof and naloxone or a pharmaceutically acceptable salt or derivative thereof are combined such that a prolonged release matrix is formed.

3. A pharmaceutical composition according to 1 or 2, wherein a prolonged release coating is disposed on the active ingredients hydromorphone or a pharmaceutically acceptable salt or derivative thereof and naloxone or a pharmaceutically acceptable salt or derivative thereof.

4. A pharmaceutical composition according to 1, 2 or 3, wherein hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

5. Pharmaceutical composition according to 1, 2, 3 or 4, wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oils and waxes.

6. Pharmaceutical composition according to 5, wherein the prolonged release material is a cellulose ether, a (meth)acrylic based (co)polymer and/or a fatty alcohol.

7. Pharmaceutical composition according to 6, wherein prolonged release material is a neutral (meth)acrylic based (co)polymer, a hydrophobic cellulose ether and/or a fatty alcohol.

8. Pharmaceutical composition according to any of 1, 2, 3, 4, 5, 6 or 7 comprising at least:
   a) at least one (meth)acrylic acid (co)polymer, preferably at least one neutral (meth)acrylic acid (co)polymer such as Eudragit® NE as prolonged release material;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release material to form a prolonged release matrix 9. Pharmaceutical composition according to any of 1, 2, 3, 4, 5, 6 or 7, comprising at least:
   a) at least one cellulose ether, preferably at least one hydrophobic cellulose ether such as ethyl cellulose as prolonged release material;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release material to form a prolonged release matrix.

10. Pharmaceutical composition according to any of 1, 2, 3, 4, 5, 6 or 7, comprising at least:
    a) at least one fatty alcohol as prolonged release material;
    b) at least hydromorphone or a pharmaceutically acceptable salt or derivative thereof and naloxone or a pharmaceutically acceptable salt or derivative thereof, wherein
    c) hydromorphone or a pharmaceutically acceptable salt or derivative thereof and naloxone or a pharmaceutically acceptable salt or derivative thereof are combined with said prolonged release material to form a prolonged release matrix.

11. Pharmaceutical composition according to any of 1, 2, 3, 4, 5, 6 or 7, comprising at least:
    a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
    b) at least hydromorphone or a pharmaceutically acceptable salt or derivative thereof and naloxone or a pharmaceutically acceptable salt or derivative thereof, wherein
    c) hydromorphone or a pharmaceutically acceptable salt or derivative thereof and naloxone or a pharmaceutically acceptable salt or derivative thereof are combined with said prolonged release materials to form a prolonged release matrix.

12. Pharmaceutical composition according to any of 1, 2, 3, 4, 5, 6 or 7, comprising at least:
    a) at least one (meth)acrylic acid (co)polymer, preferably at least one neutral (meth)acrylic acid (co)polymer such as Eudragit® NE and at least one fatty alcohol as prolonged release materials;
    b) at least hydromorphone or a pharmaceutically acceptable salt or derivative thereof and naloxone or a pharmaceutically acceptable salt or derivative thereof, wherein
    c) hydromorphone or a pharmaceutically acceptable salt or derivative thereof and naloxone or a pharmaceutically acceptable salt or derivative thereof are combined with said prolonged release materials to form a prolonged release matrix.

13. Pharmaceutical composition according to any of 1, 2, 3, 4, 5, 6 or 7, comprising at least:
   a) at least one cellulose ether, preferably at least one hydrophobic cellulose ether such as ethyl cellulose and at least one fatty alcohol as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

14. Pharmaceutical composition according to any of 1, 2, 3, 4, 5, 6 or 7, comprising at least:
   a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

15. Pharmaceutical composition according to any of 1, 2, 3, 4, 5, 6, 7, 8, 9, 10, 11, 12, 13 or 14, wherein the pharmaceutical composition comprises additionally at least one filler, at least one lubricant, at least one binder, at least one release rate modifiers, at least one spheronising agent and/or at least one anti-tacking agent 16. Pharmaceutical composition according to 15, wherein said filler is anhydrous lactose.

17. Pharmaceutical composition according to 15 or 16, wherein magnesium stearate and/or talc are used as lubricants.

18. Pharmaceutical composition according to 15, 16 or 17, wherein hydroxypropyl cellulose is used as binder.

19. Pharmaceutical composition according to 15, 16, 17 or 18, wherein hydroxypropylmethyl cellulose, an anionic (meth)acrylic acid (co)polymer such as Eudragit RSPO and/or Xanthan gum are used release rate modifiers.

20. Pharmaceutical composition according to 15, 16, 17, 18 or 19, wherein microcrystalline cellulose is used as spheronising agent.

21. Pharmaceutical composition according to any of 1, 2, 3, 4, 5, 6, 7, 8, 9, 10, 11, 12, 13, 14, 15, 16, 17, 18, 19 or 20, wherein heat treatment takes place at a temperature in the range of about 30° C. to about 95° C. and for a time in the range of about 10 min to about 3 hours.

22. Pharmaceutical composition according to any of 1, 2, 3, 4, 5, 6, 7, 8, 9, 10, 11, 12, 13, 14, 15, 16, 17, 18, 19, 20 or 21, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:
   at 1 h: 5 to 45% by weight of the pharmaceutically active agents,
   at 2 h: 15 to 55% by weight of the pharmaceutically active agents,
   at 3 h: 30 to 70% by weight of the pharmaceutically active agents,
   at 4 h: 35 to 75% by weight of the pharmaceutically active agents,
   at 6 h: 40 to 80% by weight of the pharmaceutically active agents,
   at 8 h: 50 to 90% by weight of the pharmaceutically active agents,
   at 10 h: 60 to 100% by weight of the pharmaceutically active agents,
   at 12 h: 65 to 100% by weight of the pharmaceutically active agents.

23. Pharmaceutical composition according to any of 1, 2, 3, 4, 5, 6, 7, 8, 9, 10, 11, 12, 13, 14, 15, 16, 17, 18, 19, 20, 21 or 22, wherein the ratio of the amount of the pharmaceutically active agents released after 0.5, 1 or 2 hours of in vitro dissolution of the dosage form in 500 of 900 ml of Simulated Gastric Fluid with up to 40% ethanol using the Ph. Eur. paddle method at 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

24. Pharmaceutical composition according to any of 1, 2, 3, 4, 5, 6, 7, 8, 9, 10, 11, 12, 13, 14, 15, 16, 17, 18, 19, 20, 21, 22 or 23, comprising at least:
   a) at least one prolonged release material;
   b) at least hydromorphone or a pharmaceutically acceptable salt or derivative thereof and naloxone or a pharmaceutically acceptable salt or derivative thereof; and wherein
   c) the pharmaceutical composition after storage under stressed conditions releases the pharmaceutically active agents with substantially the same release rate as before subjecting the pharmaceutical composition to stressed conditions.

25. Pharmaceutical composition according to any of 1, 2, 3, 4, 5, 6, 7, 8, 9, 10, 11, 12, 13, 14, 15, 16, 17, 18, 19, 20, 21, 22, 23 or 24 composition comprising at least:
   a) at least one prolonged release material;
   b) at least hydromorphone or a pharmaceutically acceptable salt or derivative thereof and naloxone or a pharmaceutically acceptable salt or derivative thereof; and wherein
   c) the pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

26. An oral prolonged release pharmaceutical composition comprising at least:
   a) at least one prolonged release material;
   b) at least hydromorphone or a pharmaceutically acceptable salt or derivative thereof and naloxone or a pharmaceutically acceptable salt or derivative thereof with hydromorphone or a pharmaceutically acceptable salt or derivative thereof and naloxone or a pharmaceutically acceptable salt or derivative thereof being present in the pharmaceutical composition in a weight ratio in a range of about 2:1 to about 1:3, preferably of about 2:1, about 1:1, about 1:2 or about 1:3.

27. Pharmaceutical composition according to 26, wherein the prolonged release pharmaceutical composition is heat treated.

28. Pharmaceutical composition according to 26 or 27, wherein the at least one prolonged release material and hydromorphone or a pharmaceutically acceptable salt or derivative thereof and naloxone or a pharmaceutically acceptable salt or derivative thereof are combined such that a prolonged release matrix is formed.

29. Pharmaceutical composition according to 26, 27 or 28, wherein a prolonged release coating is disposed on the active ingredients hydromorphone or a pharmaceutically acceptable salt or derivative thereof and naloxone or a pharmaceutically acceptable salt or derivative thereof.

30. Pharmaceutical composition according to 26, 27, 28 or 29, wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

31. Pharmaceutical composition according to 30, wherein the prolonged release material is a cellulose ether, a (meth) acrylic based (co)polymer and/or a fatty alcohol.

32. Pharmaceutical composition according to 31, wherein prolonged release material is a neutral (meth)acrylic based (co)polymer, a hydrophobic cellulose ether and/or a fatty alcohol.

33. Pharmaceutical composition according to any of 26, 27, 28, 29, 30, 31 or 32, comprising at least:
   a) at least one (meth)acrylic acid (co)polymer, preferably at least one neutral (meth)acrylic acid (co)polymer such as Eudragit® NE as prolonged release material;
   b) at least hydromorphone or a pharmaceutically acceptable salt or derivative thereof and naloxone or a pharmaceutically acceptable salt or derivative thereof, and wherein
   c) hydromorphone or a pharmaceutically acceptable salt or derivative thereof and naloxone or a pharmaceutically acceptable salt or derivative thereof are combined with said prolonged release material to form a prolonged release matrix 34. Pharmaceutical composition according to any of 26, 27, 28, 29, 30, 31 or 32, comprising at least:
   a) at least one cellulose ether, preferably at least one hydrophobic cellulose ether such as ethyl cellulose as prolonged release material;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release material to form a prolonged release matrix.

35. Pharmaceutical composition according to any of 26, 27, 28, 29, 30, 31 or 32, comprising at least:
   a) at least one fatty alcohol as prolonged release material;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release material to form a prolonged release matrix.

36. Pharmaceutical composition according to any of 26, 27, 28, 29, 30, 31 or 32, comprising at least:
   a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

37. Pharmaceutical composition according to any of 26, 27, 28, 29, 30, 31 or 32, comprising at least:
   a) at least one (meth)acrylic acid (co)polymer, preferably at least one neutral (meth)acrylic acid (co)polymer such as Eudragit® NE and at least one fatty alcohol as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

38. Pharmaceutical composition according to any of 26, 27, 28, 29, 30, 31 or 32, comprising at least:
   a) at least one cellulose ether, preferably at least one hydrophobic cellulose ether such as ethyl cellulose and at least one fatty alcohol as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

39. Pharmaceutical composition according to any of 26, 27, 28, 29, 30, 31 or 32, comprising at least:
   a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;
   b) at least hydromorphone or a pharmaceutically acceptable salt or derivative thereof and naloxone or a pharmaceutically acceptable salt or derivative thereof, wherein
   c) hydromorphone or a pharmaceutically acceptable salt or derivative thereof and naloxone or a pharmaceutically acceptable salt or derivative thereof are combined with said prolonged release materials to form a prolonged release matrix.

40. Pharmaceutical composition according to any of 26, 27, 28, 29, 30, 31, 32, 33, 34, 35, 36, 37, 38 or 39, wherein the pharmaceutical composition comprises additionally at least one filler, at least one lubricant, at least one binder, at least one release rate modifiers, at least one spheronising agent and/or at least one anti-tacking agent 41. Pharmaceutical composition according to 40, wherein said filler is anhydrous lactose.

42. Pharmaceutical composition according to 40 or 41, wherein magnesium stearate and/or talc are used as lubricants.

43. Pharmaceutical composition according to 40, 41 or 42, wherein hydroxypropyl cellulose is used as binder.

44. Pharmaceutical composition according to 40, 41, 42 or 43, wherein hydroxypropylmethyl cellulose, an anionic (meth)acrylic acid (co)polymer such as Eudragit RSPO and/or Xanthan gum are used release rate modifiers.

45. Pharmaceutical composition according to 40, 41, 42, 43 or 44, wherein microcrystalline cellulose is used as spheronising agent.

46. Pharmaceutical composition according to any of 26, 27, 28, 29, 30, 31, 32, 33, 34, 35, 36, 37, 38, 38, 39, 40, 41, 42, 43, 44 or 45, wherein heat treatment takes place at a temperature in the range of about 30° C. to about 95° C. and for a time in the range of about 10 min to about 3 hours.

47. Pharmaceutical composition according to any of 26, 27, 28, 29, 30, 31, 32, 33, 34, 35, 36, 37, 38, 38, 39, 40, 41, 42, 43, 44, 45 or 46, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:

at 1 h: 5 to 45% by weight of the pharmaceutically active agents,
at 2 h: 15 to 55% by weight of the pharmaceutically active agents,
at 3 h: 30 to 70% by weight of the pharmaceutically active agents,
at 4 h: 35 to 75% by weight of the pharmaceutically active agents,
at 6 h: 40 to 80% by weight of the pharmaceutically active agents,
at 8 h: 50 to 90% by weight of the pharmaceutically active agents,
at 10 h: 60 to 100% by weight of the pharmaceutically active agents,
at 12 h: 65 to 100% by weight of the pharmaceutically active agents.

48. Pharmaceutical composition according to any of 26, 27, 28, 29, 30, 31, 32, 33, 34, 35, 36, 37, 38, 38, 39, 40, 41, 42, 43, 44, 45, 46 or 47, wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 or 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

49. Pharmaceutical composition according to any of 26, 27, 28, 29, 30, 31, 32, 33, 34, 35, 36, 37, 38, 38, 39, 40, 41, 42, 43, 44, 45, 46, 47 or 48, comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions releases the pharmaceutically active agents with substantially the same release rate as before subjecting the pharmaceutical composition to stressed conditions.

50. Pharmaceutical composition according to any of 26, 27, 28, 29, 30, 31, 32, 33, 34, 35, 36, 37, 38, 38, 39, 40, 41, 42, 43, 44, 45, 46, 47, 48 or 49, comprising at least:

a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

51. An oral prolonged release pharmaceutical composition comprising at least:

a) at least one prolonged release material;
b) at least hydromorphone or a pharmaceutically acceptable salt or derivative thereof and naloxone or a pharmaceutically acceptable salt or derivative thereof, and wherein
c) the at least one prolonged release material and hydromorphone or a pharmaceutically acceptable salt or derivative thereof and naloxone or a pharmaceutically acceptable salt or derivative thereof are combined such that a prolonged release matrix is formed.

52. A pharmaceutical composition according to 51, wherein the prolonged release pharmaceutical composition is heat treated.

53. A pharmaceutical composition according to 51 or 52, wherein a prolonged release coating is disposed on the active ingredients hydromorphone or a pharmaceutically acceptable salt or derivative thereof and naloxone or a pharmaceutically acceptable salt or derivative thereof.

54. A pharmaceutical composition according to 51, 52 or 53, wherein hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

55. Pharmaceutical composition according to 51, 52, 53 or 54 wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

56. Pharmaceutical composition according to 55, wherein the prolonged release material is a cellulose ether, a (meth) acrylic based (co)polymer and/or a fatty alcohol.

57. Pharmaceutical composition according to 56, wherein prolonged release material is a neutral (meth)acrylic based (co)polymer, a hydrophobic cellulose ether and/or a fatty alcohol.

58. Pharmaceutical composition according to any of 51, 52, 53, 54, 55, 56 or 57 comprising at least:

a) at least one (meth)acrylic acid (co)polymer, preferably at least one neutral (meth)acrylic acid (co)polymer such as Eudragit® NE as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix 59. Pharmaceutical composition according to any of 51, 52, 53, 54, 55, 56, 57 or 58 comprising at least:
a) at least one cellulose ether, preferably at least one hydrophobic cellulose ether such as ethyl cellulose as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

60. Pharmaceutical composition according to any of 51, 52, 53, 54, 55, 56, 57 or 58 comprising at least:
a) at least one fatty alcohol as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

61. Pharmaceutical composition according to any of 51, 52, 53, 54, 55, 56, 57 or 58 comprising at least:
a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

62. Pharmaceutical composition according to any of 51, 52, 53, 54, 55, 56, 57 or 58 comprising at least:
a) at least one (meth)acrylic acid (co)polymer, preferably at least one neutral (meth)acrylic acid (co)polymer such as Eudragit® NE and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

63. Pharmaceutical composition according to any of 49, 50, 51, 52, 53, 54 or 55, comprising at least:
a) at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

64. Pharmaceutical composition according to any of 51, 52, 53, 54, 55, 56, 57 or 58 comprising at least:
a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

65. Pharmaceutical composition according to any of 51, 52, 53, 54, 55, 56, 57, 58, 59, 60, 61, 62, 63 or 64 wherein the pharmaceutical composition comprises additionally at least one filler, at least one lubricant, at least one binder, at least one release rate modifiers, at least one spheronising agent and/or at least one anti-tacking agent 66. Pharmaceutical composition according to 65, wherein said filler is anhydrous lactose.

67. Pharmaceutical composition according to 65 or 66, wherein magnesium stearate and/or talc are used as lubricants.

68. Pharmaceutical composition according to 65, 66 or 67, wherein hydroxypropyl cellulose is used as binder.

69. Pharmaceutical composition according to 65, 66, 67 or 68, wherein hydroxypropylmethyl cellulose, an anionic (meth)acrylic acid (co)polymer such as Eudragit RSPO and/or Xanthan gum are used release rate modifiers.

70. Pharmaceutical composition according to 65, 66, 67, 68, 68 or 69, wherein microcrystalline cellulose is used as spheronising agent.

71. Pharmaceutical composition according to any of 51, 52, 53, 54, 55, 56, 57, 58, 59, 60, 61, 62, 63, 64, 65, 66, 67, 68, 69 or 70, wherein heat treatment takes place at a temperature in the range of about 30° C. to about 95° C. and for a time in the range of about 10 min to about 3 hours.

72. Pharmaceutical composition according to any of 51, 52, 53, 54, 55, 56, 57, 58, 59, 60, 61, 62, 63, 64, 65, 66, 67, 68, 69, 70 or 71, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:

at 1 h: 5 to 45% by weight of the pharmaceutically active agents,
at 2 h: 15 to 55% by weight of the pharmaceutically active agents,
at 3 h: 30 to 70% by weight of the pharmaceutically active agents,
at 4 h: 35 to 75% by weight of the pharmaceutically active agents,
at 6 h: 40 to 80% by weight of the pharmaceutically active agents,
at 8 h: 50 to 90% by weight of the pharmaceutically active agents,
at 10 h: 60 to 100% by weight of the pharmaceutically active agents,
at 12 h: 65 to 100% by weight of the pharmaceutically active agents.

73. Pharmaceutical composition according to any of 51, 52, 53, 54, 55, 56, 57, 58, 59, 60, 61, 62, 63, 64, 65, 66, 67, 68, 69, 70, 71 or 72 wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 or 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

74. Pharmaceutical composition according to any of 51, 52, 53, 54, 55, 56, 57, 58, 59, 60, 61, 62, 63, 64, 65, 66, 67, 68, 69, 70, 71, 72 or 73, comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions releases the pharmaceutically active agents with substantially the same release rate as before subjecting the pharmaceutical composition to stressed conditions.

75. Pharmaceutical composition according to any of 51, 52, 53, 54, 55, 56, 57, 58, 59, 60, 61, 62, 63, 64, 65, 66, 67, 68, 69, 70, 71, 72, 73 or 74, composition comprising at least:
a) at least one prolonged release material;
b) at least hydromorphone or a pharmaceutically acceptable salt or derivative thereof and naloxone or a pharmaceutically acceptable salt or derivative thereof; and wherein
c) the pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

76. An oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof, and wherein
c) the pharmaceutical composition provides alcohol resistance.

77. A pharmaceutical composition according to 76, wherein the prolonged release pharmaceutical composition is heat treated.

78. A pharmaceutical composition according to 76 or 77, wherein the at least one prolonged release material and hydromorphone or a pharmaceutically acceptable salt or derivative thereof and naloxone or a pharmaceutically acceptable salt or derivative thereof are combined such that a prolonged release matrix is formed.

79. A pharmaceutical composition according to 76, 77 or 78, wherein a prolonged release coating is disposed on the active ingredients hydromorphone or a pharmaceutically acceptable salt or derivative thereof and naloxone or a pharmaceutically acceptable salt or derivative thereof.

80. A pharmaceutical composition according to 76, 77, 78 or 79, wherein hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

81. Pharmaceutical composition according to 76, 77, 78, 79 or 80 wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

82. Pharmaceutical composition according to 81, wherein the prolonged release material is a cellulose ether, a (meth) acrylic based (co)polymer and/or a fatty alcohol.

83. Pharmaceutical composition according to 82, wherein prolonged release material is a neutral (meth)acrylic based (co)polymer, a hydrophobic cellulose ether and/or a fatty alcohol.

84. Pharmaceutical composition according to any of 76, 77, 78, 79, 80, 81, 82 or 83, comprising at least:
a) at least one (meth)acrylic acid (co)polymer, preferably at least one neutral (meth)acrylic acid (co)polymer such as Eudragit® NE as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix 85. Pharmaceutical composition according to any of 76, 77, 78, 79, 80, 81, 82 or 83, comprising at least:
a) at least one cellulose ether, preferably at least one hydrophobic cellulose ether such as ethyl cellulose as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

86. Pharmaceutical composition according to any of 76, 77, 78, 79, 80, 81, 82 or 83, comprising at least:

a) at least one fatty alcohol as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

87. Pharmaceutical composition according to any of 76, 77, 78, 79, 80, 81, 82 or 83, comprising at least:
a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

88. Pharmaceutical composition according to any of 76, 77, 78, 79, 80, 81, 82 or 83, comprising at least:
a) at least one (meth)acrylic acid (co)polymer, preferably at least one neutral (meth)acrylic acid (co)polymer such as Eudragit® NE and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

89. Pharmaceutical composition according to any of 76, 77, 78, 79, 80, 81, 82 or 83, comprising at least:
a) at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

90. Pharmaceutical composition according to any of 76, 77, 78, 79, 80, 81, 82 or 83, comprising at least:
a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

91. Pharmaceutical composition according to any of 76, 77, 78, 79, 80, 81, 82, 83, 84, 85, 86, 87, 88, 89 or 90 wherein the pharmaceutical composition comprises additionally at least one filler, at least one lubricant, at least one binder, at least one release rate modifiers, at least one spheronising agent and/or at least one anti-tacking agent 92. Pharmaceutical composition according to 91, wherein said filler is anhydrous lactose.

93. Pharmaceutical composition according to 91 or 92, wherein magnesium stearate and/or talc are used as lubricants.

94. Pharmaceutical composition according to 91, 92 or 93, wherein hydroxypropyl cellulose is used as binder.

95. Pharmaceutical composition according to 91, 92, 93 or 94, wherein hydroxypropylmethyl cellulose, an anionic (meth)acrylic acid (co)polymer such as Eudragit RSPO and/or Xanthan gum are used release rate modifiers.

96. Pharmaceutical composition according to 91, 92, 93, 94 or 95, wherein microcrystalline cellulose is used as spheronising agent.

97. Pharmaceutical composition according to any of 76, 77, 78, 79, 80, 81, 82, 83, 84, 85, 86, 87, 88, 89, 90, 91, 92, 93, 94, 95 or 96 wherein heat treatment takes place at a temperature in the range of about 30° C. to about 95° C. and for a time in the range of about 10 min to about 3 hours.

98. Pharmaceutical composition according to any of 76, 77, 78, 79, 80, 81, 82, 83, 84, 85, 86, 87, 88, 89, 90, 91, 92, 93, 94, 95, 96 or 97, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:
at 1 h: 5 to 45% by weight of the pharmaceutically active agents,
at 2 h: 15 to 55% by weight of the pharmaceutically active agents,
at 3 h: 30 to 70% by weight of the pharmaceutically active agents,
at 4 h: 35 to 75% by weight of the pharmaceutically active agents,
at 6 h: 40 to 80% by weight of the pharmaceutically active agents,
at 8 h: 50 to 90% by weight of the pharmaceutically active agent
at 10 h: 60 to 100% by weight of the pharmaceutically active agents,
at 12 h: 65 to 100% by weight of the pharmaceutically active agents.

99. Pharmaceutical composition according to any of 76, 77, 78, 79, 80, 81, 82, 83, 84, 85, 86, 87, 88, 89, 90, 91, 92, 93, 94, 95, 96, 97 or 98, wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 or 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

100. Pharmaceutical composition according to any of 76, 77, 78, 79, 80, 81, 82, 83, 84, 85, 86, 87, 88, 89, 90, 91, 92, 93, 94, 95, 96, 97, 98 or 99, comprising at least:
 a) at least one prolonged release material;
 b) at least hydromorphone or a pharmaceutically acceptable salt or derivative thereof and naloxone or a pharmaceutically acceptable salt or derivative thereof; and wherein
 c) the pharmaceutical composition after storage under stressed conditions releases the pharmaceutically active agents with substantially the same release rate as before subjecting the pharmaceutical composition to stressed conditions.

101. Pharmaceutical composition according to any of 76, 77, 78, 79, 80, 81, 82, 83, 84, 85, 86, 87, 88, 89, 90, 91, 92, 93, 94, 95, 96, 97, 98, 99 or 100, comprising at least:
 a) at least one prolonged release material;
 b) at least hydromorphone or a pharmaceutically acceptable salt or derivative thereof and naloxone or a pharmaceutically acceptable salt or derivative thereof; and wherein
 c) the pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

102. An oral prolonged release pharmaceutical composition comprising at least:
 a) at least one prolonged release material;
 b) at least hydromorphone or a pharmaceutically acceptable salt or derivative thereof and naloxone or a pharmaceutically acceptable salt or derivative thereof; and wherein the
 c) pharmaceutical composition after storage under stressed conditions releases the pharmaceutically active agents with substantially the same release rate as before subjecting the pharmaceutical composition to stressed conditions.

103. A pharmaceutical composition according to 102, wherein the prolonged release pharmaceutical composition is heat treated.

104. A pharmaceutical composition according to 102 or 103, wherein the at least one prolonged release material and hydromorphone or a pharmaceutically acceptable salt or derivative thereof and naloxone or a pharmaceutically acceptable salt or derivative thereof are combined such that a prolonged release matrix is formed.

105. A pharmaceutical composition according to 102, 103 or 104, wherein a prolonged release coating is disposed on the active ingredients hydromorphone or a pharmaceutically acceptable salt or derivative thereof and naloxone or a pharmaceutically acceptable salt or derivative thereof.

106. A pharmaceutical composition according to 102, 103, 104 or 105, wherein hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

107. Pharmaceutical composition according to 102, 103, 104, 105 or 106, wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

108. Pharmaceutical composition according to 107, wherein the prolonged release material is a cellulose ether, a (meth)acrylic based (co)polymer and/or a fatty alcohol.

109. Pharmaceutical composition according to 108, wherein prolonged release material is a neutral (meth)acrylic based (co)polymer, a hydrophobic cellulose ether and/or a fatty alcohol.

110. Pharmaceutical composition according to any of 102, 103, 104, 105, 106, 107, 108 or 109, comprising at least:
 a) at least one (meth)acrylic acid (co)polymer, preferably at least one neutral (meth)acrylic acid (co)polymer such as Eudragit® NE as prolonged release material;
 b) at least hydromorphone or a pharmaceutically acceptable salt or derivative thereof and naloxone or a pharmaceutically acceptable salt or derivative thereof, wherein
 c) hydromorphone or a pharmaceutically acceptable salt or derivative thereof and naloxone or a pharmaceutically acceptable salt or derivative thereof are combined with said prolonged release material to form a prolonged release matrix 111. Pharmaceutical composition according to any of 102, 103, 104, 105, 106, 107, 108 or 109, comprising at least:
 a) at least one cellulose ether, preferably at least one hydrophobic cellulose ether such as ethyl cellulose as prolonged release material;
 b) at least hydromorphone or a pharmaceutically acceptable salt or derivative thereof and naloxone or a pharmaceutically acceptable salt or derivative thereof, wherein
 c) hydromorphone or a pharmaceutically acceptable salt or derivative thereof and naloxone or a pharmaceutically acceptable salt or derivative thereof are combined with said prolonged release material to form a prolonged release matrix.

112. Pharmaceutical composition according to any of 102, 103, 104, 105, 106, 107, 108 or 109, comprising at least:
 a) at least one fatty alcohol as prolonged release material;
 b) at least hydromorphone or a pharmaceutically acceptable salt or derivative thereof and naloxone or a pharmaceutically acceptable salt or derivative thereof, wherein
 c) hydromorphone or a pharmaceutically acceptable salt or derivative thereof and naloxone or a pharmaceutically acceptable salt or derivative thereof are combined with said prolonged release material to form a prolonged release matrix.

113. Pharmaceutical composition according to any of 102, 103, 104, 105, 106, 107, 108 or 109, comprising at least:
 a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
 b) at least hydromorphone or a pharmaceutically acceptable salt or derivative thereof and naloxone or a pharmaceutically acceptable salt or derivative thereof, wherein
 c) hydromorphone or a pharmaceutically acceptable salt or derivative thereof and naloxone or a pharmaceutically acceptable salt or derivative thereof are combined with said prolonged release materials to form a prolonged release matrix.

114. Pharmaceutical composition according to any of 102, 103, 104, 105, 106, 107, 108 or 109, comprising at least:

a) at least one (meth)acrylic acid (co)polymer, preferably at least one neutral (meth)acrylic acid (co)polymer such as Eudragit® NE and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

115. Pharmaceutical composition according to any of 102, 103, 104, 105, 106, 107, 108 or 109, comprising at least:
a) at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

116. Pharmaceutical composition according to any of 102, 103, 104, 105, 106, 107, 108 or 109, comprising at least:
a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release matrix materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

117. Pharmaceutical composition according to any of 102, 103, 104, 105, 106, 107, 108, 109, 111, 112, 113, 114, 115 or 116 wherein the pharmaceutical composition comprises additionally at least one filler, at least one lubricant, at least one binder, at least one release rate modifier, at least one spheronising agent and/or at least one anti-tacking agent 118. Pharmaceutical composition according to 117, wherein said filler is anhydrous lactose.

119. Pharmaceutical composition according to 117 or 118, wherein magnesium stearate and/or talc are used as lubricants.

120. Pharmaceutical composition according to 117, 118 or 119, wherein hydroxypropyl cellulose is used as binder.

121. Pharmaceutical composition according to 117, 118, 119 or 120, wherein hydroxypropylmethyl cellulose, an anionic (meth)acrylic acid (co)polymer such as Eudragit RSPO and/or Xanthan gum are used release rate modifiers.

122. Pharmaceutical composition according to 117, 118, 119, 120 or 121, wherein microcrystalline cellulose is used as spheronising agent.

123. Pharmaceutical composition according to any of 102, 103, 104, 105, 106, 107, 108, 109, 110, 111, 112, 113, 114, 115, 116, 117, 118, 119, 120, 121 or 122, wherein heat treatment takes place at a temperature in the range of about 30° C. to about 95° C. and for a time in the range of about 10 min to about 3 hours.

124. Pharmaceutical composition according to any of 102, 103, 104, 105, 106, 107, 108, 109, 110, 111, 112, 113, 114, 115, 116, 117, 118, 119, 120, 121, 122 or 123, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:
at 1 h: 5 to 45% by weight of the pharmaceutically active agents,
at 2 h: 15 to 55% by weight of the pharmaceutically active agents,
at 3 h: 30 to 70% by weight of the pharmaceutically active agents,
at 4 h: 35 to 75% by weight of the pharmaceutically active agents,
at 6 h: 40 to 80% by weight of the pharmaceutically active agents,
at 8 h: 50 to 90% by weight of the pharmaceutically active agents,
at 10 h: 60 to 100% by weight of the pharmaceutically active agents,
at 12 h: 65 to 100% by weight of the pharmaceutically active agents.

125. Pharmaceutical composition according to any of 102, 103, 104, 105, 106, 107, 108, 109, 110, 111, 112, 113, 114, 115, 116, 117, 118, 119, 120, 121, 122, 123 or 124, wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

126. Pharmaceutical composition according to any of 102, 103, 104, 105, 106, 107, 108, 109, 110, 111, 112, 113, 114, 115, 116, 117, 118, 119, 120, 121, 122, 123, 124 or 125, comprising at least:
a) at least one prolonged release material;
b) at least hydromorphone or a pharmaceutically acceptable salt or derivative thereof and naloxone or a pharmaceutically acceptable salt or derivative thereof; and wherein the
c) pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

127. An oral prolonged release pharmaceutical composition comprising at least:
a) at least one prolonged release material;
b) at least hydromorphone or a pharmaceutically acceptable salt or derivative thereof and naloxone or a pharmaceutically acceptable salt or derivative thereof; and wherein the c) pharmaceutical composition after storage under stressed conditions has less than 3% of total substances related to hydromorphone or a pharmaceutically acceptable salt or derivative thereof and/or related to naloxone or a pharmaceutically acceptable salt or derivative thereof.

128. Pharmaceutical composition according to 127, wherein the prolonged release pharmaceutical composition is heat treated.

129. A pharmaceutical composition according to 127 or 128, wherein the at least one prolonged release matrix material and hydromorphone or a the at least one prolonged release material and hydromorphone or a pharmaceutically acceptable salt or derivative thereof and naloxone or a pharmaceutically acceptable salt or derivative thereof are combined such that a prolonged release matrix is formed.

130. A pharmaceutical composition according to 127, 128 or 129, wherein a prolonged release coating is disposed on the active ingredients hydromorphone or a pharmaceutically acceptable salt or derivative thereof and naloxone or a pharmaceutically acceptable salt or derivative thereof.

131. A pharmaceutical composition according to 127, 128, 129 or 130, wherein hydromorphone or a pharmaceutically acceptable salt or derivative thereof and naloxone or a pharmaceutically acceptable salt or derivative thereof are present in the pharmaceutical composition in a weight ratio of about 2:1, about 1:1, about 1:2 or about 1:3.

132. Pharmaceutical composition according to 127, 128, 129, 130 or 131, wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

133. Pharmaceutical composition according to 132, wherein the prolonged release material is a cellulose ether, a (meth)acrylic based (co)polymer and/or a fatty alcohol.

134. Pharmaceutical composition according to 133, wherein prolonged release material is a neutral (meth)acrylic based (co)polymer, a hydrophobic cellulose ether and/or a fatty alcohol.

135. Pharmaceutical composition according to any of 127, 128, 129, 130, 131, 132, 133 or 134, comprising at least:
a) at least one (meth)acrylic acid (co)polymer, preferably at least one neutral (meth)acrylic acid (co)polymer such as Eudragit® NE as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix 136. Pharmaceutical composition according to any of 127, 128, 129, 130, 131, 132, 133 or 134, comprising at least:
a) at least one cellulose ether, preferably at least one hydrophobic cellulose ether such as ethyl cellulose as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

137. Pharmaceutical composition according to any of 127, 128, 129, 130, 131, 132, 133 or 134, comprising at least:
a) at least one fatty alcohol as prolonged release material;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release material to form a prolonged release matrix.

138. Pharmaceutical composition according to any of 127, 128, 129, 130, 131, 132, 133 or 134, comprising at least:
a) at least one (meth)acrylic acid (co)polymer, preferably at least one neutral (meth)acrylic acid (co)polymer such as Eudragit® NE and at least one cellulose ether, preferably at least one hydrophobic cellulose ether such as ethyl cellulose as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

139. Pharmaceutical composition according to any of 127, 128, 129, 130, 131, 132, 133 or 134, comprising at least:
a) at least one (meth)acrylic acid (co)polymer, preferably at least one neutral (meth)acrylic acid (co)polymer such as Eudragit® NE and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

140. Pharmaceutical composition according to any of 127, 128, 129, 130, 131, 132, 133 or 134, comprising at least:
a) at least one cellulose ether, preferably at least one hydrophobic cellulose ether such as ethyl cellulose and at least one fatty alcohol as prolonged release materials;
b) at least hydromorphone or a pharmaceutically acceptable salt or derivative thereof and naloxone or a pharmaceutically acceptable salt or derivative thereof, wherein
c) hydromorphone or a pharmaceutically acceptable salt or derivative thereof and naloxone or a pharmaceutically acceptable salt or derivative thereof are combined with said prolonged release materials to form a prolonged release matrix.

141. Pharmaceutical composition according to any of 127, 128, 129, 130, 131, 132, 133 or 134, comprising at least:
a) at least one (meth)acrylic acid (co)polymer, preferably at least one neutral (meth)acrylic acid (co)polymer such as Eudragit® NE, at least one cellulose ether, preferably at least one hydrophobic cellulose ether such as ethyl cellulose and at least one fatty alcohol as prolonged release materials;

b) at least hydromorphone or a pharmaceutically acceptable salt or derivative thereof and naloxone or a pharmaceutically acceptable salt or derivative thereof, wherein c) hydromorphone or a pharmaceutically acceptable salt or derivative thereof and naloxone or a pharmaceutically acceptable salt or derivative thereof are combined with said prolonged release materials to form a prolonged release matrix.

142. Pharmaceutical composition according to any of 127, 128, 129, 130, 131, 132, 133, 134, 135, 136, 137, 138, 139, 140, or 141 wherein the pharmaceutical composition comprises additionally at least one filler, at least one lubricant, at least one binder, at least one release rate modifier, at least one spheronising agent and/or at least one anti-tacking agent 143. Pharmaceutical composition according to 142, wherein said filler is anhydrous lactose.

144. Pharmaceutical composition according to 142 or 143, wherein magnesium stearate and/or talc are used as lubricants.

145. Pharmaceutical composition according to 142, 143 or 144, wherein hydroxypropyl cellulose is used as binder.

146. Pharmaceutical composition according to 142, 143, 144 or 145, wherein hydroxypropylmethyl cellulose, an anionic (meth)acrylic acid (co)polymer such as Eudragit RSPO and/or Xanthan gum are used release rate modifiers.

147. Pharmaceutical composition according to 142, 143, 144, 145 or 146, wherein microcrystalline cellulose is used as spheronising agent.

148. Pharmaceutical composition according to any of 127, 128, 129, 130, 131, 132, 133, 134, 135, 136, 137, 138, 139, 140, 141, 142, 143, 144, 145, 146, or 147 wherein heat treatment takes place at a temperature in the range of about 30° C. to about 95° C. and for a time in the range of about 10 min to about 3 hours 149. Pharmaceutical composition according to any of 127, 128, 129, 130, 131, 132, 133, 134, 135, 136, 137, 138, 139, 140, 141, 142, 143, 144, 145, 146, 147 or 148, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:

at 1 h: 5 to 45% by weight of the pharmaceutically active agents,
at 2 h: 15 to 55% by weight of the pharmaceutically active agents,
at 3 h: 30 to 70% by weight of the pharmaceutically active agents,
at 4 h: 35 to 75% by weight of the pharmaceutically active agents,
at 6 h: 40 to 80% by weight of the pharmaceutically active agents,
at 8 h: 50 to 90% by weight of the pharmaceutically active agents,
at 10 h: 60 to 100% by weight of the pharmaceutically active agents,
at 12 h: 65 to 100% by weight of the pharmaceutically active agents.

150. Pharmaceutical composition according to any of 127, 128, 129, 130, 131, 132, 133, 134, 135, 136, 137, 138, 139, 140, 141, 142, 143, 144, 145, 146, 147, 148 or 149 wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 or 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 75 or 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

151. Pharmaceutical composition according to any of 127, 128, 129, 130, 131, 132, 133, 134, 135, 136, 137, 138, 139, 140, 141, 142, 143, 144, 145, 146, 147, 148, 149 or 150, comprising at least:

a) at least one prolonged release material;
b) at least hydromorphone or a pharmaceutically acceptable salt or derivative thereof and naloxone or a pharmaceutically acceptable salt or derivative thereof; and wherein the
c) pharmaceutical composition after storage under stressed conditions releases the pharmaceutically active agents with substantially the same release rate as before subjecting the pharmaceutical composition to stressed conditions.

152. Pharmaceutical dosage form according to any of 1 to 151, wherein hydromorphone hydrochloride and naloxone hydrochloride are used.

153. Pharmaceutical dosage form according to any of 1 to 152, wherein about 1 mg, about 2 mg, about 4 mg, about 8 mg, about 12 mg, about 16 mg, about 24 mg, about 32 mg, about 40 mg, about 48 mg or about 64 mg hydromorphone hydrochloride are used.

154. Pharmaceutical dosage form according to any of 1 to 153 wherein about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride are used.

155. Method of manufacturing an oral prolonged release pharmaceutical composition according to any of 1 to 154 comprising at least the steps of:

a) producing granules comprising at least one prolonged release material, at least hydromorphone or a pharmaceutically acceptable salt or derivative thereof and at least naloxone or a pharmaceutically acceptable salt or derivative thereof,
b) optionally selecting granules of step a) of substantially uniform size;
c) optionally adding additional prolonged release material,
d) compressing said granules of step a), b) or c) to obtain an oral prolonged release pharmaceutical composition in the form of a tablet;
e) optionally heat treating said compressed granules;
f) optionally disposing a prolonged release coatings either on the granules of step a), b) or c) or on the monolithic composition obtained in step d) or e);
g) optionally curing the obtained composition.

156. Method according to 155, wherein step a) comprises the following steps:

aa) blending a prolonged release material with at least hydromorphone or a pharmaceutically acceptable salt or derivative thereof and at least naloxone or a pharmaceutically acceptable salt or derivative thereof and optionally with a filler, a lubricant, a binder, a release rate modifier, a spheronising agent and/or an anti-tacking agent;
ab) wet or dry granulating said blend of step aa) to obtain granules;
ac) drying said granules of step ab).

157. Method according to 156, wherein at least step ab) is performed by rotary pan granulation or fluidized bed granulation.

158. Method according to 155, wherein step a) comprises the following steps:
- aa) blending a prolonged release material with at least hydromorphone or a pharmaceutically acceptable salt or derivative thereof and at least naloxone or a pharmaceutically acceptable salt or derivative thereof and optionally with a spheronising agent, a filler, a lubricant, a binder, a release rate modifier, and/or an anti-tacking agent;
- ab) extruding said blend of step aa) to obtain granules; and optionally spheronising said granules of step ab);
- ac) drying said granules of step ab).

159. Method according to any of 155 to 158, wherein drying in step ac) takes place at humidity in the range of about 0.5% to about 5.0% at a temperature in the range of about 20° C. to about 90° C. and for a time in the range of about 10 min to about 3 hours.

160. Method according to any of 155 to 159, wherein granules of a mean size in the range of about 100 nm to about 2 mm are selected in step b).

161. Method according to any of 155 to 160, wherein heat treatment takes place at a temperature in the range of about 30° C. to about 95° C. and for a time in the range of about 10 min to about 3 hours.

162. Method according to any of 155 to 160, wherein the prolonged release material is selected from the group comprising hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oil and waxes.

163. Method according to 162, wherein the prolonged release material is a cellulose ether, a (meth)acrylic based (co)polymer and/or a fatty alcohol.

164. Method according to 163, wherein prolonged release material is a neutral (meth)acrylic based (co)polymer, a hydrophobic cellulose ether and/or a fatty alcohol.

165. Method according to any of 155 to 164, wherein the pharmaceutical composition comprises additionally at least one filler, at least one lubricant, at least one binder, at least one release relate modifier, at least one spheronising and at least one anti-tacking agent.

166. Method according to any of 155 to 165, wherein said filler is anhydrous lactose.

167. Method according to any of 155 to 166, wherein magnesium stearate and/or talc are used as lubricants.

168. Method according to any of 155 to 167, wherein hydroxypropyl cellulose is used as binder.

169. Method according to any of 155 to 168, wherein hydroxypropylmethyl cellulose, an anionic (meth)acrylic acid (co)polymer such as Eudragit RSPO and/or Xanthan gum are used release rate modifiers.

170. Method according to any of 155 to 169, wherein microcrystalline cellulose is used as spheronising agent.

171. Method according to any of 155 to 170, wherein the composition releases the pharmaceutically active agents with the following in vitro release rate when measured using the Ph. Eur. paddle method in 500 or 900 ml of Simulated Gastric Fluid at 75 or 100 rpm at 37 degrees C.°:
- at 1 h: 5 to 45% by weight of the pharmaceutically active agents,
- at 2 h: 15 to 55% by weight of the pharmaceutically active agents,
- at 3 h: 30 to 70% by weight of the pharmaceutically active agents,
- at 4 h: 35 to 75% by weight of the pharmaceutically active agents,
- at 6 h: 40 to 80% by weight of the pharmaceutically active agents,
- at 8 h: 50 to 90% by weight of the pharmaceutically active agents,
- at 10 h: 60 to 100% by weight of the pharmaceutically active agents,
- at 12 h: 65 to 100% by weight of the pharmaceutically active agents.

172. Method according to any of 155 to 171, wherein the ratio of the amount of the pharmaceutically active agents released after 0.5, 1 or 2 hours of in vitro dissolution of the dosage form in 500 or 900 ml of Simulated Gastric Fluid with up to 40% ethanol using the Ph. Eur. paddle method at 75 or 100 rpm at 37 degrees C.° compared to the amount of the active agents released after 0.5, 1 or 2 hours of in vitro dissolution of the dosage form in 500 or 900 ml of Simulated Gastric Fluid with 0% ethanol using the Ph. Eur. paddle method at 100 rpm at 37 degrees C.° is about 2:1 or less, is about 1.5:1 or less, is about 1:1 or less, about 1:1.2 or less, about 1:1.4 or less, about 1:1.6 or less, about 1:1.8 or less, about 1:2 or less, about 1:2.5 or less about 1:3 or less or about 1:5 or less.

173. Method according to any of 155 to 172, wherein hydromorphone hydrochloride and naloxone hydrochloride are used.

174. Method according to any of 155 to 172, wherein about 1 mg, about 2 mg, about 4 mg, about 8 mg, about 12 mg, about 16 mg, about 24 mg, about 32 mg, about 40 mg, about 48 mg or about 64 mg hydromorphone hydrochloride are used.

175. Method according to any of 155 to 172, wherein about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride are used.

176. Pharmaceutical composition obtainable by a method according to any of 155 to 175.

The invention claimed is:

1. An oral prolonged release pharmaceutical composition comprising:
   a) a prolonged release material;
   b) hydromorphone or a pharmaceutically acceptable salt or derivative thereof; and
   c) naloxone or a pharmaceutically acceptable salt or derivative thereof;
   wherein the hydromorphone or pharmaceutically acceptable salt or derivative thereof and the naloxone or pharmaceutically acceptable salt or derivative thereof are present in the pharmaceutical composition in a weight ratio of about 2:1 to about 1:3.

2. The pharmaceutical composition according to claim 1, wherein the prolonged release material and the hydromorphone or pharmaceutically acceptable salt or derivative thereof and the naloxone or pharmaceutically acceptable salt or derivative thereof form a prolonged release matrix.

3. The pharmaceutical composition according to claim 2, wherein the prolonged release material is selected from the group consisting of hydrophobic or hydrophilic polymers, protein-derived material, gums, substituted or unsubstituted hydrocarbons, digestible carbohydrates, fatty acids, fatty alcohols, glyceryl esters of fatty acids, natural and synthetic oils, natural and synthetic waxes, and any combination thereof.

4. The pharmaceutical composition according to claim 3, wherein the prolonged release material is a cellulose ether, a (meth)acrylic based (co)polymer, a fatty alcohol, or any combination thereof.

5. The pharmaceutical composition according to claim 4, wherein the prolonged release material is a neutral (meth) acrylic based (co)polymer, a hydrophobic cellulose ether, a fatty alcohol, or any combination thereof.

6. The pharmaceutical composition according to claim 2, wherein the pharmaceutical composition additionally comprises a filler, a lubricant, a binder, a release rate modifier, a spheronising agent, an anti-tacking agent, or any combination thereof.

7. The pharmaceutical composition according to claim 6, wherein the pharmaceutical composition additionally comprises a filler and the filler is anhydrous lactose.

8. The pharmaceutical composition according to claim 6, wherein the pharmaceutical composition additionally comprises a lubricant and the lubricant is magnesium stearate, talc, or a combination thereof.

9. The pharmaceutical composition according to claim 6, wherein the pharmaceutical composition additionally comprises a binder and the binder is hydroxypropyl cellulose.

10. The pharmaceutical composition according to claim 2, wherein the prolonged release matrix is heat treated.

11. The pharmaceutical composition according to claim 10, wherein the prolonged release matrix is heat treated at a temperature in the range of about 30° C. to about 95° C. and for a time in the range of about 10 min to about 3 hours.

12. The pharmaceutical composition according to claim 2, wherein a prolonged release coating is disposed on the prolonged release matrix.

13. The pharmaceutical composition according to claim 1, wherein the composition releases the pharmaceutically active agents (the hydromorphone or pharmaceutically acceptable salt or derivative thereof and the naloxone or pharmaceutically acceptable salt or derivative thereof) with the following in vitro release rates when measured using the Ph. Eur. paddle method in 500 or 900 ml of Simulated Gastric Fluid at 75 or 100 rpm at 37 degrees C.°:
   at 1 h: 25 to 55% by weight of the pharmaceutically active agents,
   at 2 h: 45 to 75% by weight of the pharmaceutically active agents,
   at 3 h: 55 to 85% by weight of the pharmaceutically active agents,
   at 4 h: 60 to 90% by weight of the pharmaceutically active agents,
   at 6 h: 70 to 100% by weight of the pharmaceutically active agents,
   at 8 h: more than 85% by weight of the pharmaceutically active agents, and
   at 10 h: more than 90% by weight of the pharmaceutically active agents.

14. The pharmaceutical composition according to claim 1, wherein the ratio of the amount of the pharmaceutically active agents (the hydromorphone or pharmaceutically acceptable salt or derivative thereof and the naloxone or pharmaceutically acceptable salt or derivative thereof) released after 0.5, 1, or 2 hours of in vitro dissolution of the pharmaceutical composition in 500 or 900 ml of Simulated Gastric Fluid with up to 40% ethanol using the Ph. Eur. paddle method at 75 or 100 rpm at 37 degrees C.° compared to the amount of the pharmaceutically active agents released after 0.5, 1, or 2 hours of in vitro dissolution of the pharmaceutical composition in 500 or 900 ml of Simulated Gastric Fluid with 0% ethanol using the Ph. Eur. paddle method at 75 or 100 rpm at 37 degrees C.° is about 2:1 or less.

15. The pharmaceutical composition according to claim 1, wherein the pharmaceutical composition after storage under stressed conditions releases the hydromorphone or pharmaceutically acceptable salt or derivative thereof and the naloxone or pharmaceutically acceptable salt or derivative thereof with substantially the same release rate as before subjecting the pharmaceutical composition to stressed conditions.

16. The pharmaceutical composition according to claim 1, wherein the pharmaceutical composition after storage under stressed conditions has less than 4% of total substances related to hydromorphone or a pharmaceutically acceptable salt or derivative thereof or related to naloxone or a pharmaceutically acceptable salt or derivative thereof.

17. The pharmaceutical composition according to claim 1, wherein the pharmaceutical composition is a multiparticulate formulation.

18. The pharmaceutical composition according to claim 1, wherein the hydromorphone or pharmaceutically acceptable salt or derivative thereof is hydromorphone hydrochloride and the naloxone or pharmaceutically acceptable salt or derivative thereof is naloxone hydrochloride.

19. The pharmaceutical composition according to claim 18, wherein the hydromorphone hydrochloride is present at an amount equivalent to about 1 mg, about 2 mg, about 4 mg, about 8 mg, about 12 mg, about 16 mg, about 24 mg, about 32 mg, about 40 mg, about 48 mg or about 64 mg of anhydrous hydromorphone hydrochloride.

20. The pharmaceutical composition according to claim 18, wherein the naloxone hydrochloride is present at an amount equivalent to about 1 mg, about 2 mg, about 4 mg, about 8 mg, about 12 mg, about 16 mg, about 24 mg, about 32 mg, about 48 mg, about 64 mg, about 96 mg, about 128 or about 256 mg of anhydrous naloxone hydrochloride.

21. The pharmaceutical composition according to claim 1, wherein the hydromorphone or pharmaceutically acceptable salt or derivative thereof and the naloxone or pharmaceutically acceptable salt or derivative thereof are present in the pharmaceutical composition in a weight ratio of about 2:1.

22. The pharmaceutical composition according to claim 1, wherein the hydromorphone or pharmaceutically acceptable salt or derivative thereof and the naloxone or pharmaceutically acceptable salt or derivative thereof are present in the pharmaceutical composition in a weight ratio of about 1:1.

23. The pharmaceutical composition according to claim 1, wherein the hydromorphone or pharmaceutically acceptable salt or derivative thereof and the naloxone or pharmaceutically acceptable salt or derivative thereof are present in the pharmaceutical composition in a weight ratio of about 1:2.

24. The pharmaceutical composition according to claim 1, wherein the hydromorphone or pharmaceutically acceptable salt or derivative thereof and the naloxone or pharmaceutically acceptable salt or derivative thereof are present in the pharmaceutical composition in a weight ratio of about 1:3.

25. The pharmaceutical composition according to claim 1, wherein the pharmaceutical composition comprises about 1 to about 64 mg of hydromorphone hydrochloride or equimolar amounts of any other pharmaceutically acceptable salt or the free base of hydromorphone.

26. The pharmaceutical composition according to claim 25, wherein the pharmaceutical composition comprises about 1 mg, about 2 mg, about 4 mg, about 8 mg, about 12 mg, about 16 mg, about 24 mg, about 32 mg, about 40 mg, about 48 mg or about 64 mg of hydromorphone hydrochloride or equimolar amounts of any other pharmaceutically acceptable salt or the free base of hydromorphone.

27. The pharmaceutical composition according to claim 1, wherein the pharmaceutical composition comprises about 1 to about 256 mg of naloxone hydrochloride or equimolar amounts of any other pharmaceutically acceptable salt or the free base of naloxone.

28. The pharmaceutical composition according to claim 27, wherein the pharmaceutical composition comprises about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride or equimolar amounts of any other pharmaceutically acceptable salt or the free base of naloxone.

29. The pharmaceutical composition according to claim 1, wherein the pharmaceutical composition is in the form of a tablet.

30. The pharmaceutical composition according to claim 1, wherein the pharmaceutical composition is formulated for twice-a-day administration.

31. The pharmaceutical composition according to claim 1, wherein the pharmaceutical composition releases the hydromorphone or pharmaceutically acceptable salt or derivative thereof and the naloxone or pharmaceutically acceptable salt or derivative thereof with substantially the same release rate.

32. The pharmaceutical composition according to claim 31, wherein the release of the hydromorphone or pharmaceutically acceptable salt or derivative thereof and the naloxone or pharmaceutically acceptable salt or derivative thereof is measured using the Ph. European paddle method at 75 rpm in 500 ml simulated gastric fluid (SGF) dissolution medium (0.1 N HCl with pH 1.2).

33. The pharmaceutical composition according to claim 31, wherein the release of the hydromorphone or pharmaceutically acceptable salt or derivative thereof and the naloxone or pharmaceutically acceptable salt or derivative thereof is measured using the Ph. European paddle method at 75 rpm in 500 ml simulated gastric fluid (SGF) dissolution medium (0.1 N HCl with pH 1.2) with 40% ethanol.

34. The pharmaceutical composition according to claim 1, wherein the composition releases the pharmaceutically active agents (the hydromorphone or pharmaceutically acceptable salt or derivative thereof and the naloxone or pharmaceutically acceptable salt or derivative thereof) with the following in vitro release rate when measured using the Ph. Eur. paddle method in 500 or 900 ml of Simulated Gastric Fluid at 100 rpm at 37 degrees C.°:
  at 4 h: 60 to 90% by weight of the pharmaceutically active agents.

35. The pharmaceutical composition according to claim 1, wherein the composition releases the pharmaceutically active agents (the hydromorphone or pharmaceutically acceptable salt or derivative thereof and the naloxone or pharmaceutically acceptable salt or derivative thereof) with the following in vitro release rate when measured using the Ph. Eur. paddle method in 500 or 900 ml of Simulated Gastric Fluid at 75 or 100 rpm at 37 degrees C.°:
  at 6 h: 70 to 100% by weight of the pharmaceutically active agents.

36. The pharmaceutical composition according to claim 1, wherein the composition releases the pharmaceutically active agents (the hydromorphone or pharmaceutically acceptable salt or derivative thereof and the naloxone or pharmaceutically acceptable salt or derivative thereof) with the following in vitro release rate when measured using the Ph. Eur. paddle method in 500 or 900 ml of Simulated Gastric Fluid at 75 or 100 rpm at 37 degrees C.°:
  at 10 h: more than 90% by weight of the pharmaceutically active agents.

37. A method of treating pain, comprising administering to a patient in need thereof a pharmaceutical composition according to claim 1.

38. A method of reducing constipation in a patient being treated for pain with an opioid, comprising administering to the patient a pharmaceutical composition according to claim 1.

39. A method of treating pain, comprising administering to a patient in need thereof a pharmaceutical composition according to claim 1; wherein the patient's constipation is reduced.

40. An oral prolonged release pharmaceutical composition comprising:
  a) a prolonged release material;
  b) hydromorphone or a pharmaceutically acceptable salt thereof; and
  c) naloxone or a pharmaceutically acceptable salt thereof;
  wherein the hydromorphone or pharmaceutically acceptable salt thereof and the naloxone or pharmaceutically acceptable salt thereof are present in the pharmaceutical composition in a weight ratio of about 1:1; and
  wherein the naloxone or pharmaceutically acceptable salt thereof is present in the pharmaceutical compositions as about 1 to about 256 mg of naloxone hydrochloride or equimolar amounts of any other pharmaceutically acceptable salt or the free base of naloxone.

41. The pharmaceutical composition according to claim 40, wherein the pharmaceutical composition comprises about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride or equimolar amounts of any other pharmaceutically acceptable salt or the free base of naloxone.

42. The pharmaceutical composition according to claim 40, wherein the pharmaceutical composition comprises about 1 to about 64 mg of hydromorphone hydrochloride or equimolar amounts of any other pharmaceutically acceptable salt or the free base of hydromorphone.

43. An oral prolonged release pharmaceutical composition comprising:
  a) a prolonged release material;
  b) hydromorphone or a pharmaceutically acceptable salt thereof; and
  c) naloxone or a pharmaceutically acceptable salt thereof;
  wherein the hydromorphone or pharmaceutically acceptable salt thereof and the naloxone or pharmaceutically acceptable salt thereof are present in the pharmaceutical composition in a weight ratio of about 1:2; and
  wherein the naloxone or pharmaceutically acceptable salt thereof is present in the pharmaceutical compositions as about 1 to about 256 mg of naloxone hydrochloride or equimolar amounts of any other pharmaceutically acceptable salt or the free base of naloxone.

44. The pharmaceutical composition according to claim 43, wherein the pharmaceutical composition comprises about 1 mg, about 2 mg, about 4 mg, about 8 mg, about 12 mg, about 16 mg, about 24 mg, about 32 mg, about 48 mg, about 64 mg, about 96 mg, about 128 or about 256 mg of naloxone hydrochloride or equimolar amounts of any other pharmaceutically acceptable salt or the free base of naloxone.

45. The pharmaceutical composition according to claim 43, wherein the pharmaceutical composition comprises about 1 to about 64 mg of hydromorphone hydrochloride or equimolar amounts of any other pharmaceutically acceptable salt or the free base of hydromorphone.

46. A method of manufacturing an oral prolonged release pharmaceutical composition according to claim 1 comprising:
- a) producing granules comprising the prolonged release material, the hydromorphone or pharmaceutically acceptable salt or derivative thereof, and the naloxone or pharmaceutically acceptable salt or derivative thereof,
- b) optionally selecting granules of step a) of substantially uniform size;
- c) optionally adding additional prolonged release material;
- d) optionally compressing said granules of step a), b) or c) to obtain an oral prolonged release pharmaceutical composition in the form of a tablet;
- e) optionally heat treating the product of steps a), b), c) or d);
- f) optionally coating with a prolonged releasing coating;
- g) optionally curing the composition.

47. The method according to claim 46, wherein step a) comprises the following steps:
- aa) blending the prolonged release material with the hydromorphone or pharmaceutically acceptable salt or derivative thereof and the naloxone or pharmaceutically acceptable salt or derivative thereof and optionally with a filler, a lubricant, a binder, a release rate modifier, a spheronising agent, an anti-tacking agent, or any combination thereof;
- ab) dry granulating or extruding said blend of step aa) to obtain granules;
- ac) optionally drying said granules of step ab).

48. The method according to claim 46, wherein step e) is performed and the heat treatment takes place at a ambient humidity at a temperature in the range of about 40° C. to about 90° C. and for a time in the range of about 15 min to about 90 min.

* * * * *

UNITED STATES PATENT AND TRADEMARK OFFICE
CERTIFICATE OF CORRECTION

PATENT NO. : 9,700,508 B2
APPLICATION NO. : 13/697197
DATED : July 11, 2017
INVENTOR(S) : Helen K. Danagher et al.

It is certified that error appears in the above-identified patent and that said Letters Patent is hereby corrected as shown below:

In the Claims

In Column 94, Claim 40, Line 28, please change "in the pharmaceutical compositions" to --in the pharmaceutical composition--.

In Column 94, Claim 43, Line 56, please change "in the pharmaceutical compositions" to --in the pharmaceutical composition--.

In Column 96, Claim 46, Line 1, please change "with a prolonged releasing" to --with a prolonged release--.

In Column 96, Claim 48, Line 17, please change "at a ambient" to --at an ambient--.

Signed and Sealed this
Tenth Day of April, 2018

Andrei Iancu
*Director of the United States Patent and Trademark Office*